United States Patent [19]

Smyser et al.

[11] Patent Number: 5,532,356
[45] Date of Patent: Jul. 2, 1996

[54] METHOD FOR PREPARING N,N'-DISUBSTITUTED CYCLIC UREAS

[75] Inventors: Thomas E. Smyser; Pasquale N. Confalone, both of Wilmington, Del.

[73] Assignee: The DuPont Merck Pharmaceutical Company, Wilmington, Del.

[21] Appl. No.: 469,409

[22] Filed: Jun. 6, 1995

[51] Int. Cl.[6] ......................... C07D 243/08; A61K 31/55
[52] U.S. Cl. .............................................. 540/492
[58] Field of Search ............................. 540/492

[56] References Cited

FOREIGN PATENT DOCUMENTS

| WO93/07128 | 4/1993 | WIPO | 540/492 |
| WO94/19329 | 9/1994 | WIPO | 540/492 |

Primary Examiner—Robert T. Bond
Attorney, Agent, or Firm—Blair Q. Ferguson

[57] ABSTRACT

The present invention relates to methods for the preparation of disubstituted cyclic ureas of the formula (IV):

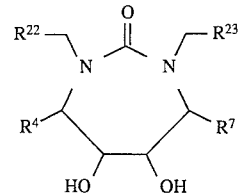

from linear diaminodiols. These cyclic urea compounds are useful as HIV protease inhibitor compounds for the treatment of HIV infection.

8 Claims, No Drawings

METHOD FOR PREPARING N,N'-DISUBSTITUTED CYCLIC UREAS

FIELD OF THE INVENTION

The present invention relates generally to methods for the preparation of N,N'-disubstituted cyclic ureas from linear diaminodiols. These cyclic urea compounds are useful as HIV protease inhibitor compounds for the treatment of HIV infection.

BACKGROUND OF THE INVENTION

The starting materials for the methods of the present invention are linear diamino diols. These compounds include nonpeptide C-2 symmetric and pseudosymmetric compounds which have biological activity as human immunodeficiency virus (HIV) protease inhibitors. Numerous methods for their preparation are found in the literature. The N,N'-disubstituted cyclic urea products of the methods of the present invention have also exhibited biological activity as human immunodeficiency virus (HIV) protease inhibitors for the treatment of HIV infection.

Linear diaminodiols and methods for their preparation are found in the literature, for example in the following references: Kempf et al., *J. Org. Chem.* 57, 5692–5700 (1992); Livermore et al., *J. Med. Chem.* 36, 3784–3794 (1993); Lam et al., *Science* 263, 380–384 (1994); Dreyer et al., *Biochemistry* 32, 937–47 (1993); Sowin et al. WO 93/23361; Jadhav et al., *Bioorganic & Med. Chem. Lett.* 2, 353–356 (1992); Jadhav et al., U.S. Pat. No. 5,294,720 (issued Mar. 15, 1994); Dreyer et al., *Biochemistry* 32(3), 937–47 (1993); Canadian Patent Application 2,026,832 (German Patent Application DE 4030350); European Patent Application No. WO 92/00948; U.S. Pat. No. 4,837,204; and European Patent Application Publication Number 486,948.

Acetonide has been used to protect the diol function in the preparation of linear HIV protease inhibitors (Baker et al., *J. Org. Chem.* 58, 3277–3284 (1993); Baker et al., *Tetrahedron Lett.* 33, 1581–1584 (1992)).

Lam et al., PCT International Publication Number WO 93/07,128, EP 402646 A1, and copending commonly assigned U.S. patent application Ser. No. 08/197,630, filed Feb. 16, 1994, disclose cyclic carbonyl compounds and derivatives thereof which are useful as HIV protease inhibitors for the treatment of HIV infection. Such cyclic compounds, which may be made using the processes of the present invention, are non-peptidic, low molecular weight, orally bioavailable compounds useful as inhibitors of HIV protease and for the treatment of HIV infection.

Copending commonly assigned U.S. patent application Ser. No. 08/268,609, filed Jun. 30, 1994, discloses a process for the preparation of nitrogen-unsubstituted linear diaminodiols having an acetonide protecting group for the diol as shown in Scheme 1, and the cyclization of the nitrogen-unsubstituted acetonide protected linear diamino diol (V) to form a cyclic urea product compound.

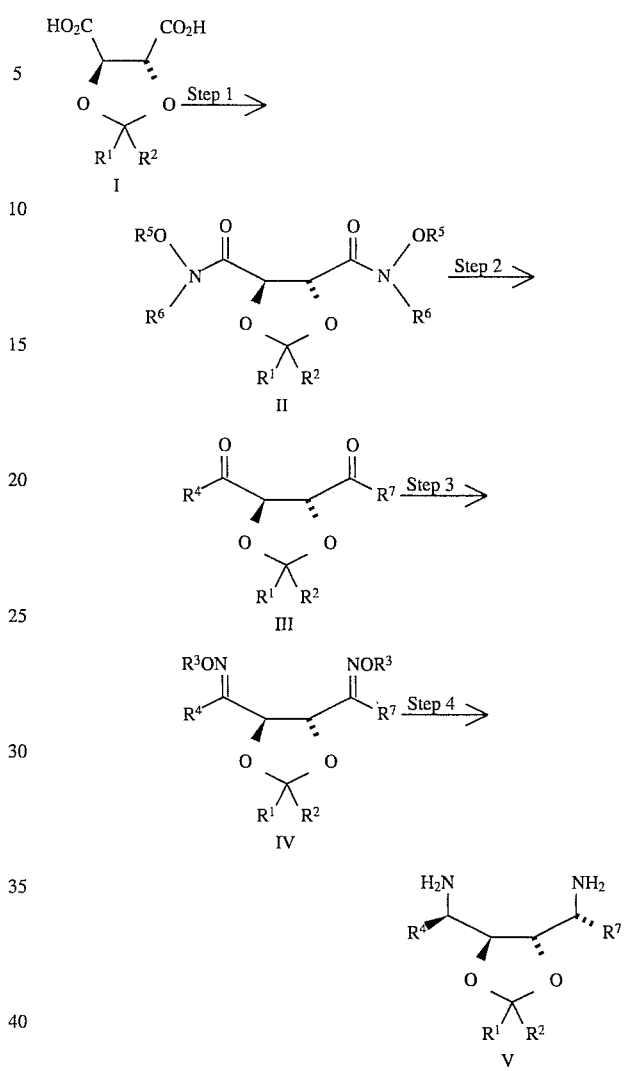

Copending commonly assigned U.S. patent application Ser. No. 08/269,320, filed Jun. 30, 1994, discloses a process for the preparation of nitrogen-unsubstituted dihydroxy cyclic ureas having an acetonide protecting group for the diol as shown below in Scheme 2. The cyclization to the cyclic urea takes place on the diamino diol (VI) in which nitrogen is unprotected and the hydroxyls bear an acyclic protecting group. The diol protecting group had to be changed midway through the synthesis in order to optimize the cyclization and alkylation yields.

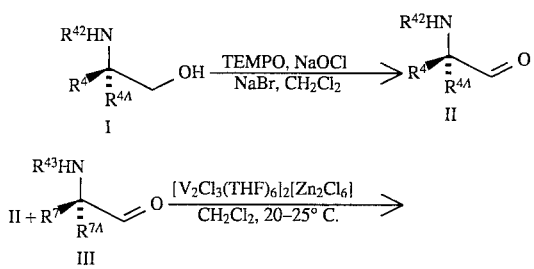

3

-continued
Scheme 2

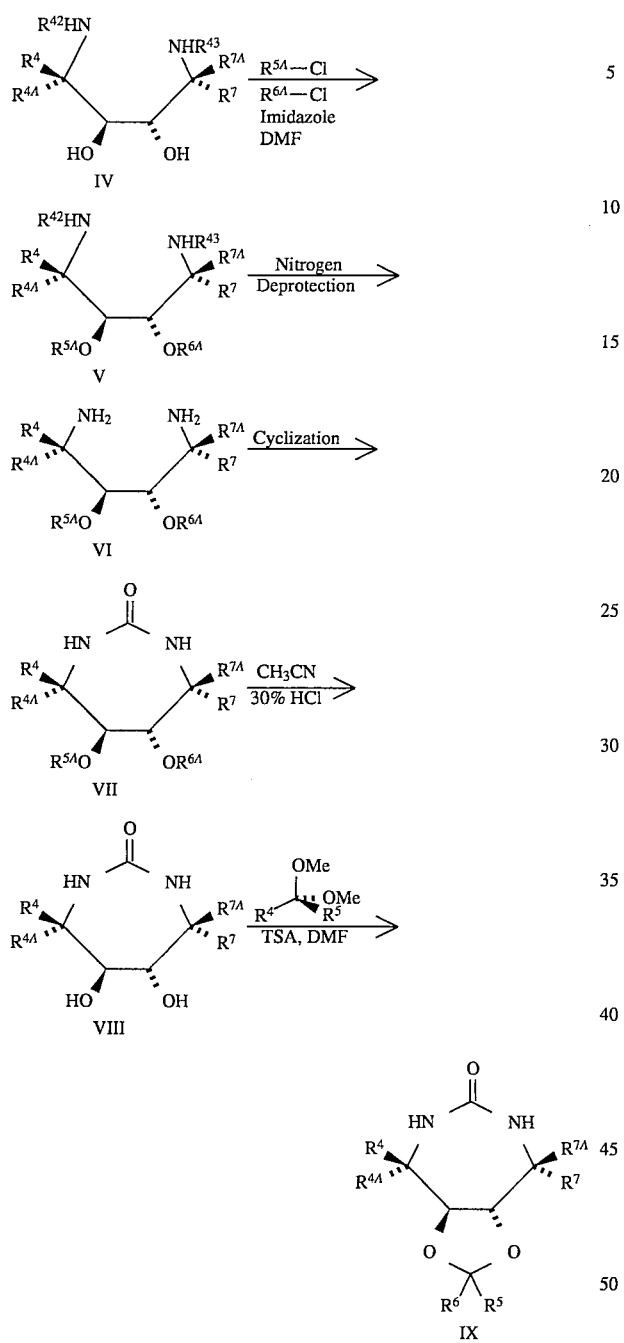

Copending commonly assigned U.S. patent application Ser. No. 08/268,702 filed Jun. 30, 1994, discloses a process for the preparation of nitrogen-unsubstituted dihydroxy cyclic ureas having a trioxepane protecting group for the diol as shown in Scheme 3. In this case the cyclization to the cyclic urea takes place on the nitrogen-unsubstituted trioxepane protected diaminodiol (IV).

4

Scheme 3

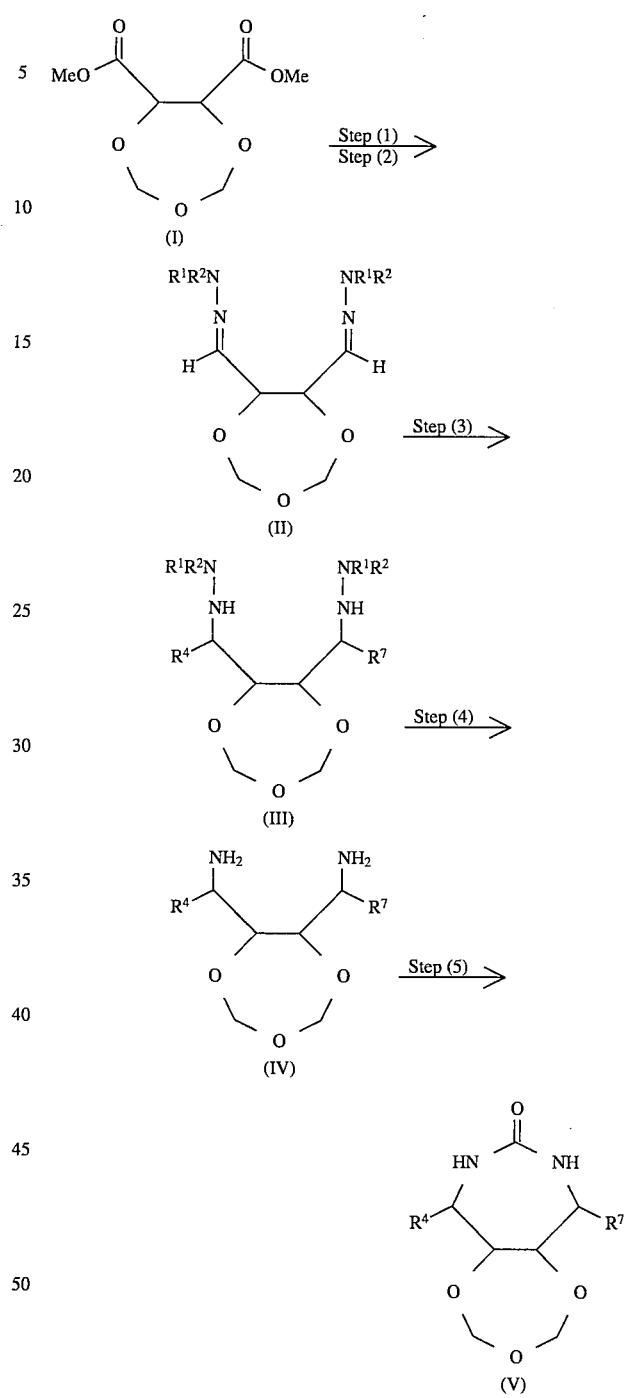

Copending commonly assigned U.S. patent application Ser. No. 08/230,562, filed Apr. 20, 1994, discloses a process for the preparation of symmetrically or unsymmetrically nitrogen-disubstituted or nitrogen-monosubstituted cyclic ureas having a broad range of hydroxy protecting groups for the diol as shown below in Scheme 4. In this process, chromatographic separation of the unsubstituted and monosubstituted cyclic urea is required. Under the conditions disclosed in this reference, cyclization of the nitrogen-disubstituted hydroxyl protected diaminodiol with 1,1'-carbonyldiimidazole does not take place.

Scheme 4

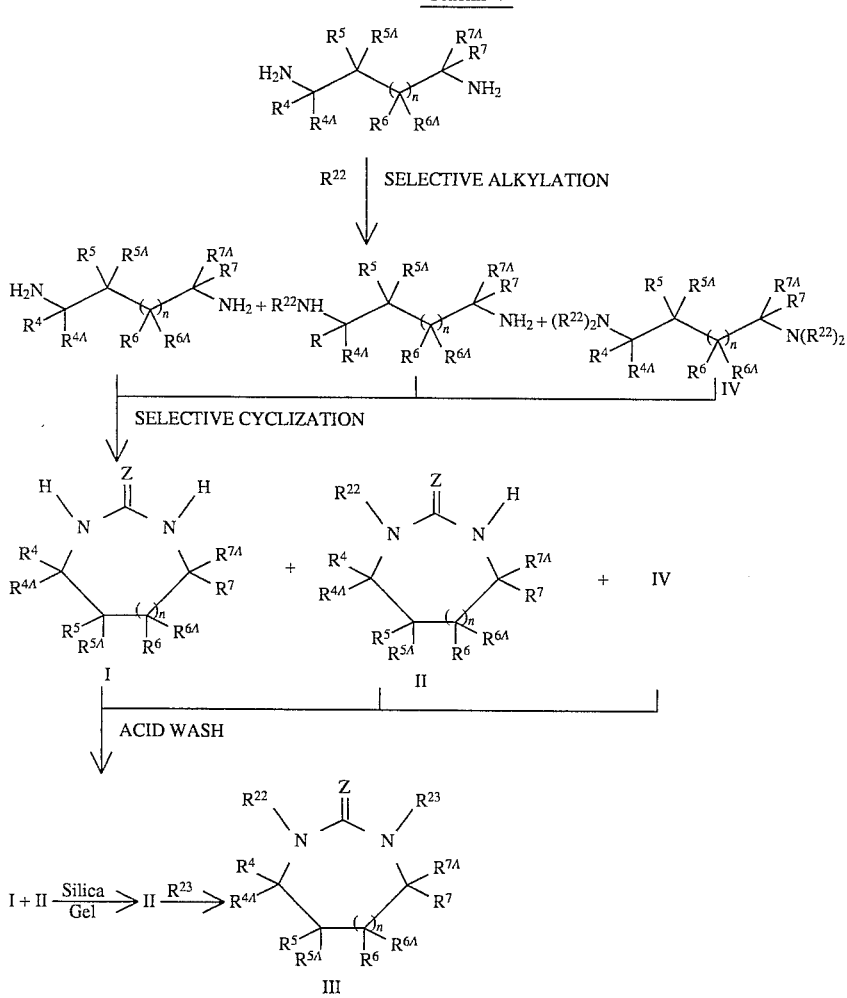

Copending commonly assigned U.S. patent application Ser. No. 08/197,630, filed Feb. 16, 1994, discloses a process for the preparation of symmetrically or unsymmetrically nitrogen-disubstituted or nitrogen-monosubstituted cyclic ureas having various hydroxy protecting groups, via cyclization of an un- ($R^{22}$ and $R^{23}$ are H), mono- (one of $R^{22}$ and $R^{23}$ are H and the other is nonhydrogen) or disubstituted (both $R^{22}$ and $R^{23}$ are not hydrogen) linear diamine to the respective cyclic urea as shown in Scheme 5.

Scheme 5

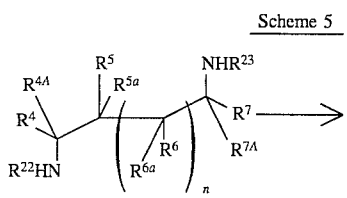

-continued
Scheme 5

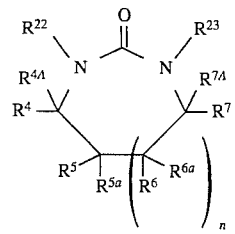

Also disclosed in this reference is the cyclization of a nitrogen-unsubstituted acetonide protected diaminodiol with CDI. The cyclization of a nitrogen-unsubstituted bis-Mem protected diaminodiol was shown to occur in high yield. The cyclization of a bis-Mem protected bis-monophenylhydrazinodiol (I) with phosgene to the corresponding cyclic urea (II), as shown below in Scheme is disclosed in this reference.

Scheme 6

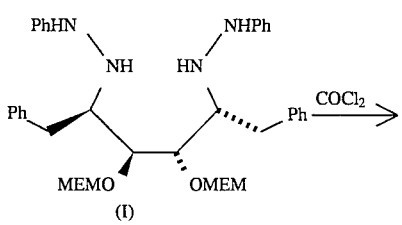
(I)

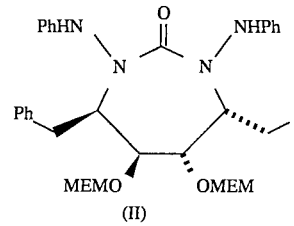
(II)

The use of acyclic diol protecting groups allowed for high cyclization yields but produced intermediates which were undesirable oils. These intermediates also lead to lower yields in subsequent steps of the process.

Despite the various methods for their preparation, there still exists a need for more efficient and cost-effective methods for the preparation of such cyclic urea HIV protease inhibitor compounds in high yields from readily available starting materials. The present invention provides improved processes for the synthesis of such cyclic urea HIV protease inhibitor compounds and processes for the synthesis of intermediates for the synthesis of such cyclic urea HIV protease inhibitor compounds.

The present invention comprises a process which allows the entire synthetic sequence leading to the desired HIV protease inhibitors to be carried out using the inexpensive acetonide or oxydimethylene-1,3-diyl protecting groups. The present invention comprises an initial reductive alkylation of the diamine affording a crystalline intermediate in high yield. This intermediate compound undergoes cyclization with phosgene in high yield to produce another crystalline intermediate, providing an optimal process. Advantages of the present invention include: a) reduction in the number of chemical steps; b) increase in overall yield; and c) formation of crystalline intermediates.

SUMMARY OF THE INVENTION

The present invention comprises processes for the preparation of nitrogen substituted cyclic urea compounds, and intermediates therefor, which compounds are capable of inhibiting HIV protease and HIV proliferation and are useful for the treatment of HIV infection.

[1] There is provided by this invention a process for the preparation of compounds of the formula (II), (III) and (IV):

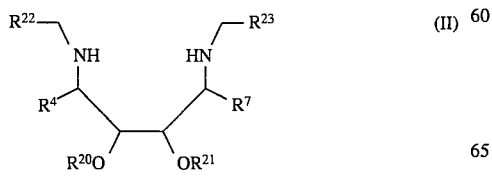

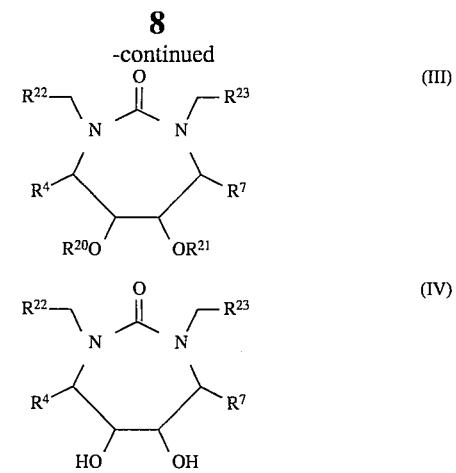

wherein:

$R^4$ and $R^7$ are independently selected from the following groups:

$C_1$–$C_8$ alkyl substituted with 0–3 $R^{11}$;
$C_2$–$C_8$ alkenyl substituted with 0–3 $R^{11}$;
$C_2$–$C_8$ alkynyl substituted with 0–3 $R^{11}$;

$R^{11}$ is selected from one or more of the following:

H, keto, halogen, cyano, —$CH^2NR^{13}R^{14}$, —$NR^{13}R^{14}$, —$CO_2R^{13}$, —$OC(=O)$ $R^{13}$, —$OR^{13}$, —$S(O)_mR^{13}$, —$NHC(=NH)NHR^{13}$, —$C(=NH)NHR^{13}$, —$C(=O)NR^{13}R^{14}$, —$NR^{14}C(=O)R^{13}$, =$NOR^{14}$, —$NR^{14}C(=O)OR^{14}$, —$OC(=O)NR^{13}R^{14}$, —$NR^{13}C(=O)NR^{13}R^{14}$, —$NR^{14}SO_2NR^{13}R^{14}$, —$NR^{14}SO_2R^{13}$, —$SO_2NR^{13}R^{14}$, —$OP(O)$ $(OR^{13})_2$, $C_1$–$C_4$ alkyl, $C_2$–$C_4$ alkenyl, $C_3$–$C_6$ cycloalkylmethyl, phenyl, benzyl, phenethyl, phenoxy, benzyloxy, nitro, $C_7$–$C_{10}$ arylalkyl, hydroxamic acid, hydrazide, boronic acid, sulfonamide, formyl, $C_3$–$C_6$ cycloalkoxy, $C_1$–$C_4$ alkyl substituted with —$NR^{13}R^{14}$, $C_1$–$C_4$ hydroxyalkyl, methylenedioxy, ethylenedioxy, $C_1$–$C_4$ haloalkyl, $C_1$–$C_4$ haloalkoxy, $C_1$–$C_4$ alkoxycarbonyl, pyridylcarbonyloxy, $C_1$–$C_4$ alkylcarbonyl, $C_1$–$C_4$ alkylcarbonylamino, —$OCH_2CO_2H$, 2-(1-morpholino)ethoxy, azido, —$C(R^{14})=N(OR^{14})$; or $C_3$–$C_{10}$ cycloalkyl substituted with 0–2 $R^{12}$;
$C_1$–$C_4$ alkyl substitued with 0–2 $R^{12}$;
aryl ($C_1$–$C_3$ alkyl)-, substituted with 0–2 $R^{12}$;
$C_2$–$C_6$ alkoxyalkyl-, substituted with 0–2 $R^{12}$;
$C_1$–$C_4$ alkylcarbonyloxy substituted with 0–2 $R^{12}$;
$C_6$–$C_{10}$ arylcarbonyloxy substituted with 0–2 $R^{12}$;
a $C_5$–$C_{14}$ carbocyclic residue substituted with 0–3 $R^{12}$;
a 5- to 10-membered heterocyclic ring system containing 1 to 4 heteroatoms independently selected from oxygen, nitrogen or sulfur, said heterocyclic ring system being substituted with 0–3 $R^{12}$;

$R^{11A}$ is selected from one or more of the following:

H, keto, halogen, cyano, —$CH_2N(R^{13A})R(^{14A})$, —$OR^{13A}$ —$N(R^{13A})R(^{14A})$, —$CO_2H$, —$OC(=O)$ ($C_1$–$C_3$ alkyl), —OH, $C_2$–$C_6$ alkoxyalkyl, —$C(=O)NH_2$, —$OC(=O)NH_2$, —$NHC(=O)NH_2$, —$SO_2NH_2$, $C_1$–$C_4$ alkyl, $C_2$–$C_4$ alkenyl, $C_3$–$C_{10}$ cycloalkyl, $C_3$–$C_6$ cycloalkylmethyl, benzyl, phenethyl, phenoxy, benzyloxy, nitro, $C_7$–$C_{10}$ arylalkyl, hydroxamic acid, hydrazide, boronic acid, $C_3$–$C_6$ cycloalkoxy, $C_1$–$C_4$ alkyl substituted with —$NH_2$, $C_1$–$C_4$ hydroxyalkyl, methylenedioxy, ethylenedioxy, $C_1$–$C_4$ haloalkyl, $C_1$–$C_4$ haloalkoxy, $C_1$–$C_4$ alkoxycarbonyl, $C_1$–$C_4$ alkylcarbonyloxy, $C_1$–$C_4$ alkylcarbonyl, $C_1$–C4 alkylcarbonylamino, —$OCH_2CO_2H$, 2-(1-morpholino)ethoxy, azido, aryl($C_1$–$C_3$ alkyl); or $C_3$–$C_{10}$ cycloalkyl substituted with 0–2 $R^{12A}$, $C_1$–$C_4$ alkyl substituted with 0–2 $R^{12A}$, aryl($C_1$–$C_3$ alkyl)- substituted with 0–2 $R^{12A}$;

a 5- to 10-membered heterocyclic ring system containing 1 to 4 heteroatoms independently selected from oxygen, nitrogen or sulfur, said heterocyclic ring system substituted with 0–3 $R^{12A}$; or —$SO_mR^{13A}$, $C_1$–$C_4$ haloalkyl, $C_1$–$C_4$ haloalkoxy, $C_1$–$C_4$ alkoxy, $C_2$–$C_4$ alkynyl, phenyl, said phenyl being optionally substituted with Cl, F, Br, CN, $NO_2$, $CF_3$, $C_1$–$C_4$ alkyl, $C_1$–$C_4$ alkoxy or OH; or alternately, $R^{11A}$ and $R^{16}$, when substituents on adjacent carbons, can be taken together with the carbon atoms to which they are attached to form a 5–6 membered carbocyclic or heterocyclic ring system, said carbocyclic or heterocyclic ring system being optionally substituted with Cl, F, Br, CN, $NO_2$, $CF_3$, $C_1$–$C_4$ alkyl, $C_1$–$C_4$ alkoxy or OH;

$R^{12}$, when a substituent on carbon, is selected from one or more of the following:

phenyl, benzyl, phenethyl, phenoxy, benzyloxy, halogen, hydroxy, nitro, cyano, $C_1$–$C_4$ alkyl, $C_3$–$C_6$ cycloalkyl, $C_3$–$C_6$ cycloalkylmethyl, $C_7$–$C_{10}$ arylalkyl, $C_1$–$C_4$ alkoxy, —$CO_2H$, hydroxamic acid, hydrazide, boronic acid, sulfonamide, formyl, $C_3$–$C_6$ cycloalkoxy, —$OR^{13}$, —$NR^{13}R^{14}$, $C_1$–$C_4$ alkyl substituted with —$NR^{13}R^{14}$, $C_2$–$C_6$ alkoxyalkyl optionally substituted with —$Si(CH_3)_3$, $C_1$–$C_4$ hydroxyalkyl, methylenedioxy, ethylenedioxy, $C_1$–$C_4$ haloalkyl, $C_1$–$C_4$ haloalkoxy, $C_1$–$C_4$ alkoxycarbonyl, $C_1$–$C_4$ alkylcarbonyloxy, $C_1$–$C_4$ alkylcarbonyl, $C_1$–$C4$ alkylcarbonylamino, —$S(O)_mR^{13}$, —$SO_2NR^{13}R^{14}$, —$NHSO_2R^{14}$, —$OCH_2CO_2R^{13}$, 2-(1-morpholino)ethoxy, —$C(R^{14})=N(OR^{14})$; or a 5- or 6-membered heterocyclic ring containing from 1 to 4 heteroatoms independently selected from oxygen, nitrogen or sulfur;

or $R^{12}$ may be a 3- or 4- carbon chain attached to adjacent carbons on the ring to form a fused 5- or 6-membered ring, said 5- or 6- membered ring being optionally substituted on the aliphatic carbons with halogen, $C_1$–$C_4$ alkyl, $C_1$–$C_4$ alkoxy, hydroxy, or —$NR^{13}R^{14}$; or when $R^{12}$ is attached to a saturated carbon atom, it may be =O or =S; or when $R^{12}$ is attached to sulfur it may be =O.

$R^{12}$, when a substituent on nitrogen, is selected from one or more of the following:

phenyl, benzyl, phenethyl, hydroxy, $C_1$–$C_4$ hydroxyalkyl, $C_1$–$C_4$ alkoxy, $C_1$–$C_4$ alkyl, $C_3$–$C_6$ cycloalkyl, $C_3$–$C_6$ cycloalkylmethyl, —$CH_2NR^{13}R^{14}$, —$NR^{13}R^{14}$, $C_2$–$C_6$ alkoxyalkyl, $C_1$–$C_4$ haloalkyl, $C_1$–$C_4$ alkoxycarbonyl, —$CO_2H$, $C_1$–$C_4$ alkylcarbonyloxy, $C_1$–$C_4$ alkylcarbonyl, —$C(R^{14})=N(OR^{14})$;

$R^{12A}$, when a substituent on carbon, is selected from one or more of the following:

phenyl, benzyl, phenethyl, phenoxy, benzyloxy, halogen, hydroxy, nitro, cyano, $C_1$–$C_4$ alkyl, $C_3$–$C_6$ cycloalkyl, $C_3$–$C_6$ cycloalkylmethyl, $C_7$–$C_{10}$ arylalkyl, $C_1$–$C_4$ alkoxy, —$CO_2H$, hydroxamic acid, hydrazide, boronic acid, sulfonamide, formyl, $C_3$–$C_6$ cycloalkoxy, —$OR^{13A}$, $C_2$–$C_6$ alkoxyalkyl optionally substituted with —$Si(CH_3)_3$, $C_1$–$C_4$ hydroxyalkyl, methylenedioxy, ethylenedioxy, $C_1$–$C_4$ haloalkyl, $C_1$–$C_4$ haloalkoxy, $C_1$–$C_4$ alkoxycarbonyl, $C_1$–$C_4$ alkylcarbonyloxy, $C_1$–$C_4$ alkylcarbonyl, $C_1$–$C_4$ alkylcarbonylamino, —$S(O)_mMe$, —$SO_2NH_2$, —$NHSO_2Me$, —$OCH_2CO_2R^{13A}$, 2-(1-morpholino) ethoxy; or a 5- or 6-membered heterocyclic ring containing from 1 to 4 heteroatoms independently selected from oxygen, nitrogen or sulfur; or $R^{12A}$ may be a 3- or 4- carbon chain attached to adjacent carbons on the ring to form a fused 5- or 6-membered ring, said 5- or 6- membered ring being optionally substituted on the aliphatic carbons with halogen, $C_1$–$C_4$ alkyl, $C_1$–$C_4$ alkoxy, hydroxy, or —$NH_2$; or, when $R^{12A}$ is attached to a saturated carbon atom, it may be =O or =S; or when $R^{12A}$ is attached to sulfur it may be =O.

$R^{12A}$, when a substituent on nitrogen, is selected from one or more of the following:

phenyl, benzyl, phenethyl, hydroxy, $C_1$–$C_4$ hydroxyalkyl, $C_1$–$C_4$ alkoxy, $C_1$–$C_4$ alkyl, $C_3$–$C_6$ cycloalkyl, $C_3$–$C_6$ cycloalkylmethyl, $C_2$–$C_6$ alkoxyalkyl, $C_1$–$C_4$ haloalkyl, $C_1$–$C_4$ alkoxycarbonyl, —$CO_2H$, $C_1$–$C_4$ alkylcarbonyloxy, $C_1$–$C_4$ alkylcarbonyl;

$R^{13}$ is independently selected from:

H;

heterocycle substituted with 0–3 $R^{11A}$ and 0–1 $R^{16}$;

phenyl substituted with 0–3 $R^{11A}$;

benzyl substituted with 0–3 $R^{11A}$;

$C_1$–$C_6$ alkyl substituted with 0–3 $R^{11A}$;

$C_2$–$C_4$ alkenyl substituted with 0–3 $R^{11A}$;

$C_1$–$C_6$ alkylcarbonyl substituted with 0–3 $R^{11A}$;

$C_1$–$C_6$ alkoxycarbonyl substituted with 0–3 $R^{11A}$;

$C_1$–$C_6$ alkylaminocarbonyl substituted with 0–3 $R^{11A}$;

$C_3$–$C_6$ alkoxyalkyl substituted with 0–3 $R^{11A}$;

an amine protecting group when $R^{13}$ is bonded to N;

a hydroxyl or carboxyl protecting group when $R^{13}$ is bonded to O;

$R^{14}$ is independently selected from:

hydrogen, $C_1$–$C_6$ alkoxy, $C_2$–$C_6$ alkenyl, phenyl, benzyl, an amine protecting group when $R^{14}$ is bonded to N, a hydroxyl or carboxyl protecting group when $R^{14}$ is bonded to O; and $C_1$–$C_6$ alkyl substituted with 0–3 groups selected from OH, $C_1$–$C_4$ alkoxy, halogen, $R^{13}$ and $R^{14}$ can alternatively join to form —$(CH_2)_4$—, —$(CH_2)_5$—, —$CH_2CH_2N(R^{15})CH_2CH_2$—, or —$CH_2CH_2OCH_2CH_2$—;

$R^{13A}$ and $R^{14A}$ are independently selected from: H, $C_1$–$C_6$ alkyl;

$R^{13A}$ and $R^{14A}$ can alternatively join to form —$(CH_2)_4$—, —$(CH_2)_5$—, —$CH_2CH_2N(R^{15})CH_2CH_2$—, or —$CH_2CH_2OCH_2CH_2$—;

$R^{15}$ is H or $CH_3$;

$R^{16}$ is independently selected from:

halogen, —CN, —$NO_2$, $C_1$–$C_4$ haloalkyl, $C_1$–$C_4$ haloalkoxy, $C_1$–$C_4$ alkoxy, $C_1$–$C_6$ alkyl, $C_2$–$C_4$ alkenyl, $C_2$–$C_4$ alkynyl, phenethyl, phenoxy, $C_3$–$C_{10}$ cycloalkyl, $C_3$–$C_6$ cycloalkylmethyl, $C_7$–$C_{10}$ arylalkyl, $C_2$–$C_6$ alkoxyalkyl, $C_1$–$C_4$ alkylcarbonyloxy, $C_1$–$C_4$ alkylcarbonyl, benzyloxy, $C_3$–$C_6$ cycloalkoxy, or phenyl, said phenyl being optionally substituted with Cl, F, Br, CN, $NO_2$, $CF_3$, $C_1$–$C_4$ alkyl, $C_1$–$C_4$ alkoxy or OH, or alternately, $R^{11A}$ and $R^{16}$, when substituents on adjacent carbons, can be taken together with the carbon atoms to which they are attached to form a 5-6 membered carbocyclic or heterocyclic ring system, said carbocyclic or heterocyclic ring system being optionally substituted with Cl, F, Br, CN, $NO_2$, $CF_3$, $C_1$–$C_4$ alkyl, $C_1$–$C_4$ alkoxy or OH;

$R^{20}$ and $R^{21}$ are independently selected from:
  $C_1-C_6$ alkyl substituted with 0–3 $R^{11}$;
  $C_3-C_6$ alkoxyalkyl substituted with 0–3 $R^{11}$;
  $C_1-C_6$ alkylcarbonyl substituted with 0 –3 $R^{11}$;
  $C_1-C_6$ alkoxycarbonyl substituted with 0–3 $R^{11}$;
  $C_1-C_6$ alkylaminocarbonyl substituted with 0–3 $R^{11}$;
  benzoyl substituted with 0–3 $R^{12}$;
  phenoxycarbonyl substituted with 0–3 $R^{12}$;
  phenylaminocarbonyl substituted with 0–3 $R^{12}$;
  a hydroxyl protecting; or
  any group that, when administered to a mammalian subject, cleaves to form a free hydroxyl group;

$R^{20}$ and $R^{21}$ may also be taken together along with the oxygen atoms to which they are attached to form a group selected from the group consisting of:
  —O—C(—CH$_2$CH$_2$CH$_2$CH$_2$CH$_2$—)—O—,
  —O—C(CH$_2$CH$_3$)$_2$—O—, —O—C(CH$_3$)(CH$_2$CH$_3$)—O—, —O—C(CH$_2$CH$_2$CH$_2$CH$_3$)$_2$—O—,
  —O—C(CH$_3$)(CH$_2$CH(CH$_3$)CH$_3$)—O—,
  —O—CH(phenyl)—O—, —OCH$_2$SCH$_2$O—,
  —OCH$_2$OCH$_2$O—, —OS(=O)O—, —OC(=O)O—,
  —OCH$_2$O—, —OC(=S)O—, —OS(=O)$_2$O—,
  —OC(=O)C(=O)O—, —OC(CH$_3$)$_2$O—, and
  —OC(OCH$_3$)(CH$_2$CH$_2$CH$_3$)O—;

m is 0, 1 or 2;

$R^{22}$ is selected from the following:
  $C_1-C_8$ alkyl substituted with 0–3 $R^{31}$;
  $C_2-C_8$ alkenyl substituted with 0–3 $R^{31}$;
  $C_2-C_8$ alkynyl substituted with 0–3 $R^{31}$;
  a $C_3-C_{14}$ carbocyclic ring system substituted with 0–5 $R^{31}$ and 0–5 $R^{32}$;
  a 5- to 10-membered heterocyclic ring system containing 1 to 4 heteroatoms independently selected from oxygen, nitrogen or sulfur, said heterocyclic ring system being substituted with 0–2 $R^{32}$;

$R^{23}=R^{22}$;

$R^{31}$ is selected from one or more of the following:
  —OH, $C_1-C_4$ alkoxy, —CO$_2$R$^{15}$, —COR$^{15}$, keto, halogen, cyano, —CH$_2$NR$^{13}$R$^{14}$, —NR$^{13}$R$^{14}$, —CO$_2$R$^{13}$, —C(=O)R$^{11}$, —OC(=O)R$^{13}$, —OR$^{13}$, $C_2-C_6$ alkoxyalkyl, —S(O)$_m$R$^{13}$, —NHC(=NH)NHR$^{13}$, —C(=NH)NHR$^{13}$, —C(=O)NR$^{13}$R$^{14}$, —NR$^{14}$C(=O)R$^{13}$, =NOR$^{14}$, —NR$^{14}$C(=O)OR$^{14}$, —OC(=O)NR$^{13}$R$^{14}$, —NR$^{13}$C(=O)NR$^{13}$R$^{14}$, —NR$^{13}$C(=S)NR$^{13}$R$^{14}$, —NR$^{14}$SO$_2$NR$^{13}$R$^{14}$, —NR$^{14}$SO$_2$R$^{13}$, —SO$_2$NR$^{13}$R$^{14}$, $C_1-C_4$ alkyl, $C_2-C_4$ alkenyl, $C_3-C_{10}$ cycloalkyl, $C_3-C_6$ cycloalkylmethyl, benzyl, phenethyl, phenoxy, benzyloxy, nitro, $C_7-C_{10}$ arylalkyl, hydroxamic acid, hydrazide, oxime, boronic acid, sulfonamide, formyl, $C_3-C_6$ cycloalkoxy, $C_1-C_4$ alkyl substituted with —NR$^{13}$R$^{14}$, $C_1-C_4$ hydroxyalkyl, methylenedioxy, ethylenedioxy, $C_1-C_4$ haloalkyl, $C_1-C_4$ haloalkoxy, $C_1-C_4$ alkoxycarbonyl, $C_1-C_4$ alkylcarbonyloxy, $C_1-C_4$ alkylcarbonyl, $C_1-C_4$ alkylcarbonylamino, —OCH$_2$CO$_2$R$^{13}$, 2-(1-morpholino)ethoxy, azido, —C(R$^{14}$)=N(OR$^{14}$); or
  a $C_5-C_{14}$ carbocyclic residue substituted with 0–5 $R^{32}$; or
  a 5- to 10-membered heterocyclic ring system containing 1 to 4 heteroatoms independently selected from oxygen, nitrogen or sulfur, said heterocyclic ring system being substituted with 0–2 $R^{32}$;

$R^{32}$, when a substituent on carbon, is selected from one or more of the following:
  phenethyl, phenoxy, $C_3-C_{10}$ cycloalkyl, $C_3-C_6$ cycloalkylmethyl, $C_7-C_{10}$ arylalkyl, hydrazide, oxime, boronic acid, $C_2-C_6$ alkoxyalkyl, methylenedioxy, ethylenedioxy, $C_1-C_4$ alkylcarbonyloxy, —NHSO$_2$R$^{14}$, benzyloxy, halogen, 2-(1-morpholino)ethoxy, —CO$_2$R$^{13}$, hydroxamic acid, —CONR$^{13}$NR$^{13}$R$^{14}$, cyano, sulfonamide, —CHO, $C_3-C_6$ cycloalkoxy, —NR$^{13}$R$^{14}$, —C(R$^{14}$)=N(OR$^{14}$), —NO$_2$, —OR$^{13}$, —NR$^{40}$R$^{41}$, —SO$_m$R$^{13}$, —SO$_m$NR$^{13}$R$^{14}$, —C(=O)NR$^{13}$R$^{14}$, —OC(=O)NR$^{13}$R$^{14}$, —C(=O)R$^{11}$, —OC(=O)R$^{11}$, —B(OH)$_2$, —OCO$_2$R$^{13}$, phenyl, —C(=O)NR$^{13}$—(C$_1$-C$_4$ alkyl)—NR$^{13}$R$^{14}$, —C(=O)NR$^{40}$R$^{41}$, $C_1-C_4$ haloalkyl, $C_1-C_4$ haloalkoxy, $C_2-C_4$ haloalkenyl, $C_1-C_4$ haloalkynyl; or
  —C(=O)NR$^{13}$C(R$^{11}$)$_2$NR$^{13}$R$^{14}$,
  —C(=O)NR$^{13}$C(R$^{11}$)$_2$NR$^{13}$CO$_2$R$^{13}$,
  —C(=O)NR$^{13}$—(C$_1$-C$_4$ alkyl)—NR$^{13}$CO$_2$R$^{13}$,
  —C(=O)N(R$^{13}$)—(C$_1$-C$_4$ alkyl)—R$^{11}$,
  —C(=O)C(R$^{11}$)$_2$NR$^{13}$R$^{14}$,
  —C(=O)C(R$^{11}$)$_2$NR$^{13}$CO$_2$R$^{13}$, —C(=O)—(C$_1$-C$_4$ alkyl)—NR$^{13}$R$^{14}$, —C(=O)—(C$_1$-C$_4$ alkyl)—NR$^{13}$CO$_2$R$^{13}$; or
  —(CH$_2$)$_p$OR$^{13}$, —(CH$_2$)$_p$NHR$^{13}$, —(CH$_2$)$_p$CONHR$^{13}$, —(CH$_2$)$_p$SO$_2$NHR$^{13}$, —(CH$_2$)$_n$NHCOR$^{13}$, —(CH$_2$)$_p$NHHCO$_2$R$^{13}$, —(CH$_2$)$_n$OCONHR$^{13}$, —(CH$_2$)$_p$NHCONHR$^{13}$, —(CH$_2$)$_n$C(=NH)NHR$^{13}$; or
  $C_1-C_4$ alkoxy substituted with 0–4 groups selected from: $R^{11}$, $C_3-C_6$ cycloalkyl, —CO$_2$R$^{13}$, —C(=O)NR$^{13}$R$^{14}$, —NR$^{13}$R$^{14}$ or OH; or
  $C_1-C_4$ alkyl substituted with 0–4 groups selected from: $R^{11}$, =NR$^{14}$, =NNR$^{13}$C(=O)NR$^{13}$R$^{14}$, =NNR$^{13}$C(=O)OR$^{13}$, or —NR$^{13}$R$^{14}$; or
  $C_2-C_4$ alkenyl substituted with 0–4 $R^{11}$, $C_2-C_4$ alkynyl substituted with 0–4 $R^{11}$; or
  a 5- or 6-membered heterocyclic ring containing from 1 to 4 heteroatoms independently selected from oxygen, nitrogen or sulfur, substituted with 0–2 $R^{12}$; or
  or $R^{32}$ may be a 3- or 4- carbon chain attached to adjacent carbons on the ring to form a fused 5- or 6-membered ring, said 5- or 6- membered ring being optionally substituted on the aliphatic carbons with halogen, $C_1-C_4$ alkyl, $C_1-C_4$ alkoxy, hydroxy, or —NR$^{13}$R$^{14}$;
  or, when $R^{32}$ is attached to a saturated carbon, it may be =O, =S, =NOH;
  or when $R^{32}$ attached to sulfur it may be =O;

p is 0, 1, or 2
n is 1 or 2;

$R^{32}$, when a substituent on nitrogen, is selected from one or more of the following:
  phenyl, benzyl, phenethyl, hydroxy, $C_1-C_4$ hydroxyalkyl, $C_1-C_4$ alkoxy, $C_1-C_4$ alkyl, $C_3-C_6$ cycloalkyl, $C_3-C_6$ cycloalkylmethyl, —CH$_2$NR$^{13}$R$^{14}$, —NR$^{13}$R$^{14}$, $C_2-C_6$ alkoxyalkyl, $C_1-C_4$ haloalkyl, $C_1-C_4$ alkoxycarbonyl, —CO$_2$H, $C_1-C_4$ alkylcarbonyloxy, $C_1-C_4$ alkylcarbonyl, —C(R$^{14}$)=N(OR$^{14}$);

$R^{40}$ is selected from: H, $C_1-C_3$ alkyl; and
$R^{41}$ is selected from:
  —C(=O)NR$^{13}$R$^{14}$;
  —C(=O)NR$^{13}$NR$^{13}$R$^{14}$;
  —C(=O)C(R$^{11}$)$_2$NR$^{13}$R$^{14}$;
  —C(=O)C(R$^{11}$)$_2$NR$^{13}$NR$^{13}$R$^{14}$;
  —C(=O)C(R$^{11}$)$_2$NR$^{13}$CO$_2$R$^{13}$;
  —C(=O)H;
  —C(=O)R$^{11}$;
  —C(=O)—(C$_1$-C$_4$ alkyl)—NR$^{13}$R$^{14}$;

—C(=O)—(C$_1$–C$_4$ alkyl)—NR$^{13}$CO$_2$R$^{13}$;

1–3 amino acids linked together via amide bonds, and linked to the N atom via the carboxylate terminus;

provided that functional groups in R$^4$, R$^7$, R$^{22}$ and R$^{23}$, including but not limited to, amines, carboxyls, ketones, aldehydes, hydrazines, guanidines, hydroxamic acids, alcohols, oximes, and thiols, that are reactive in steps (1) and (2) of the present process are protected such that the protecting groups may be removed or the functional groups may be converted to other functional groups in accordance with step (3) below of this process;

said process comprising one or more of the steps of:

step (1): secondary amine formation: contacting an amine of formula (I):

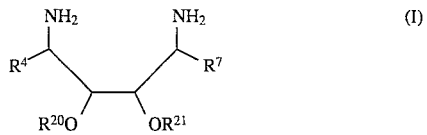

in a suitable solvent with at least about two molar equivalents of an aldehyde, said aldehyde being R$^{22}$—CHO or R$^{23}$—CHO, where R$^{22}$ and R$^{23}$ are as defined above, in the presence of at least about one molar equivalent of an acid and at least about two molar equivalents of a suitable imine reducing agent for a period of time sufficient to form a compound of formula (II):

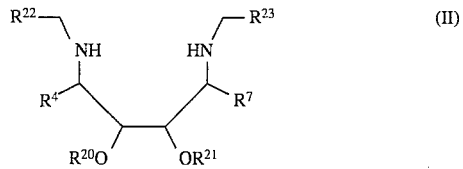

which is isolated; and step (2): cyclic urea formation: contacting the secondary amine of formula (II) in a suitable aprotic solvent at a suitable temperature in the presence of at least about one molar equivalent of a hindered amine base with at least about 0.3 molar equivalents of a suitable cyclizing agent at a suitable rate and for a period of time sufficient to form a compound of formula (III):

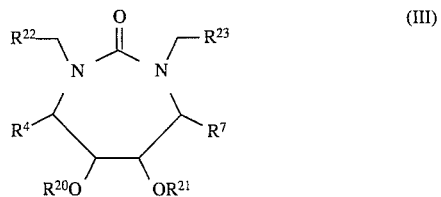

which is optionally carried through without isolation to step (3); and step (3): formation of compound (IV): contacting the cyclic urea of formula (III) in a suitable solvent with one or more reagents and/or conditions and/or a combination thereof for a period of time sufficient to effect the deprotection of the diol group (i.e., conversion of R$^{20}$ and R$^{21}$ to H) and the deprotection and/or conversion of functional groups in R$^4$, R$^7$, R$^{22}$ and R$^{23}$ to the form the desired functional groups in substituents R$^4$, R$^7$, R$^{22}$ and R$^{23}$ to form the desired compound of formula (IV).

The methods of the present invention may be generally represented by Scheme 7.

Scheme 7

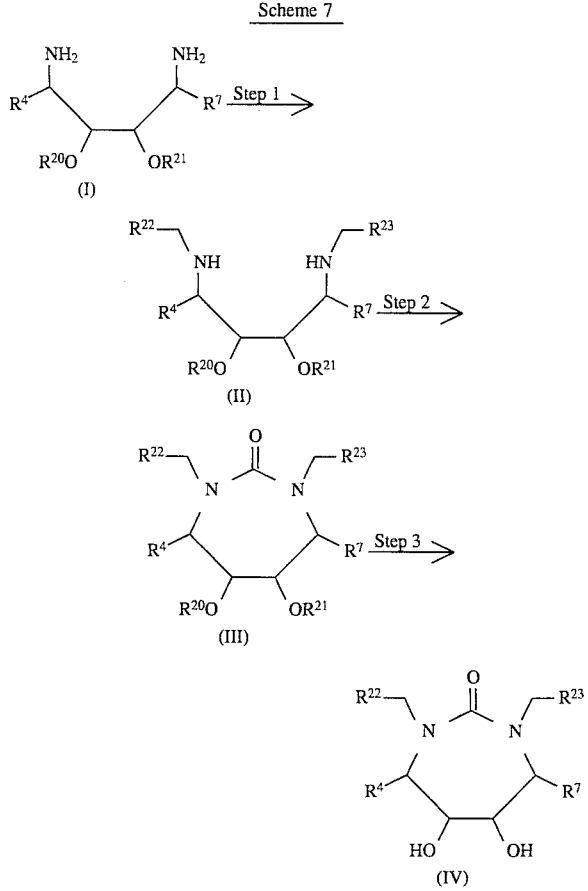

[2] Preferred in the present invention is a process as described above wherein:

R$^4$ and R$^7$ are independently selected from the following groups:

C$_1$–C$_8$ alkyl substituted with 0–3 R$^{11}$;
C$_2$–C$_8$ alkenyl substituted with 0–3 R$^{11}$;

R$^{11}$ is selected from one or more of the following:

H, keto, halogen, cyano, —CH$_2$NR$^{13}$R$^{14}$, —NR$^{13}$R$^{14}$, —CO$_2$R$^{13}$, —OC(=O)R$^{13}$, —OR$^{13}$, —S(O)$_m$R$^{13}$, C$_2$–C$_4$ alkenyl, C$_3$–C$_6$ cycloalkylmethyl, C$_3$–C$_{10}$ cycloalkyl substituted with 0–2 R$^{12}$, C$_1$–C$_4$ alkyl substituted with 0–2 R$^{12}$, aryl(C$_1$–C$_3$ alkyl)-, substituted with 0–2 R$^{12}$, a C$_5$–C$_{14}$ carbocyclic residue substituted with 0–3 R$^{12}$;

a 5- to 10-membered heterocyclic ring system containing 1 to 4 heteroatoms independently selected from oxygen, nitrogen or sulfur, said heterocyclic ring system being substituted with 0–3 R$^{12}$;

R$^{11A}$ is selected from one or more of the following:

H, keto, halogen, Cyano, —CH$_2$N(R$^{13A}$)R$^{(14A)}$, —OR$^{13A}$, —N(R$^{13A}$)R$^{(14A)}$, C$_2$–C$_4$ alkenyl, C$_3$–C$_6$ cycloalkylmethyl, C$_3$–C$_{10}$ cycloalkyl substituted with 0–2 R$^{12A}$, C$_1$–C$_4$ alkyl substituted with 0–2 R$^{12A}$, aryl(C$_1$–C$_3$ alkyl)— substituted with 0–2 R$^{12A}$;

NO$_2$, C$_1$–C$_6$ alkyl, or phenyl, said phenyl being optionally substituted with Cl, F, Br, CN, NO$_2$, CF$_3$, OCH$_3$ or OH;

a 5- to 10-membered heterocyclic ring system containing 1 to 4 heteroatoms independently selected from oxygen, nitrogen or sulfur, said heterocyclic ring system substituted with 0–3 R$^{12A}$.

$R^{12}$, when a substituent on carbon, is selected from one or more of the following:

phenyl, benzyl, phenethyl, benzyloxy, halogen, nitro, cyano, $C_1$–$C_4$ alkyl, $C_3$–$C_6$ cycloalkyl, $C_3$–$C_6$ cycloalkylmethyl, $C_7$–$C_{10}$ arylalkyl, $C_1$–$C_4$ alkoxy, formyl, $C_3$–$C_6$ cycloalkoxy, —$OR^{13}$, $C_2$–$C_6$ alkoxyalkyl optionally substituted with —$Si(CH_3)_3$, $C_1$–$C_4$ hydroxyalkyl, methylenedioxy, ethylenedioxy, —$S(O)_mR^{13}$, $CF_3$, 2-(1-morpholino)ethoxy, —$CO_2H$, hydroxamic acid, hydrazide, —$C(R^{14})=N(OR^{14})$, sulfonamide; or a 5- or 6-membered heterocyclic ring containing from 1 to 4 heteroatoms independently selected from oxygen, nitrogen or sulfur.

$R^{12}$, when a substituent on nitrogen, is selected from one or more of the following:

benzyl or methyl;

$R^{12A}$, when a substituent on carbon, is selected from one or more of the following: phenyl, benzyl, phenethyl, benzyloxy, halogen, nitro, cyano, $C_1$–$C_4$ alkyl, $C_3$–$C_6$ cycloalkyl, $C_3$–$C_6$ cycloalkylmethyl, $C_7$–$C_{10}$ arylalkyl, $C_1$–$C_4$ alkoxy, formyl, $C_3$–$C_6$ cycloalkoxy, —$OR^{13A}$, $C_2$–$C_6$ alkoxyalkyl optionally substituted with —$Si(CH_3)_3$, —$S(O)_m$Me; or a 5- or 6-membered heterocyclic ring containing from 1 to 4 heteroatoms independently selected from oxygen, nitrogen or sulfur.

$R^{12A}$, when a substituent on nitrogen, is selected from one or more of the following:

phenyl, benzyl, phenethyl, $C_1$–$C_4$ alkoxy, $C_1$–$C_4$ alkyl, $C_3$–$C_6$ cycloalkyl, $C_3$–$C_6$ cycloalkylmethyl, $C_2$–$C_6$ alkoxyalkyl, $C_1$–$C_4$ alkoxycarbonyl, $C_1$–$C_4$ alkylcarbonyloxy, $C_1$–$C_4$ alkylcarbonyl, $CF_3$, 2-(1-morpholino)ethoxy, —$CO_2H$, hydroxamic acid, hydrazide, —$C(R^{14}A)=N(OR^{14A})$, sulfonamide;

$R^{13}$ is independently selected from:

a heterocycle selected from the group consisting of:

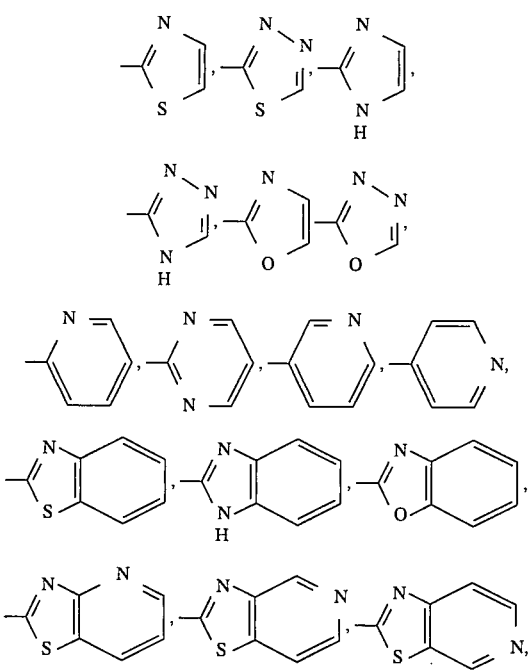

said heterocycle substituted with 0–3 $R^{11A}$ and 0–1 $R^{16}$;

H;

$C_1$–$C_6$ alkyl substituted with 0–3 $R^{11}$A;

$C_{3–C6}$ alkoxyalkyl substituted with 0–3 $R^{11}$A;

$C_2$–$C_4$ alkenyl substituted with 0–3 $R^{11}$A;

benzyl substituted with 0–3 $R^{11}$A;

an amine protecting group when $R^{13}$ is bonded to N;

a hydroxyl or carboxyl protecting group when $R^{13}$ is bonded to O;

$R^{14}$ is independently selected from:

hydrogen, $CF_3$, $C_1$–$C_6$ alkyl, $C_1$–$C_6$ alkoxy, $C_2$–$C_6$ alkenyl, benzyl, an amine protecting group when $R^{14}$ is bonded to N, a hydroxyl or carboxyl protecting group when $R^{14}$ is bonded to O;

$R^{13}$ and $R^{14}$ can alternatively join to form —$(CH_2)_4$—, —$(CH_2)_5$—, —$CH_2CH_2N(R^{15})CH_2CH_2$—, or —$CH_2CH_2OCH_2CH_2$—;

$R^{13A}$ and $R^{14A}$ are independently selected from: H, $C_1$–$C_6$ alkyl;

$R^{13A}$ and $R^{14A}$ can alternatively join to form —$(CH_2)_4$—, —$(CH_2)_5$—, —$CH_2CH_2N(R^{15})CH_2CH_2$—, or —$CH_2CH_2OCH_2CH_2$—;

$R^{15}$ is H or $CH_3$;

$R^{16}$ is independently selected from:

halogen, $NO_2$, CN, $C_1$–$C_6$ alkyl, or phenyl, said phenyl being optionally substituted with Cl, F, Br, CN, $NO_2$, $CF_3$, $OCH_3$ or OH;

$R^{20}$ and $R^{21}$ are independently selected from:

$C_3$–$C_6$ alkoxyalkyl substituted with 0–3 $R^{11}$;

$C_1$–$C_6$ alkoxycarbonyl substituted with 0–3 $R^{11}$;

phenoxycarbonyl substituted with 0–3 $R^{12}$;

a hydroxyl protecting; or any group that, when administered to a mammalian subject, cleaves to form a free hydroxyl group;

$R^{20}$ and $R^{21}$ may also be taken together along with the oxygen atoms to which they are attached to form a group selected from the group consisting of:

—O—(—$CH_2CH_2CH_2CH_2CH_2$—)—O—,

—O—$C(CH_2CH_3)_2$—O—,     —O—

$C(CH_3)(CH_2CH_3)$—O—,
—O—$C(CH_2CH_2CH_2CH_3)_2$—O—, —O—$C(CH_3)(CH_2CH(CH_3)CH_3)$—O—, —O—CH(phenyl)—O—, —$OCH_2SCH_2O$—, —$OCH_2OCH_2O$—, —$OCH_2O$—, —$OC(CH_3)_2O$—, —$OC(OCH_3)$ $(CH_2CH_2CH_3)O$—, $R^{22}$ is selected from the following:

$C_1$–$C_8$ alkyl substituted with 0–3 $R^{31}$;

$C_2$–$C_8$ alkenyl substituted with 0–3 $R^{31}$;

$C_2$–$C_4$ alkynyl substituted with 0–3 $R^{31}$;

a $C_6$–$C_{10}$ aryl substituted with 0–3 $R^{31}$ and 0–3 $R^{32}$;

or a heterocycle selected from the group consisting of thiazole, indazole, thieno [2,3-c]pyrazole and thieno [3,2-c] pyrazole, said heterocycle substituted with 0–2 $R^{31}$;

$R^{23}$=$R^{22}$;

$R^{31}$ is selected from one or more of the following:

—OH, $C_1$–$C_4$ alkoxy, cyano, nitro, $C_1$–$C_4$ haloalkyl, $C_1$–$C_4$ haloalkoxy, —$CO_2R^{15}$, —$COR^{15}$, keto, halogen, —$CH_2NR^{13}R^{14}$, —$NR^{13}R^{14}$, —$OR^{13}$, $C_2$–$C_6$ alkoxyalkyl, $C_1$–$C_4$ alkyl, $C_2$–$C_4$ alkenyl, $C_3$–$C_{10}$ cycloalkyl, —$CO_2R^{13}$, —$S(O)_mR^{13}$;

a $C_5$–$C_{14}$ carbocyclic residue substituted with 0–5 $R^{32}$; or a 5- to 10-membered heterocyclic ring system containing 1 to 4 heteroatoms independently selected from oxygen, nitrogen or sulfur, said heterocyclic ring system being substituted with 0–2 $R^{32}$;

$R^{32}$, when a substituent on carbon, is selected from one or more of the following:

phenethyl, phenoxy, $C_3$–$C_{10}$ cycloalkyl, $C_3$–$C_6$ cycloalkylmethyl, $C_7$–$C_{10}$ arylalkyl, $C_2$–$C_6$ alkoxyalkyl, methylenedioxy, ethylenedioxy, $C_1$–$C_4$ alkylcarbonyloxy, —$NHSO_2R^{14}$, benzyloxy, halogen, 2-(1-morpholino)ethoxy, —$CO_2R^{13}$, —$CONR^{13}NR^{13}R^{14}$, cyano, sulfonamide, —CHO, $C_3$–$C_6$ cycloalkoxy, —$NR^{13}R^{14}$, —$NO_2$, —$OR^{13}$, —$NR^{40}R^{41}$, —$SO_mR^{13}$, —$SO_mNR^{13}R^{14}$, —$C(=O)NR^{13}R^{14}$, —$OC(=O)NR^{13}R^{14}$, —$C(=O)R^{11}$, —$OC(=O)R^{11}$, —$OCO_2R^{13}$, phenyl, —$C(=O)NR^{13}$—($C_1$–$C_4$ alkyl)—$NR^{13}R^{14}$, —$C(=O)NR^{40}R^{41}$, $C_1$–$C_4$ haloalkyl, $C_1$–$C_4$ haloalkoxy, $C_2$–$C_4$ haloalkenyl, $C_1$–$C_4$ haloalkynyl; or —$(CH_2)_pOR^{13}$, —$(CH_2)_pNHR^{13}$, —$(CH_2)_pCONHR^{13}$, —$(CH_2)_pSO_2NHR^{13}$, —$(CH_2)_nOCONHR^{13}$, —$(CH_2)_pNHCONHR^{13}$, $(CH_2)_pC(=NH)NHR^{13}$; or —$C(=O)C(R^{11})_2NR^{13}R^{14}$;
—$C(=O)C(R^{11})_2NR^{13}CO_2^{R13}$;
—$C(=O)C(R^{11})_2NR^{13}CO_2R^{13}$; —$C(=O)$—($C_1$–$C_4$ alkyl)—$NR^{13}R^{14}$; —$C(=O)$—($C_1$–$C_4$ alkyl)—$NR^{13}CO_2R^{13}$; or $C_1$–$C_4$ alkoxy substituted with 0–4 groups selected from: $R^{11}$, $C_3$–$C_6$ cycloalkyl, —$CO_2R^{13}$, —$C(=O)NR^{13}R^{14}$, or —$NR^{13}R^{14}$; or $C_1$–$C_4$ alkyl substituted with 0–4 groups selected from: $R^{11}$, =$NR^{14}$, =$NNR^{13}C(=O)NR^{13}R^{14}$, or —$NR^{13}R^{14}$; or $C_2$–$C_4$ alkenyl substituted with 0–4 $R^{11}$, $C_2$–$C_4$ alkynyl substituted with 0–3 $R^{11}$; or a 5- or 6-membered heterocyclic ring containing from 1 to 4 heteroatoms independently selected from oxygen, nitrogen or sulfur, substituted with 0–2 $R^{12}$;

$R^{32}$, when a substituent on nitrogen, is selected from one or more of the following:

phenyl, benzyl, phenethyl, hydroxy, $C_1$–$C_4$ alkyl, $C_3$–$C_6$ cycloalkyl, $C_3$–$C_6$ cycloalkylmethyl, —$CH_2NR^{13}R^{14}$, —$NR^{13}R^{14}$, $C_2$–$C_6$ alkoxyalkyl, $C_1$–$C_4$ alkoxycarbonyl, $C_1$–$C_4$ alkylcarbonyloxy, $C_1$–$C_4$ alkyl carbonyl;

$R^{40}$ is selected from: H, $C_1$–$C_3$ alkyl; and $R^{41}$ is selected from:

—$C(=O)$ $NR^{13}R^{14}$;
$C(=O)$ $NR^{13}NR^{13}R^{14}$;
—$C(=O)C(R^{11})_2NR^{13}R^{14}$;
—$C=O)C(R^{11})_2NR^{13}NR^{13}R^{14}$;
—$C(=O)C(R^{11})_2NR^{13}CO_2R^{13}$;
—$C(=O)H$;
—$C(=O)$ $R^{11}$;
—$C(=O)$—($C_1$–$C_4$ alkyl)—$NR^{13}R^{14}$;
—$C(=O)$—($C_1$–$C_4$ alkyl)—$NR^{13}CO_2R^{13}$;

1–3 amino acids linked together via amide bonds, and linked to the N atom via the carboxylate terminus.

[3] More preferred in the present invention is a process as described above wherein:

$R^4$ and $R^7$ are independently selected from the following groups:

$C_1$–$C_8$ alkyl substituted with 0–2 $R^{11}$;

$R^{11}$ is selected from one or more of the following:

H, halogen, —$OR^{13}$, $C_3$–$C_{10}$ cycloalkyl substituted with 0–2 $R^{12}$, $C_1$–$C_4$ alkyl substituted with 0–2 $R^{12}$, aryl($C_1$–$C_3$alkyl)— substituted with 0–2 $R^{12}$; aryl substituted with 0–2 $R^{12}$;

a heterocyclic ring system selected from pyridyl, pyrimidinyl, triazinyl, furanyl, thienyl, pyrrolyl, pyrazolyl, imidazolyl, tetrazolyl, benzofuranyl, indolyl, quinolinyl, isoquinolinyl, oxazolidinyl, said heterocyclic ring system being substituted with 0–2 $R^{12}$;

$R^{11A}$ is selected from one or more of the following:

H, halogen, —$OR^{13A}$, $C_3$–$C_{10}$ cycloalkyl substituted with 0–2 $R^{12A}$, $C_1$–$C_4$ alkyl substitued with 0–2 $R^{12A}$, aryl($C_1$–$C_3$ alkyl)- substituted with 0–2 $R^{12A}$, aryl substituted with 0–2 $R^{12A}$; or $NO_2$, cyano, $C_1$–$C_6$ alkyl, or phenyl, said phenyl being optionally substituted with Cl, F, Br, CN, $NO_2$, $CF_3$, $OCH_3$ or OH; or a heterocyclic ring system selected from pyridyl, pyrimidinyl, triazinyl, furanyl, thienyl, pyrrolyl, pyrazolyl, imidazolyl, tetrazolyl, benzofuranyl, indolyl, quinolinyl, isoquinolinyl, oxazolidinyl, said heterocyclic ring system being substituted with 0–2 $R^{12A}$;

$R^{12}$, when a substituent on carbon, is selected from one or more of the following:

benzyloxy, halogen, methyl, nitro, cyano, $C_3$–$C_6$ cycloalkyl, $C_3$–$C_6$ cycloalkylmethyl, $C_7$–$C_{10}$ arylalkyl, $C_1$–$C_4$ alkoxy, formyl, $C_3$–$C_6$ cycloalkoxy, —$OR^{13}$, $C_2$–$C_6$ alkoxyalkyl optionally substituted with —$Si(CH_3)_3$, —$S(O)_m$Me, $CF_3$, 2-(1-morpholino)ethoxy, hydroxamic acid, hydrazide, —$C(R^{14})=N(OR^{14})$, sulfonamide;

$R^{12}$, when a substituent on nitrogen, is methyl;

$R^{12A}$, when a substituent on carbon, is selected from one or more of the following:

benzyloxy, halogen, methyl, nitro, cyano, $C_3$–$C_6$ cycloalkyl, $C_3$–$C_6$ cycloalkylmethyl, $C_7$–$C_{10}$ arylalkyl, $C_1$–$C_4$ alkoxy, formyl, $C_3$–$C_6$ cycloalkoxy, —$OR^{13A}$, $C_2$–$C_6$ alkoxyalkyl optionally substituted with —$Si(CH_3)_3$, —$S(O)_m$Me, $CF_3$, 2-(1-morpholino)ethoxy, —$CO_2H$, hydroxamic acid, hydrazide, —$C(R^{14A})=N(OR^{14A})$, sulfonamide; or $R^{12A}$, when a substituent on nitrogen, is selected from one or more of the following:

benzyl or methyl;

$R^{13}$ is independently selected from the group consisting of:
a heterocycle selected from the group consisting of:

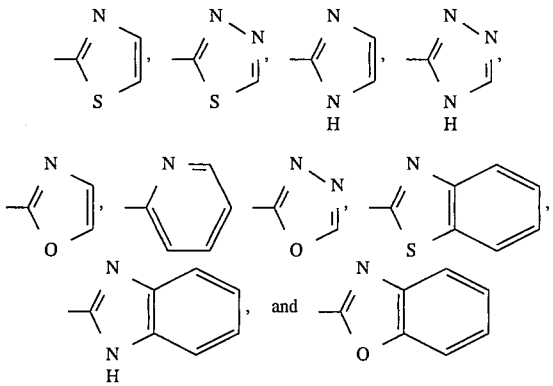

said heterocycle substituted with 0–1 $R^{114}$ and 0–1 $R^{16}$;

H, $C_1$–$C_4$ alkyl, $C_2$–$C_4$ alkenyl, benzyl, an amine protecting group when $R^{13}$ is bonded to N, and a hydroxyl or carboxyl protecting group when $R^{13}$ is bonded to O;

$R^{14}$ is independently selected from the group consisting of:
hydrogen, $CF_3$, $C_1$–$C_4$ alkyl, $C_1$–$C_4$ alkoxy, $C_2$–$C_4$ alkenyl, benzyl, an amine protecting group when $R^{14}$ is bonded to N, a hydroxyl or carboxyl protecting group when $R^{14}$ is bonded to O;

$R^{13}$ and $R^{14}$ can alternatively join to form —$(CH_2)_4$—, —$(CH_2)_5$—, —$CH_2CH_2N(R^{15})CH_2CH_2$—, or —$CH_2CH_2OCH_2CH_2$—;

$R^{13A}$ and $R^{14A}$ are independently selected from: H, $C_1$–$C_6$ alkyl;

$R^{13A}$ and $R^{14A}$ can alternatively join to form —$(CH_2)_4$—, —$(CH_2)_5$—, —$CH_2CH_2N(R^{15})CH_2CH_2$—, or —$CH_2CH_2OCH_2CH_2$—;

$R^{15}$ is H or $CH_3$;

$R^{16}$ is independently selected from:
halogen, $NO_2$, CN, $C_1$–$C_6$ alkyl, or phenyl, said phenyl being optionally substituted with Cl, F, Br, CN, $NO_2$, $CF_3$, $OCH_3$ or OH;

$R^{20}$ and $R^{21}$ are taken together along with the oxygen atoms to which they are attached to form a group selected from the group consisting of:
—O—C(—$CH_2CH_2CH_2CH_2CH_2$—)—O—,
—O—C($CH_2CH_3$)$_2$—O—, —$OCH_2OCH_2O$—,
—$OCH_2O$—, and —$OC(CH_3)_2O$—;

$R^{22}$ is selected from the following:
$C_1$–$C_8$ alkyl substituted with 0–2 $R^{31}$;
$C_2$–$C_6$ alkenyl substituted with 0–2 $R^{31}$;
phenyl substituted with 0–2 $R^{31}$ and 0–2 $R^{32}$;
or a heterocycle selected from the group consisting of thiazole, indazole, thieno[2,3-c]pyrazole and thieno[3,2-c]pyrazole, said heterocycle substituted with 0–2 $R^{31}$;

$R^{23}$=$R^{22}$;

$R^{31}$ is selected from one or more of the following:
—OH, —$OCH_3$, cyano, nitro, $CF_3$, $C_1$–$C_4$ haloalkoxy, —$CO_2R^{15}$, —$COR^{15}$, halogen, —$OR^{13}$, $C_1$–$C_4$ alkyl, $C_3$–$C_{10}$ cycloalkyl, —$CO_2R^{13}$, —$S(O)_mR^{13}$;
aryl substituted with 0–3 $R^{32}$; or
a heterocyclic ring system chosen from pyridyl, pyrimidinyl, triazinyl, furanyl, thienyl, pyrrolyl, pyrazolyl, imidazolyl, tetrazolyl, benzofuranyl, indolyl, quinolinyl, isoquinolinyl, oxazolidinyl, benzimidazolyl, benzotriazolyl, indazolyl, benzoxazolinyl, benzoxazolyl, said heterocyclic ring being substituted with 0–2 $R^{32}$;

$R^{32}$, when a substituent on carbon, is selected from one or more of the following:
—$(CH_2)_pOR^{13}$, —$(CH_2)_pCONHR^{13}$, —$(CH_2)_nOCONHR^{13}$, —$(CH_2)_pNHCONHR^{13}$; or
—$CONH_2$, —$CO_2H$, —CHO, —$CH_2NHOH$, —$CH_2NR^{13}R^{14}$, —$NR^{13}R^{14}$ hydroxy hydroxymethyl —$C(R^{14})$=$N(OR^{14})$, halogen, methoxy, methyl, nitro, cyano, allyloxy, —$CO_2CH_3$, —NHCHO, —NHCOCH$_3$, —$OCO_2CH_3$, —CH=$NCH_2CH_2OH$, —$OCONHCH_2C_6H_5$, —$OCONHCH_3$, oxazolidinyl, —C≡C— $CH_2OH$, —$COCH_3$, hydroxyethyl, $C_1$–$C_3$ alkyl (said alkyl substituted with 0–4 halogen, or OH), tetrazolyl, —$OCH_2CONH_2$, —$CONHNH_2$, —CH=$NNHCONH_2$, —$CONHOCH_3$, —$CH_2CH(OH)CH_2OH$, adamantamido, hydroxyethoxy, dihydroxyethyl, —$C(NH_2)$=NH, —$CONHCH_3$, —$B(OH)_2$, benzyloxy, —$CONHCH_2CH_3$, —$CON(CH_2CH_3)_2$, methylthio, —$SO_2CH_3$, —$NHCONH_2$, —$NHCONHCH_3$, —$NHCOCH_2N(CH_3)_2$, —$NHCOCH_2NHCH_3$,
—$NHCOCH_2NHCO_2CH_2C_6H_5$, —$NHCOCH_2NH_2$, —$NHCOCH(CH_3)NHCO_2CH_2C_6H_5$,
—$NHCOCH(CH_2C_6H_5)NHCO_2CH_2C_6H_5$,— $NHCOCH(CH_3)NH_2$, —$NHCOCH(CH_2C_6H_5)NH_2$, —$CO_2CH_2CH_3$, —$CONHCH_2CH_3$, —$CONHCH(CH_3)_2$, —$CH_2$-imidazole, —$COC(CH_3)_3$, —$CH(OH)CF_3$, —CO-imidazole, —CO-pyrazolyl, oxadiazolidinonyl, —$COCF_3$, —$COCH_2CH_3$, —$COCH_2CH_3$, pyrazolyl, —$SO_2NH_2$, —$C(CH_2CH_3)$=N(OH), —$C(CF_3)$=N(OH), phenyl, acetoxy, hydroxyamino, —$N(CH_3)$ (CHO), cyclopropylmethoxy, —$CONR^{13}R^{14}$, —CONHOH, (diethylaminoethyl) aminocarbonyl, (N-ethyl,N-methylaminoethyl)aminocarbonyl,
(4-methylpiperazinylethyl)aminocarbonyl, (pyrrolidinylethyl)aminocarbonyl, (piperidinylethyl)aminocarbonyl, —$NHCOCH_2NHCH_3$, N-(2-(4-morpholino)ethyl)aminocarbonyl, N-(2-(N,N-dimethylamino)ethyl)aminocarbonyl;

p is 0; and $R^{32}$ when a substituent on nitrogen, is selected from one or more of the following:
benzyl or methyl.

[4] Further preferred in the present invention is a process as described above wherein:

$R^4$ and $R^7$ are independently $C_1$–$C_3$ alkyl substituted with 0–1 $R^{11}$;

$R^{11}$ is selected from one or more of the following:
H, halogen, —$OR^{13}$, $C_3$–$C_{10}$ cycloalkyl substituted with 0–2 $R^{12}$, $C_1$–$C_4$ alkyl substituted with 0–2 $R^{12}$, aryl($C_1$–$C_3$ alkyl)- substituted with 0–2 $R^{12}$; aryl substituted with 0–2 $R^{12}$;

a heterocyclic ring system selected from pyridyl, pyrimidinyl, triazinyl, furanyl, thienyl, pyrrolyl, pyrazolyl, imidazolyl, tetrazolyl, benzofuranyl, indolyl, quinolinyl, isoquinolinyl, oxazolidinyl, said heterocyclic ring system being substituted with 0–2 $R^{12}$;

$R^{114}$ is selected from one or more of the following:
H, halogen, —$OR^{13A}$, $C_3$–$C_{10}$ cycloalkyl substituted with 0–2 $R^{12A}$, $C_1$–$C_4$ alkyl substitued with 0–2 $R^{12A}$, aryl($C_1$–$C_3$ alkyl)- substituted with 0–2 $R^{12A}$, aryl substituted with 0–2 $R^{12}A$; or $NO_2$, cyano, $C_1$–$C_6$ alkyl, or phenyl, said phenyl being optionally substituted with Cl, F, Br, CN, $NO_2$, $CF_3$, $OCH_3$ or OH; or a heterocyclic ring system selected from pyridyl, pyrimidinyl, triazinyl, furanyl, thienyl, pyrrolyl, pyrazolyl, imidazolyl, tetrazolyl, benzofuranyl, indolyl, quinolinyl, isoquinolinyl, oxazolidinyl, said heterocyclic ring system being substituted with 0–2 $R^{12A}$;

$R^{12}$, when a substituent on carbon, is selected from one or more of the following:

benzyloxy, halogen, methyl, nitro, cyano, $C_3$–$C_6$ cycloalkyl, $C_3$–$C_6$ cycloalkylmethyl, $C_7$–$C_{10}$ arylalkyl, $C_1$–$C_4$ alkoxy, formyl, $C_3$–$C_6$ cycloalkoxy, —$OR^{13}$, $C_2$–$C_6$ alkoxyalkyl optionally substituted with —$Si(CH_3)_3$, —$S(O)_mMe$, $CF_3$, 2-(1-morpholino)ethoxy, hydroxamic acid, hydrazide, —$C(R^{14})=N(OR^{14})$, sulfonamide;

$R^{12}$, when a substituent on nitrogen, is methyl;

$R^{12A}$, when a substituent on carbon, is selected from one or more of the following:

benzyloxy, halogen, methyl, nitro, cyano, $C_3$–$C_6$ cycloalkyl, $C_3$–$C_6$ cycloalkylmethyl, $C_7$–$C_{10}$ arylalkyl, $C_1$–$C_4$ alkoxy, formyl, $C_3$–$C_6$ cycloalkoxy, —$OR^{13A}$, $C_2$–$C_6$ alkoxyalkyl optionally substituted with —$Si(CH_3)_3$, —$S(O)_mMe$, $CF_3$, 2-(1-morpholino)ethoxy, —$CO_2H$, hydroxamic acid, hydrazide, —$C(R^{14A})=N(OR^{14A})$, sulfonamide; or $R^{12A}$, when a substituent on nitrogen, is methyl;

$R^{13}$ is independently selected from the group consisting of:

a heterocycle selected from the group consisting of:

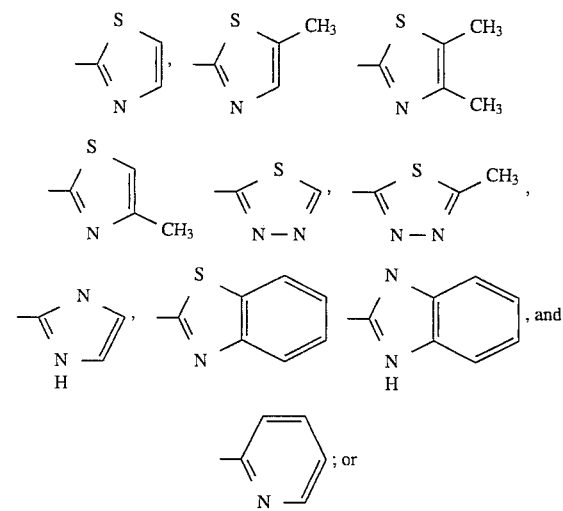

H, $C_1$–$C_4$ alkyl, $C_2$–$C_4$ alkenyl, benzyl, an amine protecting group when $R^{13}$ is bonded to N, and a hydroxyl or carboxyl protecting group when $R^{13}$ is bonded to O;

$R^{13}$ and $R^{14}$ can alternatively join to form —$(CH_2)_4$—, —$(CH_2)_5$—, —$CH_2CH_2N(R^{15})CH_2CH_2$—, or —$CH_2CH_2OCH_2CH_2$—;

$R^{13A}$ and $R^{14A}$ are independently selected from: H, $C_1$–$C_6$ alkyl;

$R^{13A}$ and $R^{14A}$ can alternatively join to form —$(CH_2)_4$—, —$(CH_2)_5$—, —$CH_2CH_2N(R^{15})CH_2CH_2$—, or —$CH_2CH_2OCH_2CH_2$—;

$R^{15}$ is H or $CH_3$; $R^{20}$ and $R^{21}$ are taken together along with the oxygen atoms to which they are attached to form a group selected from the group consisting of:

—O—$C(CH_2CH_3)_2$—O—, —$OCH_2OCH_2O$—, —$OCH_2O$—, and —$OC(CH_3)_2O$—;

$R^{22}$ is selected from the following:

$C_1$–$C_8$ alkyl substituted with 0–2 $R^{31}$;

phenyl substituted with 0–2 $R^{31}$ and 0–2 $R^{32}$;

or a heterocycle selected from the group consisting of thiazole, indazole, thieno [2,3-c]pyrazole and thieno [3,2-c]pyrazole, said heterocycle substituted with 0–2 $R^{31}$;

$R^{23}=R^{22}$;

$R^{31}$ is selected from one or more of the following:

—OH, —$OCH_3$, cyano, nitro, $CF_3$, $C_1$–$C_4$ haloalkoxy, —$CO_2R^{15}$, —$COR^{15}$, halogen, —$OR^{13}$, $C_1$–$C_4$ alkyl, $C_3$–$C_{10}$ cycloalkyl, —$CO_2R^{13}$, —$S(O)_mR^{13}$;

aryl substituted with 0–3 $R^{32}$; or a heterocyclic ring system chosen from pyridyl, pyrimidinyl, triazinyl, furanyl, thienyl, pyrrolyl, pyrazolyl, imidazolyl, tetrazolyl, benzofuranyl, indolyl, quinolinyl, isoquinolinyl, oxazolidinyl, benzimidazolyl, benzotriazolyl, indazolyl, benzoxazolinyl, benzoxazolyl, said heterocyclic ring being substituted with 0–2 $R^{32}$;

$R^{32}$, when a substituent on carbon, is selected from one or more of the following:

—$(CH_2)_pOR^{13}$, —$(CH_2)_pCONHR^{13}$, —$CONH_2$, —$CO_2H$, —CHO, —$CH_2NHOH$, —$CH_2NR^{13}R^{14}$, —$NR^{13}R^{14}$, hydroxy, hydroxymethyl, —$C(R^{14})=N(OR^{14})$, halogen, methoxy, methyl, nitro, cyano, allyloxy, —$CO_2CH_3$, —NHCHO, —NHCOCH_3, —$OCO_2CH_3$, —CH=$NCH_2CH_2OH$, —$OCONHCH_2C_6H_5$, —$OCONHCH_3$, oxazolidinyl, —C=C—$CH_2OH$, —$COCH_3$, hydroxyethyl, $C_1$–$C_3$ alkyl (said alkyl substituted with 0–4 halogen, or OH), tetrazolyl, —$OCH_2$ $CONH_2$, —$CONHNH_2$, —CH=$NNHCONH_2$, —$CONHOCH_3$, —$CH_2CH(OH)CH_2OH$, adamantamido, hydroxyethoxy, dihydroxyethyl, —$C(NH_2)=NH$, —$CONHCH_3$, —$B(OH)_2$, benzyloxy, —$CONHCH_2CH_3$, —$CON(CH_2CH_3)_2$, methylthio, —$SO_2CH_3$, —$NHCONH_2$, —$NHCONHCH_3$, —$NHCOCH_2N$ $(CH_3)_2$, —$NHCOCH_2NHCH_3$, —$NHCOCH_2NHCO_2CH_2C_6H_5$, —$NHCOCH_2NH_2$, —$NHCOCH(CH_3)NHCO_2CH_2C_6H_5$, —$NHCOCH(CH_2C_6H_5)NHCO_2CH_2C_6H_5$, —$NHCOCH(CH_3)NH_2$, —$NHCOCH(CH_2C_6H_5)NH_2$, —$CO_2CH_2CH_3$, —$CONHCH_2CH_2CH_3$, —$CONHCH(CH_3)_2$, —$CH_2$-imidazole, —$COC(CH_3)_3$, —$CH(OH)CF_3$, —CO-imidazole, —CO— pyrazolyl, oxadiazolidinonyl, —$COCF_3$, —$COCH_2CH_3$, —$COCH_2CH_2CH_3$, pyrazolyl, —$SO_2NH_2$, —$C(CH_2CH_3)=N(OH)$, —$C(CF_3)=N(OH)$, phenyl, acetoxy, hydroxyamino, —$N(CH_3)$ (CHO), cyclopropylmethoxy, —$CONR^{13}R^{14}$, —CONHOH, (diethylaminoethyl)aminocarbonyl, (N-ethyl,N-methylaminoethyl)aminocarbonyl, (4-methylpiperazinylethyl)aminocarbonyl, (pyrrolidinylethyl)aminocarbonyl, (piperidinylethyl)aminocarbonyl, —$NHCOCH_2NHCH_3$, N-(2-(4-morpholino)ethyl)aminocarbonyl, N-(2-(N,N-dimethylamino)ethyl) aminocarbonyl;

p is 0; and $R^{32}$ when a substituent on nitrogen, is methyl.

[5] Further preferred in the present invention is a process as described above wherein:

$R^4$ and $R^7$ are independently selected from:

benzyl, fluorobenzyl, pyrrolylmethyl, methoxybenzyl, isobutyl, nitrobenzyl, aminobenzyl, thienylmethyl, hydroxybenzyl, pyridylmethyl, naphthylmethyl, thiomethylbenzyl, thiazolylmethyl, 3,4-methylenedioxybenzyl, and N,N-dimethylaminobenzyl;

$R^{20}$ and $R^{21}$ are taken together along with the oxygen atoms to which they are attached to form a group selected from the group consisting of:

—OCH$_2$OCH$_2$O— and —OC(CH$_3$)$_2$O—;
R$^{22}$ is selected from the group consisting of:

allyl, methyl, ethyl, propyl, cyclopropyl, cyclopropylmethyl, n-butyl, i-butyl, CH$_2$CH=C(CH$_3$)$_2$, pyridinylmethyl, pyridinyl, methallyl, n-pentyl, i-pentyl, hexyl, phenyl, isoprenyl, propargyl, picolinyl, methoxymethyl, cyclohexyl, dimethylbutyl, ethoxymethyl, methyloxazolinylmethyl, naphthyl, methyloxazolinyl, vinyloxymethyl, pentafluorophenyl, quinolinyl, carboxyphenyl, chloro-thienyl, benzyloxyphenyl, biphenyl, adamantyl, cyclopropylmethoxyphenyl, methoxyphenyl, methylphenyl, ethoxyphenyl, hydroxyphenyl, hydroxymethylphenyl, aminophenyl, formylphenyl, cyanophenyl, cinnamyl, allyloxyphenyl, fluorophenyl, difluorophenyl, chlorophenyl, chloromethylphenyl, fluoromethylphenyl, iodophenyl, bromophenyl, cyclobutyl, formaldoximephenyl, cyclopentyl, nitrophenyl, (H$_2$NC(=O))-phenyl, carbomethoxyphenyl, carboethoxyphenyl, tetrazolylphenyl, dimethylallyl, aminomethylphenyl, (O-benzyl-formaldoxime)phenyl, (O-methylformaldoxime)phenyl, (CH$_3$O$_2$CO)-phenyl, (HOCH$_2$CH$_2$N=CH)-phenyl, N-benzylaminocarbonylphenyl, N-methylaminophenyl, N-ethylaminophenyl, N-ethylaminomethylphenyl, acetylphenyl, acetoxyphenyl, N-hydroxylaminophenyl, phenylmethylboronic acid, N-hydroxylaminomethylphenyl, (hydroxyl) ethylphenyl, (CH$_3$C (=NOH))-phenyl, (H$_2$NNHC (=O))-phenyl, (H$_2$NC (=O)NHN=CH)-phenyl, (CH$_3$ONHC(=O))-phenyl, (HONHC(=O))-phenyl, (CH$_3$NHC (=O))-phenyl, N,N-dimethylaminocarbonylphenyl, (HOCH$_2$CH(OH)CH$_2$O) phenyl, hydroxyethoxyphenyl (oxazolidinyl)-phenyl, (hydroxyl) pentyl, pentenyl, (hydroxy) heptyl, (hydroxyl) butyl, (carboxy) butyl, (carbomethoxy)butyl, (methylthio) phenyl, (methylsulfonyl)phenyl, N,N-dimethylaminomethylphenyl, N-methylaminomethylphenyl, glycylaminophenyl, N,N-dimethylglycylaminophenyl, alanylaminophenyl, (N-phenylmethoxycarbonyl)alanylaminophenyl, phenylalanylaminophenyl, (N-phenylmethoxycarbonyl) phenylalanylaminophenyl, (CH$_3$CH$_2$NHC(=O))-phenyl, N,N-diethylaminocarbonylphenyl, N-ethylaminocarbonylphenyl, N-propylaminocarbonylphenyl, N,N-diisopropylaminocarbonylphenyl, N, N-di-n-propylaminocarbonylphenyl, (hydroxypropynyl)phenyl, (imidazolyl-C(=O))-phenyl, (pyrazolyl-C(=O))phenyl, (pyridylmethylaminocarbonyl)phenyl, (oxadiazolidinonyl)phenyl, trifluoroacetylphenyl, (pyrazolyl)phenyl, (H$_2$NSO$_2$)-phenyl, dihydroxyethylphenyl, (MeHNC(=O)NH)-phenyl, (H$_2$NC(=O)NH)-phenyl, (HC(=O)NH)-phenyl, methanesulfonylpentyl, methoxypentyl, N-formyl-N-methylaminophenyl, acetylaminophenyl, propionylphenyl, butyrylphenyl, (CH$_3$CH$_2$C(=NOH))phenyl, (trifluorohydroxyethyl)phenyl, (CF$_3$C(=NOH))-phenyl, (N-methylglycyl)aminophenyl, ((4-morpholino)ethyl)aminocarbonylphenyl, (N,N-dimethylaminoethyl)aminocarbonylphenyl, (N,N-diethylaminoethyl)aminocarbonylphenyl, (4-methylpiperazin-1-ylethyl)aminocarbonylphenyl, (benzyl-NHC (=O)O)phenyl, (CH$_3$NHC(=O)O)-phenyl, (NH$_2$C(=O)CH$_2$O)phenyl, (NH$_2$C (=NH)) phenyl, ((N-phenylmethoxycarbonyl)glycylamino)phenyl, (imidazolylmethyl)phenyl, ((CH$_3$)$_3$C—C(=O)) phenyl, (N-methyl-N-ethylaminoethyl)aminocarbonylphenyl, (pyrrolidinylethyl)aminocarbonylphenyl, (piperidinylethyl)aminocarbonylphenyl, (H$_2$NC(=NOH))phenyl, (H$_2$NC(=NOH))fluorophenyl, (H$_2$NC(=NOH))fluorophenyl, (H$_2$NC(=NOH))fluorophenyl, benzimidazolyl, benzotriazolyl, indazolyl, benzoxazolinyl, benzisoxazolyl, thienyl, furyl, benzyl, N-butylaminophenyl, N,N-dimethylaminophenyl, N-propylaminophenyl, N-methylaminomethylphenyl, carbomethoxyphenyl, N-methylaminocarbonylphenyl, glycylaminophenyl, N,N-dimethylaminocarbonylphenyl, N,N-diethylaminophenyl, alanylaminophenyl, phenylalanylaminophenyl, (N-methylglycyl)aminophenyl, (H$_2$NC(=NOH))phenyl, (CH$_3$C(=NOH))phenyl, 2-amino-5-benzoxazolyl, 3-amino-5-benzisoxazolyl, 3-amino-5-indazolyl, 3-methylamino-5-indazolyl, 3-ethylamino-5-indazolyl, 3-methyl-5-indazolyl, 3-methoxy-5-indazolyl, 3-chloro-5-indazolyl, 3,4-methylenedioxyphenyl, pyridyl, 3-(2-thiazolylaminocarbonyl)phenyl, 3-(4-methyl-2-thiazolylaminocarbonyl)phenyl, 3-(1,3,4-thiadiazol-2-ylaminocarbonyl)phenyl, 3-(5-methyl-1,3,4-thiadiazol-2-ylaminocarbonyl)phenyl, 3-(5-t-butyl-1,3,4-thiadiazol-2-ylaminocarbonyl)phenyl, 3-(5-methyl-2-thiazolylaminocarbonyl)phenyl, 3-(4,5-dimethyl-2-thiazolylaminocarbonyl)phenyl, 3-(2-imidazolylaminocarbonyl)phenyl, 3-(2-pyridylaminocarbonyl)phenyl, 3-(2-benzothiazolylaminocarbonyl)phenyl, 3-(2-benzimidazolylaminocarbonyl)phenyl, 3-(2-thiazolyloxy)phenyl, and 3-(2-pyridinyloxy)phenyl;
R$^{23}$=R$^{22}$.

The compounds of this invention possess retroviral protease inhibitory activity, in particular, HIV inhibitory efficacy, as evidenced by their activity in the assays, as described in Lam et al., PCT International Publication Number WO 93/07,128, EP 402646 A1, and copending commonly assigned U.S. patent application Ser. No. 08/197,630, filed Feb. 16, 1994. The compounds of formula (IV) possess HIV protease inhibitory activity and are therefore useful as antiviral agents for the treatment of HIV infection and associated diseases as demonstrated by their HIV inhibitory activity in cellular assays and in vivo efficacy in mammals. The compounds of formula (IV) possess HIV protease inhibitory activity and are effective as inhibitors of HIV growth.

Such cyclic HIV protease inhibitors are also useful as standard or reference compounds for use in tests or assays for determining the ability of an agent to inhibit viral replication and/or HIV protease, for example in a pharmaceutical research program. Thus, such cyclic HIV protease inhibitors may be used as a control or reference compound in such assays and as a quality control standard. Such cyclic HIV protease inhibitors may be provided in a commercial kit or container for use as such standard or reference compound. Since such cyclic HIV protease inhibitors exhibit specificity for HIV protease, they may also be useful as diagnostic reagents in diagnostic assays for the detection of HIV protease. Thus, inhibition of the protease activity in an assay by such a cyclic HIV protease inhibitor would be indicative of the presence of HIV protease and HIV virus.

DETAILED DESCRIPTION OF THE INVENTION

There is provided by this invention a process for the preparation of compounds of the formula (IV) and derivatives thereof and described above. The compounds of formula (II) and (III) are useful as intermediates for the preparation of cyclic urea HIV protease inhibitor compounds. Said process comprises one or more of four chemical steps described futher below. The process of the present invention preferably comprises steps (1), (2) and (3) as described above and described further described below.

Step (1): Secondary Amine Formation

In this step, an amine of formula (I), or optionally its salt in the presence of 2.0–3.0 molar equivalents of a hindered amine base, in a solvent and controlled inerted atmosphere is contacted with about two to three molar equivalents of an aldehyde, said aldehyde being $R^{22}$—CHO or $R^{23}$—CHO, 1–4 molar equivalents of an acid, and two to seven molar equivalents of a suitable imine reducing agent for a period of 1–24 hr to form a compound of formula (II) which is isolated. $R^{22}$ and $R^{23}$ are as defined above.

A polar protic solvent is used for this step when the imine reducing agent is sodium cyanoborohydride. Suitable polar protic solvents for this step include: methanol, ethanol, isopropanol, 2-fluoroethanol, 2,2,2-trifluoroethanol, ethylene glycol, 2-methoxyethanol, 1-butanol, 2-butanol, i-butyl alcohol, t-butyl alcohol, 2-ethoxyethanol, diethylene glycol, 1-, 2-, or 3- pentanol, neo-pentyl alcohol, t-pentyl alcohol, diethylene glycol monomethyl ether, diethylene glycol monoethyl ether, cyclohexanol, anisole, benzyl alcohol, phenol, and propanol. The preferred solvent is methanol.

A nonpolar aprotic solvent is used for this step when the imine reducing agent is sodium triacetoxyborohydride or sodium borohydride. Suitable nonpolar aprotic solvents include: toluene, tetrahydrofuran, benzene, dimethoxyethane, acetonitrile, dimethoxymethane, 1,3-dioxane, 1,4-dioxane, furan, diethyl ether, ethylene glycol dimethyl ether, ethylene glycol diethyl ether, diethylene glycol dimethyl ether, diethylene glycol diethyl ether, triethylene glycol dimethyl ether, t-butyl methyl ether, cyclohexane, pentane, hexane, cycloheptane, methylcyclohexane, heptane, ethylbenzene, m-, o-, or p-xylene, octane, indane, nonane, or naphthalene. The preferred solvent is toluene.

An aprotic solvent is used for this step when the imine reducing agent is pyridine•borane complex. Suitable aprotic solvents include: benzene, cyclohexane, pentane, hexane, toluene, cycloheptane, methylcyclohexane, heptane, ethylbenzene, m-, o-, or p-xylene, octane, indane, nonane, naphthalene, dimethylformamide (DMF), dimethylacetamide (DMAC), 1,3-dimethyl-3,4,5,6-tetrahydro-2(1H)-pyrimidinone (DMPU), 1,3-dimethyl-2-imidazolidinone (DMI), N-methylpyrrolidinone (NMP), formamide, N-methylacetamide, N-methylformamide, acetonitrile, dimethyl sulfoxide, propionitrile, ethyl formate, methyl acetate, hexachloroacetone, acetone, ethyl methyl ketone, ethyl acetate, sulfolane, N,N-dimethylpropionamide, tetramethylurea, hexamethylphosphoramide, dimethoxymethane, tetrahydrofuran, 1,3-dioxane, 1,4-dioxane, furan, diethyl ether, ethylene glycol dimethyl ether, ethylene glycol diethyl ether, diethylene glycol dimethyl ether, diethylene glycol diethyl ether, triethylene glycol dimethyl ether, or t-butyl methyl ether.

The preferred molar equivalents of the aldehyde is about 2.0 to 2.1.

Suitable acids for this step include mineral acids and organic carboxylic or sulfonic acids, such as, by way of example and without limitation, hydrochloric acid, sulfuric acid, phosphoric acid, methanesulfonic acid, toluenesulfonic acid, acetic acid, formic acid, propionic acid, and citric acid. The preferred acid is an organic carboxylic acid. The most preferred acid is acetic acid. The preferred molar equivalents of acid is about 2.0 to 4.0.

Suitable imine reducing agents include formic acid, borohydrides, aluminum hydrides and transition metals. Examples of such imine reducing agents include, by way of example and without limitation: lithium aluminum hydride, diisobutyl aluminum hydride, iron pentacarbonyl, zinc with hydrochloric acid, alcoholic potassium hydroxide, lithium cyanoborohydride, palladium on carbon with hydrogen, sodium cyanoborohydride, sodium triacetoxyborohydride, sodium borohydride , and pyridine•borane complex. The preferred imine reducing agent is a borohydride or pyridine•borane complex. The preferred borohydride is sodium triacetoxyborohydride. The preferred molar equivalents of imine reducing agent is about 3.0–3.5 for sodium cyanoborohydride and sodium triacetoxyborohydride, about 4.5–5.5 for sodium borohydride with acetic acid, and about 2.0–3.0 for pyridine•borane comlex.

As used herein, a "hindered amine base" is intended to include any of a number of nitrogen containing bases wherein the nitrogen in surrounded by sterically demanding groups such that the nitrogen accessibility is reduced. Examples of hindered amine bases useful for the present invention include, by way of example and without limitation, aromatic and aliphatic amines, alkyl substituted pyridines, 1,8-diazabicyclo[2.2.2]octane (DABCO), pyridine, 4-pyrrolidinopyridine, 4-piperidinopyridine, N,N-dimethylaminopyridine (DMAP), trialkyl amines, triethylamine, N,N-diisopropylethylamine, 1,5-diazabicyclo[4.3.0]non-5-ene (DBN), 1,8-diazabicyclo[5.4.0]undec-7-ene (DBU), or tetramethylethylenediamine (TMEDA).

The product may be isolated by methods common to the skilled artisan. The preferred method of isolation is extraction of the product into an organic solvent.

Step (2): Cyclic Urea Formation

In this step, the bis N-alkylated diamine of formula (II) in an aprotic solvent at a temperature of ambient to solvent reflux in a controlled atmosphere in the presence of about 1.0–5.0 molar equivalents of a hindered amine base, as defined above, is contacted with about 0.3–4.0 molar equivalents of a suitable cyclizing agent, added at an even rate over the entire reaction period for a period of about 1–12 hr to form a compound of formula (III) which is optionally carried through without isolation to step (3).

A suitable aprotic solvent for this step includes: benzene, cyclohexane, pentane, hexane, toluene, cycloheptane, methylcyclohexane, heptane, ethylbenzene, m-, o-, or p-xylene, octane, indane, nonane, naphthalene, tetramethylurea, nitromethane, nitrobenzene, dimethoxymethane, tetrahydrofuran, 1,3-dioxane, 1,4-dioxane, furan, diethyl ether, ethylene glycol dimethyl ether, ethylene glycol diethyl ether, diethylene glycol dimethyl ether, diethylene glycol diethyl ether, triethylene glycol dimethyl ether, t-butyl methyl ether, carbon tetrachloride, bromodichloromethane, dibromochloromethane, bromoform, chloroform, bromochloromethane, dibromomethane, butyl chloride, dichloromethane, tetrachloroethylene, trichloroethylene, 1,1,1-trichloroethane, 1,1,2-trichloroethane, 1,1-dichloroethane, 2-chloropropane, hexafluorobenzene, 1,2,4-trichlorobenzene, o-dichlorobenzene, chlorobenzene, or fluorobenzene. The preferred solvent is toluene.

By "cyclizing agent" is meant a reagent or condition or combination of reagents and conditions that can effect the formation of a cyclic urea from the diamine of formula (II). Examples of suitable cyclizing reagents include but are not limited to: phenyl chloroformate, phenyl tetrazoylformate, phosgene, diphosgene, triphosgene, oxalyl chloride, N,N'-disuccinimidyl carbonate, trichloromethyl chloroformate, and 2(S),3-pyridinediyl thiocarbonate. A preferred cyclizing agent is phosgene or triphosgene. The preferred molar equivalents of cyclizing agent is about 1.0–2.5 for phosgene and about 0.4–0.6 for triphosgene.

The preferred hindered amine base is diisopropylethylamine. The preferred molar equivalents of hindered amine base is about 2.0–4.0.

Step (3): Formation of Compound (IV)

This step is necessary since a compound of formula (III), as described herein above, may not be in final form until step (3) is carried out. Thus, further deprotection or conversion chemical steps are performed by methods known by one of skill in the art in order to convert the protected diol and the substituents $R^4$, $R^7$, $R^{22}$ and $R^{23}$ into their final form and thus prepare a compound of formula (Iv) in its final and biologically active form. For example, it may be desirable to remove an amine protecting group from $R^{22}$ and/or $R^{23}$ after a compound of formula (III) has been prepared. Such a deprotection is carred out in step (3). Additionally, deprotection and/or conversion chemical steps might also be needed for groups such as, by way of example and without limitation, carboxyls, carbonyls, hydroxyls, and sulfhydryls. In this step, a compound of formula (III) is contacted with a reagent or condition or a combination of reagents and/or conditions that will effect the removal of functional group protecting groups or the conversion of a first functional group to a second functional group. As such, this step may comprise more than one chemical step. All such deprotection, protection, and conversion chemical steps known to the skilled artisan are contemplated and included within the scope of this invention.

The term "conversion chemical step" refers to any chemical reaction(s), condition(s) or combination(s) thereof where a first functional group is converted to another functional group such as, by way of example and without limitation, the conversion of an ester to an alcohol, the conversion of a nitro to an amine, or the conversion of an amine to a carbamate or an amide.

Exemplary of this step, is the removal of groups $R^{20}$ and $R^{21}$ from the cyclic urea of formula (III) to form a compound of formula (IV). Thus, a compound of formula (III) in an acid stable solvent is contacted with a reagent or condition or combination or reagents or conditions which will effect the removal of the $R^{20}$ and $R^{21}$ hydroxyl protecting groups to form a compound of formula (IV).

A suitable acid stable solvent for the removal of groups $R^{20}$ and $R^{21}$ includes: dimethoxymethane, tetrahydrofuran, 1,4-dioxane, furan, diethyl ether, ethylene glycol dimethyl ether, ethylene glycol diethyl ether, diethylene glycol dimethyl ether, diethylene glycol diethyl ether, triethylene glycol dimethyl ether, t-butyl methyl ether, water, methanol, ethanol, 2-nitroethanol, 2-fluoroethanol, 2,2,2-trifluoroethanol, ethylene glycol, 1-propanol, 2-propanol, 2-methoxyethanol, 1-butanol, 2-butanol, i-butyl alcohol, t-butyl alcohol, 2-ethoxyethanol, diethylene glycol, 1-, 2-, or 3-pentanol, neo-pentyl alcohol, t-pentyl alcohol, diethylene glycol monomethyl ether, diethylene glycol monoethyl ether, cyclohexanol, anisole, benzyl alcohol, phenol, glycerol, benzene, cyclohexane, pentane, hexane, toluene, cycloheptane, methylcyclohexane, heptane, ethylbenzene, m-, o-, or p-xylene, octane, indane, nonane, naphthalene, carbon tetrachloride, bromodichloromethane, dibromochloromethane, bromoform, chloroform, bromochloromethane, dibromomethane, butyl chloride, dichloromethane, tetrachloroethylene, trichloroethylene, 1,1,1-trichloroethane, 1,1,2-trichloroethane, 1,1-dichloroethane, 2-chloropropane, hexafluorobenzene, 1,2,4-trichlorobenzene, o-dichlorobenzene, chlorobenzene, or fluorobenzene.

As used herein, the term "hydroxyl protecting group" (or "O-protected") refers to any group known in the art of organic synthesis for the protection of hydroxyl groups. As used herein, the term "hydroxy protecting group reagent" refers to any reagent known in the art of organic synthesis for the protection of hydroxy groups which may be reacted with an hydroxy to provide an hydroxy group protected with an hydroxy protecting group. Such protecting groups include those listed in Greene and Wuts, "Protective Groups in Organic Synthesis", John Wiley & Sons, New York (1991), the disclosure of which is hereby incorporated by reference. The hydroxy protecting groups are base-stable and can include, but are not limited to acyl types, aromatic carbamate types, ether types and alkyl types. Exemplary are methyl, methoxymethyl (MOM), methylthiomethyl, benzyloxymethyl, t-butoxymethyl, 2-methoxyethoxymethyl (MEM), 2,2,2-trichloroethoxymethyl, 2-(trimethylsilyl)ethoxymethyl (SEM), tetrahydropyranyl, tetrahydrofuranyl, t-butyl, triphenylmethyl, trimethylsilyl, triethylsilyl, t-butyldimethylsilyl, t-butyldiphenylsilyl, pivaloate or N-phenylcarbamate.

Suitable hydroxyl protecting groups may also include the following protecting groups as ethers: benzyl, allyl, p-methoxybenzyloxymethyl, trichloroethoxymethyl, p-methoxybenzyl, t-butyl, o-nitrobenzyl, triphenylmethyl, oxydimethylene-1,3-diyl, p-methoxyphenyldiphenylmethyl, p-nitrobenzyl, and triisopropylsilyl.

Conditions to remove tetrahydropyranyl, triphenylmethyl, tetrahydrofuranyl, methoxymethyl, benzyloxymethyl, p-methoxybenzyloxymethyl, 2-trimethylsilylethoxymethyl, t-butoxymethyl, methylthiomethyl, 2-methoxyethoxymethyl, trichloroethoxymethyl, t-butyl, p-methoxyphenyldiphenylmethyl, may include: (a) 1–4M HCl in anhydrous or aqueous methanol, ethanol, isopropanol, tetrahydrofuran, dioxane, or diethyl ether; (b) 1–4M $H_2SO_4$ in anhydrous or aqueous methanol, ethanol, isopropanol, tetrahydrofuran, dioxane, or diethyl ether; (c) polystyrene sulfonic acid resin in anhydrous or aqueous methanol, ethanol, isopropanol, tetrahydrofuran, dioxane, or diethyl ether; (d) 10–100% trifluoroacetic acid in dichloromethane; or (e) p-toluenesulfonic acid or camphorsulfonic acid in anhydrous or aqueous methanol, ethanol, isopropanol.

Conditions to remove benzyl, benzyloxymethyl, p-methoxybenzyloxymethyl, p-methoxybenzyl, o-nitrobenzyl, p-nitrobenzyl are: hydrogenolysis in the presence of 1–17% palladium on carbon, or palladium black. Conditions to remove o-nitrobenzyl group include irradiation of the compound at 320 nm wavelength for 5–60 minutes.

Conditions to remove 2-trimethylsilylethoxymethyl, t-butyldimethylsilyl, triisopropylsilyl, t-butyldiphenylsilyl may include: treatment of the compound with tetrabutylammonium fluoride; or hydrogen flouride pyridine complex in THF, DMF or dimethylpropyleneurea.

Conditions to remove allyl may include: isomerization of the allyl ether with $[Ir(COD) (Ph_2MeP)_2]PF_6$ or $(Ph_3P)_3RhCl$ in tetrahydrofuran, diethyl ether or dioxane followed by hydrolysis with aqueous $HgCl_2$.

All of the above mentioned deprotection reactions may be carried out at temperetaures ranging from 0° C. to solvent reflux.

The compounds of formula (III) of the present invention may contain a cyclic acetal hydroxyl protecting group —OC($R^1$)($R^2$)O— or —OC($R^1$)($R^2$)OC($R^1$)($R^2$)O—. As used herein, the term "cyclic acetal protecting group" includes any protecting group known in the art of organic synthesis for the protection of 1,2-diol group through formation of a cyclic acetal or cyclic ketal group. Such protecting groups include, but are not limited to, those listed in Greene and Wuts, "Protective Groups in Organic Synthesis", john Wiley & Sons, New York (1991), the disclosure of which is hereby incorporated by reference. Examples of such cyclic acetal or ketal 1,2-diol protecting groups are methylene acetal, ethylidene acetal, 2,2,2-trichloroethylidene acetal, acetonide, cycloheptylidene ketal, cyclopentylidene ketal, cyclohexylidene ketal, benzylidene acetal, phenanthrylidene, methoxymethylene acetal, and substituted or unsubstituted carbocyclic diethers (such as oxydimethylene-1,3-diyl), dithioethers, mixed ethers, enol ethers or ketones.

The preferred hydroxyl protecting group is acetonide or oxydimethylene-1,3-diyl. When it is acetonide, the preferred conditions for removal are treatment of a compound of formula (III) in toluene or chlorobenzene with 2–10 molar equivalents of a suitable acid in the presence of 2–50 molar equivalents of an alcohol for a period of 1–4 hr to form a compound of formula (IV) which is isolated.

A suitable acid includes, by way of example and without limitation, methanesulfonic acid, benzenesulfonic acid, hydrochloric acid, hydrobromic acid, sulfuric acid, phosphoric acid, nitric acid, and toluenesulfonic . The preferred acid is methanesulfonic acid. The preferred molar equivalents is 2.0–4.0.

The preferred alcohol is methanol. The preferred molar equivalents of alcohol is 10–20.

By way of example and without limitation, the present invention may be further exemplified by reference to Scheme 8.

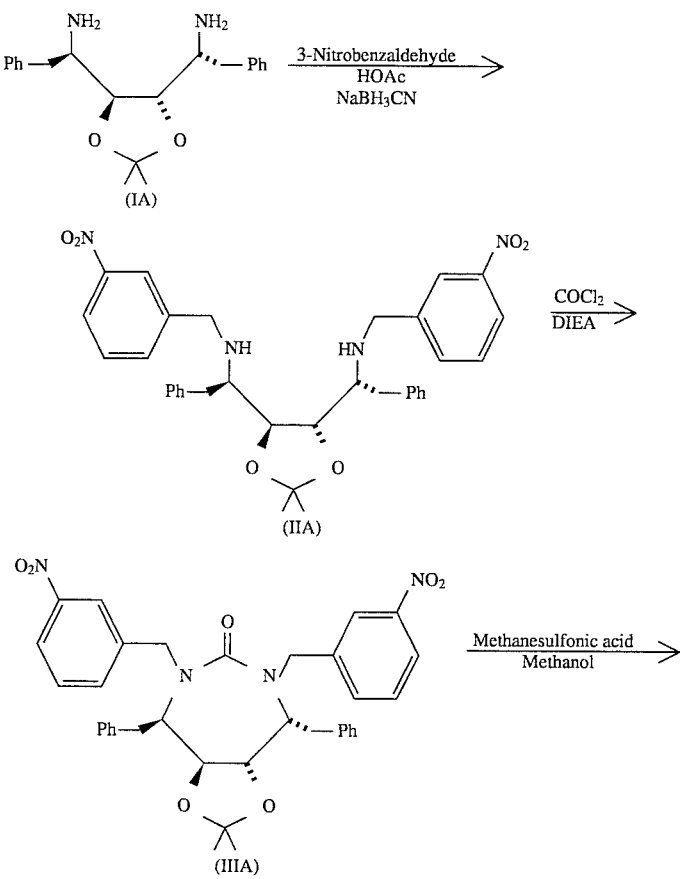

-continued
Scheme 8.

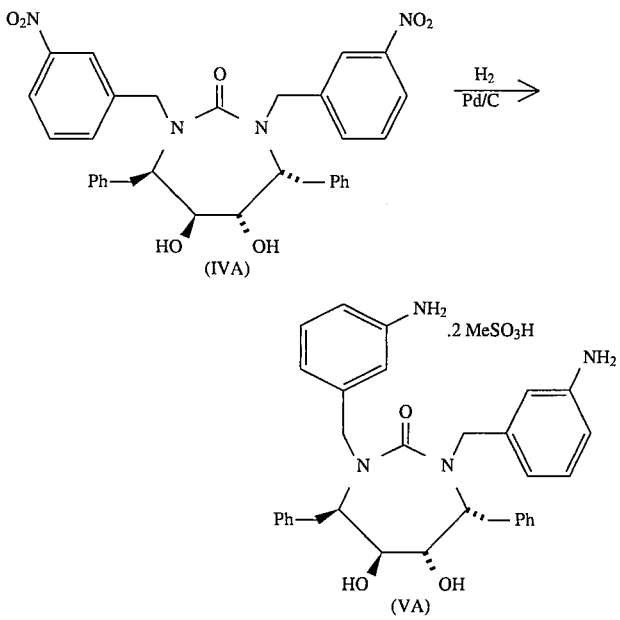

The following abbreviations may be used herein and are defined as follows. The abbreviation "Bn" means benzyl. The abbreviation "BOC" means t-butyl carbamate. The abbreviation "CBZ" means benzyl carbamate.

The compounds herein described may have asymmetric centers. All chiral, diastereomeric, and racemic forms are included in the present invention. Many geometric isomers of olefins, C=N double bonds, and the like can also be present in the compounds described herein, and all such stable isomers are contemplated in the present invention. It will be appreciated that certain compounds of the present invention contain an asymmetrically substituted carbon atom, and may be isolated in optically active or racemic forms° It is well known in the art how to prepare optically active forms, such as by resolution of racemic forms or by synthesis, from optically active starting materials. Also, it is realized that cis and trans geometric isomers of the compounds of the present invention are described and may be isolated as a mixture of isomers or as separated isomeric forms. All chiral, diastereomeric, racemic forms and all geometric isomeric forms of a structure are intended, unless the specific stereochemistry or isomer form is specifically indicated.

As used herein, the term "amine protecting group" (or "N-protected") refers to any group known in the art of organic synthesis for the protection of amine groups. The term "amine protecting group reagent" refers to any reagent known in the art of organic synthesis for the protection of amine groups which may be reacted with an amine to provide an amine protected with an amine protecting group. Such amine protecting groups include those listed in Greene and Wuts, "Protective Groups in Organic Synthesis" John Wiley & Sons, New York (1991) and "The Peptides: Analysis, Synthesis, Biology, Vol. 3, Academic Press, New York (1981), the disclosure of which is hereby incorporated by reference. Examples of amine protecting groups include, but are not limited to, the following: 1) acyl types such as formyl, trifluoroacetyl, phthalyl, and p-toluenesulfonyl; 2) aromatic carbamate types such as benzyloxycarbonyl (Cbz) and substituted benzyloxycarbonyls, 1-(p-biphenyl)-1-methylethoxycarbonyl, and 9-fluorenylmethyloxycarbonyl (Fmoc); 3) aliphatic carbamate types such as tertbutyloxycarbonyl (Boc), ethoxycarbonyl, diisopropylmethoxycarbonyl, and allyloxycarbonyl; 4) cyclic alkyl carbamate types such as cyclopentyloxycarbonyl and adamantyloxycarbonyl; 5) alkyl types such as triphenylmethyl and benzyl; 6) trialkylsilane such as trimethylsilane; and 7) thiol containing types such as phenylthiocarbonyl and dithiasuccinoyl.

Amine protecting groups may include, but are not limited to the following: 2,7-di-t-butyl-[9-(10,10-dioxo-10,10,10,10-tetrahydrothioxanthyl)]methyloxycarbonyl; 2-trimethylsilylethyloxycarbonyl; 2-phenylethyloxycarbonyl; 1,1-dimethyl-2,2-dibromoethyloxycarbonyl; 1-methyl-1-(4-biphenylyl)ethyloxycarbonyl; benzyloxycarbonyl; p-nitrobenzyloxycarbonyl; 2-(p-toluenesulfonyl)ethyloxycarbonyl; m-chloro-p-acyloxybenzyloxycarbonyl; 5-benzyisoxazolylmethyloxycarbonyl; p-(dihydroxyboryl)benzyloxycarbonyl; m-nitrophenyloxycarbonyl; o-nitrobenzyloxycarbonyl; 3,5-dimethoxybenzyloxycarbonyl; 3,4-dimethoxy-6-nitrobenzyloxycarbonyl; N'-p-toluenesulfonylaminocarbonyl; t-amyloxycarbonyl; p-decyloxybenzyloxycarbonyl; diisopropylmethyloxycarbonyl; 2,2-dimethoxycarbonylvinyloxycarbonyl; di(2-pyridyl)methyloxycarbonyl; 2-furanylmethyloxycarbonyl; phthalimide; dithiasuccinimide; 2,5-dimethylpyrrole; benzyl; 5-dibenzylsuberyl; triphenylmethyl; benzylidene; diphenylmethylene; or methanesulfonamide.

As used herein, the term "carboxyl protecting group" refers to any group known in the art of organic synthesis for the protection of carboxyl groups. Such carboxyl protecting groups include those listed in Greene and Wuts, "Protective Groups in Organic Synthesis" John Wiley & Sons, New York (1991) and "The Peptides: Analysis, Synthesis, Biology, Vol. 3, Academic Press, New York (1981), the disclosure of which is hereby incorporated by reference. Examples of carboxyl protecting groups include, but are not limited to, the following: 1) substituted methyl ester type such as methoxymethyl, tetrahydropyranyl, benzyloxymethyl, N-phthalimidomethyl; 2) 2-substituted ethyl ester type such as 2,2,2-trichloroethyl, 2-methylthioethyl, t-butylethyl, cinnamylethyl, benzylethyl, 2-(2'-pyridyl)ethyl; 3) substituted benzyl ester type such as triphenylmethyl, 9-anthrylmethyl, p-nitrobenzyl, 4-picolyl, 2,4,6-trimethylbenzyl; 4) silyl ester type such as trimethylsilyl, t-butyldimethylsilyl, phenyldimethylsilyl; 5) miscellaneous type such as oxazole, orthoester; 6) amides type such as N,N-dimethyl, piperidinyl, pyrrolindinyl; and 7) hydrazide type such as alkylated hydrazides.

When any variable (for example $R^{11}$, $R^{12}$, $R^{13}$, $R^{14}$, m, etc.) occurs more than one time in any constituent or formula for a compound, its definition on each occurrence is independent of its definition at every other occurrence. Thus, for example, if a group is shown to be substituted with 0–3 $R^{11}$, then said group may optionally be substituted with up to three $R^{11}$ and $R^{11}$ at each occurrence is selected independently from the defined list of possible $R^{11}$. Also, combinations of substituents and/or variables are permissible only if such combinations result in stable compounds. By stable compound or stable structure it is meant herein a compound that is sufficiently robust to survive isolation to a useful degree of purity from a reaction mixture. Similarly, by way of example, for the group —C($R^{11}$)$_2$—, each of the two $R^{11}$ substituents on C is independently selected from the defined list of possible $R^{11}$.

When a bond to a substituent is shown to cross the bond connecting two atoms in a ring, then such substituent may be bonded to any atom on the ring. When a substituent is listed without indicating the atom via which such substituent is bonded to the rest of the compound of a given formula, then such substituent may be bonded via any atom in such substituent. For example, when the substituent is piperazinyl, piperidinyl, or tetrazolyl, unless specified otherwise, said piperazinyl, piperidinyl, tetrazolyl group may be bonded to the rest of the compound of a given formula via any atom in such piperazinyl, piperidinyl, tetrazolyl group.

Combinations of substituents and/or variables are permissible only if such combinations result in stable compounds. By stable compound or stable structure it is meant herein a compound that is sufficiently robust to survive isolation to a useful degree of purity from a reaction mixture, and formulation into an efficacious therapeutic agent.

As used herein, "alkyl" is intended to include both branched and straight-chain saturated aliphatic hydrocarbon groups having the specified number of carbon atoms; "haloalkyl" is intended to include both branched and straight-chain saturated aliphatic hydrocarbon groups having the specified number of carbon atoms, substituted with 1 or more halogen (for example —$C_vF_w$ where v=1 to 3 and w=1 to (2v+1)); "alkoxy" represents an alkyl group of indicated number of carbon atoms attached through an oxygen bridge; "cycloalkyl" is intended to include saturated ring groups, including mono-, bi- or poly-cyclic ring systems, such as cyclopropyl, cyclobutyl, cyclopentyl, cyclohexyl, cycloheptyl, adamantyl and cyclooctyl; and "bicloalkyl" is intended to include saturated bicyclic ring groups such as [3.3.0]bicyclooctane, [4.3.0]bicyclononane, [4.4.0]bicyclodecane (decalin), [2.2.2]bicyclooctane, and so forth. "Alkenyl" is intended to include hydrocarbon chains of either a straight or branched configuration and one or more unsaturated carbon-carbon bonds which may occur in any stable point along the chain, such as ethenyl, propenyl, and the like; and "alkynyl" is intended to include hydrocarbon chains of either a straight or branched configuration and one or more triple carbon-carbon bonds which may occur in any stable point along the chain, such as ethynyl, propynyl and the like.

The terms "-(alkyl)-", "-(alkyenyl)-", "-(phenyl)-", and the like, refer to alkyl, alkenyl, and phenyl groups, respectively, which are connected by two bonds to the rest of the structure of Formula (II). Such groups may alternatively and equivalently be denoted as "alkylene", "alkenylene", "phenylene", and the like, respectively.

"Alkylcarbonyl" is intended to include an alkyl group of an indicated number of carbon atoms attached through a carbonyl group to the residue of the compound at the designated location. "Alkylcarbonylamino" is intended to include an alkyl group of an indicated number of carbon atoms attached through a carbonyl group to an amino bridge, where the bridge is attached to the residue of the compound at the designated location. "Alkylcarbonyloxy" is intended to include an alkyl group of an indicated number of carbon atoms attached to a carbonyl group, where the carbonyl group is attached through an oxygen atom to the residue of the compound at the designated location.

"Halo" or "halogen" as used herein refers to fluoro, chloro, bromo, and iodo; and "counterion" is used to represent a small, negatively charged species such as chloride, bromide, hydroxide, acetate, sulfate, and the like.

As used herein, "aryl" or "aromatic residue" is intended to mean phenyl or naphthyl; the term "arylalkyl" represents an aryl group attached through an alkyl bridge. By way of examples: the term "$C_7$–$C_{10}$ arylalkyl" is intended to refer to an aryl group attached through a $C_1$–$C_4$ alkyl bridge to the residue of the indicated compound; the term "($C_1$–$C_3$ alkyl)aryl" is intended to refer to a $C_1$–$C_3$ alkyl group which is attached through an aryl ring to the residue of the indicated compound; the term "aryl($C_1$–$C_3$ alkyl)" is intended to refer to an aryl group attached through a $C_1$–$C_3$ alkyl group to the residue of the indicated compound.

As used herein, "carbocycle" or "carbocyclic residue" is intended to mean any stable 3- to 7-membered monocyclic or bicyclic or 7- to 14-membered bicyclic or tricyclic or an up to 26-membered polycyclic carbon ring, any of which may be saturated, partially unsaturated, or aromatic. Examples of such carbocyles include, but are not limited to, cyclopropyl, cyclopentyl, cyclohexyl, phenyl, biphenyl, naphthyl, indanyl, adamantyl, or tetrahydronaphthyl (tetralin).

As used herein, the term "heterocycle" is intended to mean a stable 5- to 7- membered monocyclic or bicyclic or 7- to 10-membered bicyclic heterocyclic ring which is either saturated or unsaturated, and which consists of carbon atoms and from 1 to 4 heteroatoms independently selected from the group consisting of N, O and S and wherein the nitrogen and sulfur heteroatoms may optionally be oxidized, and the nitrogen may optionally be quaternized, and including any bicyclic group in which any of the above-defined heterocyclic rings is fused to a benzene ring. The heterocyclic ring may be attached to its pendant group at any heteroatom or carbon atom which results in a stable structure. The heterocyclic rings described herein may be substituted on carbon or on a nitrogen atom if the resulting compound is stable. Examples of such heterocycles include, but are not limited to, 1H-indazole, 2-pyrrolidonyl, 2H,6H-1,5,2-dithiazinyl, 2H-pyrrolyl, 3H-indolyl, 4-piperidonyl, 4aH-carbazole, 4H-quinolizinyl, 6H-1,2,5-thiadiazinyl, acridinyl, azocinyl, benzofuranyl, benzothiophenyl, carbazole, chromanyl, chromenyl, cinnolinyl, decahydroquinolinyl, furanyl, furazanyl, imidazolidinyl, imidazolinyl, imidazolyl, indolinyl, indolizinyl, indolyl, isobenzofuranyl, isochromanyl, isoindolinyl, isoindolyl, isoquinolinyl (benzimidazolyl), isothiazolyl, isoxazolyl, morpholinyl, naphthyridinyl, octahydroisoquinolinyl, oxazolidinyl, oxazolyl, phenanthridinyl, phenanthrolinyl, phenarsazinyl, phenazinyl, phenothiazinyl, phenoxathiinyl, phenoxazinyl, phthalazinyl, piperazinyl, piperidinyl, pteridinyl, purinyl, pyranyl, pyrazinyl, pyrazolidinyl, pyrazolinyl, pyrazolyl, pyridazinyl, pyridinyl, pyridyl, pyrimidinyl, pyrrolidinyl, pyrrolinyl, pyrrolyl, quinazolinyl, quinolinyl, quinoxalinyl, quinuclidinyl, carbolinyl, tetrahydrofuranyl, tetrahydroisoquinolinyl, tetrahydroquinolinyl, tetrazolyl, thianthrenyl, thiazolyl, thienyl, thiophenyl, triazinyl, xanthenyl. Also included are fused ring and spiro compounds containing, for example, the above heterocycles.

The term "substituted", as used herein, means that any one or more hydrogens on the designated atom is replaced with a selection from the indicated group, provided that the designated atom's normal valency is not exceeded, and that the substitution results in a stable compound. When a substitent is keto (i.e., =O), then 2 hydrogens on the atom are replaced.

The term "amino acid" as used herein means an organic compound containing both a basic amino group and an acidic carboxyl group. Included within this term are natural amino acids, modified and unusual amino acids, as well as amino acids which are known to occur biologically in free or combined form but usually do not occur in proteins. Included within this term are modified and unusual amino acids, such as those disclosed in, for example, Roberts and Vellaccio (1983) *The Peptides,* 5: 342–429, the teaching of which is hereby incorporated by reference. Modified or unusual amino acids which can be used to practice the invention include, but are not limited to, D-amino acids, hydroxylysine, 4-hydroxyproline, an N-Cbz-protected amino acid, ornithine, 2,4-diaminobutyric acid, homoarginine, norleucine, N-methylaminobutyric acid, naphthylalanine, phenylglycine, β-phenylproline, tert-leucine, 4-aminocyclohexylalanine, N-methylnorleucine, 3,4-dehydroproline, N,N-dimethylaminoglycine, N-methylaminoglycine, 4-aminopiperidine-4-carboxylic acid, 6-aminocaproic acid, trans-4-(aminomethyl)-cyclohexanecarboxylic acid, 2-, 3-, and 4-(aminomethyl)-benzoic acid, 1-aminocyclopentanecarboxylic acid, 1-aminocyclopropanecarboxylic acid, and 2-benzyl-5-aminopentanoic acid.

The term "amino acid residue" as used herein means that portion of an amino acid (as defined herein) that is present in a peptide.

The term "peptide" as used herein means a compound that consists of two or more amino acids (as defined herein) that are linked by means of a peptide bond. The term "peptide" also includes compounds containing both peptide and non-peptide components, such as pseudopeptide or peptide mimetic residues or other non-amino acid components. Such a compound containing both peptide and non-peptide components may also be referred to as a "peptide analog".

The term "peptide bond" means a covalent amide linkage formed by loss of a molecule of water between the carboxyl group of one amino acid and the amino group of a second amino acid.

As used herein, "pharmaceutically acceptable salts" refer to derivatives of the disclosed compounds wherein the parent compound is modified by making acid or base salts thereof. Examples of pharmaceutically acceptable salts include, but are not limited to, mineral or organic acid salts of basic residues such as amines; alkali or organic salts of acidic residues such as carboxylic acids; and the like. The pharmaceutically acceptable salts include the conventional non-toxic salts or the quaternary ammonium salts of the parent compound formed, for example, from non-toxic inorganic or organic acids. For example, such conventional non-toxic salts include those derived from inorganic acids such as hydrochloric, hydrobromic, sulfuric, sulfamic, phosphoric, nitric and the like; and the salts prepared from organic acids such as acetic, propionic, succinic, glycolic, stearic, lactic, malic, tartaric, citric, ascorbic, pamoic, maleic, hydroxymaleic, phenylacetic, glutamic, benzoic, salicylic, sulfanilic, 2-acetoxybenzoic, fumaric, toluenesulfonic, methanesulfonic, ethane disulfonic, oxalic, isethionic, and the like.

The pharmaceutically acceptable salts of the present invention can be synthesized from the parent compound which contains a basic or acidic moiety by conventional chemical methods. Generally, such salts can be prepared by reacting the free acid or base forms of these compounds with a stoichiometric amount of the appropriate base or acid in water or in an organic solvent, or in a mixture of the two; generally, nonaqueous media like ether, ethyl acetate, ethanol, isopropanol, or acetonitrile are preferred. Lists of suitable salts are found in *Remington's Pharmaceutical Sciences,* 17th ed., Mack Publishing Company, Easton, Pa., 1985, p. 1418, the disclosure of which is hereby incorporated by reference.

The phrase "pharmaceutically acceptable" is employed herein to refer to those compounds, materials, compositions, and/or dosage forms which are, within the scope of sound medical judgment, suitable for use in contact with the tissues of human beings and animals without excessive toxicity, irritation, allergic response, or other problem or complication, commensurate with a reasonable benefit/risk ratio.

Synthesis

The disclosures of all of the references cited herein are hereby incorporated herein by reference in their entirety.

Using the procedures described above and outlined in Schemes 7 and 8, the following compounds were prepared. The following examples are meant to be illustrative of the present invention. These examples are not to be construed as limiting the invention's scope. With a judicious selection of reagents, as is well appreciated to one skilled in the art, these manipulations can be performed in a straightforward manner to yield the claimed combinations for compounds of the formulas (II), (III) and (IV).

EXAMPLE 1

Synthesis of Compound (IIA):

Reduction with Sodium Cyanoborohydride

The diamine (IA) (5.0 g, 14.7 mmol) was dissolved in methanol (100 mL) and stirred under nitrogen. 3-nitrobenzaldehyde (4.88 g, 32.3 mmol) was added and the resulting solution stirred for 2 hours. Glacial acetic acid (1.68 mL, 29.4 mmol) was added followed by sodium cyanoborohydride (2.77 g, 44.1 mmol) in portions. The mixture was stirred overnight and then partioned between methylene chloride and sodium bicarbonate solution. The aqueous phase was extracted twice more with methylene chloride. The combined organic layers were washed with brine, dried over sodium sulfate, filtered and evaporated. The residue was recrystallized from hexane/ethyl acetate (60 mL, 5/1) to give the pure product (IIA) as an off-white solid (6.8 g, 76% yield), mp 110°–111° C.

EXAMPLE 2

Synthesis of Compound (IIA):

Reduction with Sodium Triacetoxyborohydride

A suspension of the bis p-TsOH salt of the diamine (IA) (635 g, 0.9 mol) in toluene (4.0 L) was stirred under nitrogen while triethylamine (219 g, 2.17 mol) was added over 20 minutes. After stirring an additional 30 minutes, 3-nitrobenzaldehyde (312 g, 2.06 mol) was added over a 30–45 minute period. The mixture was heated, held at 70°–75° C. for one hour and then cooled to room temperature. Glacial acetic acid ($^{132}$ g, 2.2 mol) was added followed by sodium triacetoxyborohydride (570 g, 2.69 mol) in three portions over a one hour period and the mixture stirred overnight. The reaction was shown to be complete by HPLC analysis. Water (2.0 L) was added slowly and the mixture stirred until gas evolution stopped. The organic phase was washed with water (2.0 L), sodium carbonate solution (0.9 L) and water (0.25 L). Most of the toluene was distilled off under vacuum, isopropanol (3.35 L) added and heated to reflux to obtain a clear solution. After stirring at ambient temperature overnight, the suspension was stirred at 0°–5° C. C for two hours. The solids were filtered, washed with cold isopropanol (0.6 L) and dried in a vacuum oven at 40° C. to afford the product (IIA) as an off-white solid (468 g, 83% yield), mp 110°≧111° C.

EXAMPLE 3

Synthesis of Compound (IIA):

Reduction with Sodium Borohydride and Acetic Acid

The bis p-TsOH salt of the diamine (IA) (6.03 g, 8.81 mmol) was partitioned between toluene (40 mL) and a 1N NaOH solution. The toluene solution was washed with 1N NaOH, water and brine then dried over $Na_2SO_4$ and filtered directly into the reaction flask rinsing with more toluene (20 mL). To the clear solution stirring under nitrogen was added 3-nitrobenzaldehyde (2.94 g, 19.4 mmol). After 0.5 hr., glacial acetic acid (1.9 mL, 33 mmol) was added followed by portionwise addition of sodium borohydride (1.67 g, 44 mmol). Four hours later, 10 mL methanol was slowly added. When gas evolution stopped, water (60 mL) was added. The toluene solution was washed with water (60 mL), brine (60 mL), dried over $Na_2SO_4$, filtered and evaporated. The crude product was recrystallized from isopropanol (35 mL) to give the pure product (IIA) as an off-white solid (4.5 g, 84% yield), mp 107°–110° C.

EXAMPLE 4

Synthesis of Compound (IIA):

Reduction with Pyridine•Borane Complex

The bis p-TsOH salt of the diamine (IA) (485 g, 0.69 mol) was suspended in toluene (4 L) and stirred under nitrogen while diisopropyl ethylamine (200 g, 1.65 mol) and 3-nitrobenzaldehyde (234 g, 1.53 mol) were added. The mixture was heated at reflux for 45 minutes and then cooled to 5° C. Glacial acetic acid (100 g, 1.67 mol) was added followed by pyridine-borane complex (220 mL, 1.76 mol). The resulting solution was stirred at room temperature for 2 hours, 60° C. for 2 hours and then 90° C. for 30 minutes. After cooling to room temperature, the toluene solution was washed with water (4 L), sodium carbonate solution (4 L, 5%) and water (4 L). Most of the toluene was evaporated and isopropanol (4 L) added to crystallize the product (IIA) affording a white solid (391 g, 95.3 wt % purity, 89% yield), mp 109°–111° C.

EXAMPLE 5

Synthesis of Compounds (IIIA) and (IVA):

Cyclization with Phosgene

Part A: Compound (IIIA)

The bis benzylamine (IIA) (1.0 g, 1.64 mmol) and N,N'-diisopropylethylamine (0.86 mL, 4.91 mmol) were dissolved in toluene (20 mL). The solution was heated at reflux under nitrogen while a phosgene solution in toluene ( 2.0 mL, 1.93M, 3.86 mmol) was added via syringe pump over 2 hours. Afer an additional 5 minutes at reflux, the heat was removed.

Part B: Compound (IVA)

The solution of cyclic urea (IIIA) obtained from above was deprotected in situ by the addition of methanol (1 mL, 24.7 mmol) and methanesulfonic acid (0.42 mL, 6.55 mmol), and the mixture stirred at ambient temperature for 2 hours. Water (15 mL) was added and the slurry stirred in an ice bath for one hour. The solids were filtered, washed with water and heptane and dried to give the pure diol (IVa) as an off-white solid (0.70 g, 71% yield), mp 236°–240° C. (dec).

EXAMPLE 6

Synthesis of Compounds (IIIA) and (IVA):

Cyclization with Triphosgene

Part A: Compound (IIIA)

The his benzylamine (IIA) (250 g, 0.39 mol) was combined with diisopropyl ethylamine ($^{130}$ g, 1.0 mol) in chlorobenzene (4.1 L) under nitrogen and the mixture heated to 125° C. A solution of triphosgene (53.8 g, 0.18 mol) in chlorobenzene (1.5 L) was slowly added over a 6 hour period. The mixture was then heated at reflux for 30 minutes and then cooled to room temperature.

Part B: Compound (IVA)

The solution of cyclic urea (IIIA) was deprotected in situ. Methanesulfonic acid (84 g, 0.87 mol) and methanol (250 mL) were added and the solution stirred for one hour. Water (3.8 L) was added and the mixture stirred at 5° C. for one hour to precipatate the product. The solid was filtered and washed with water (900 mL) and then heptane (900 mL). Drying at 60° C. for 3 hours afforded the diol (IVA) (189 g, 96 wt% purity, 78% yield), mp 241°–243° C.

EXAMPLE 7

Synthesis of Compounds (VA):

Conversion of Nitro to Amino

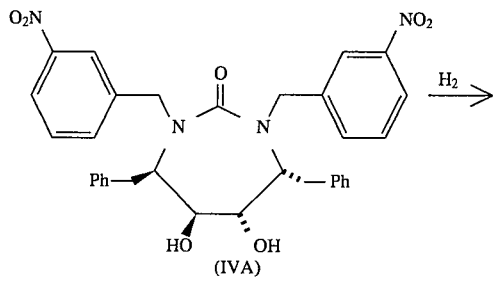

The bis-nitrobenzyl cyclic urea (IVA) (100.0 g, 0.166 moles), isopropanol (1000 mL), water (150 mL), methanesulfonic acid (21.6 mL, 0.333 moles) and Pd/C (10% wt, 7.1 g) were placed in a stirred round bottom flask. After three purges with hydrogen, the flask was heated to 40° C. under a flow of hydrogen. After completion of reaction, (24 hrs), Ecosorb (20 g) was added and the mixture stirred (1 hr) and filtered over paper. Karl Fischer titration of the filtrate indicated 11.9 % wt of water. The water was removed by repeated azeotropic distillation with isopropanol to a water content <0.2% wt. The final dry isopropanol solution containing (VA) was chilled and the crystallized product collected by filtration and dried in a vacuum oven (114.47 g, >99 wt % purity, 91% yield). Mp 205°–207° C.

EXAMPLE 8

Synthesis of Compound (IIB)

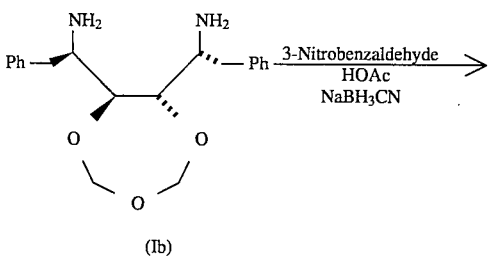

The procedure described in Example 1 was used to convert the diamino trioxepane (IB) into the disubstituted secondary amine (IIb) in 70% yield, mp 116°–118° C.

EXAMPLE 9

Synthesis of Compound (IIIB)

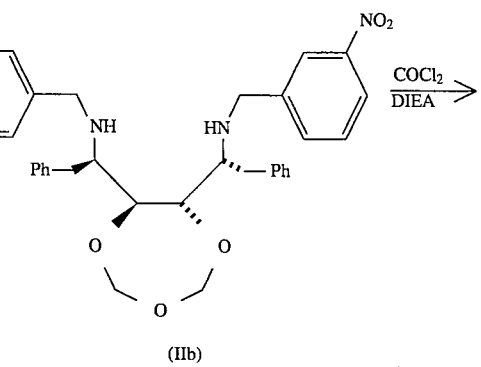

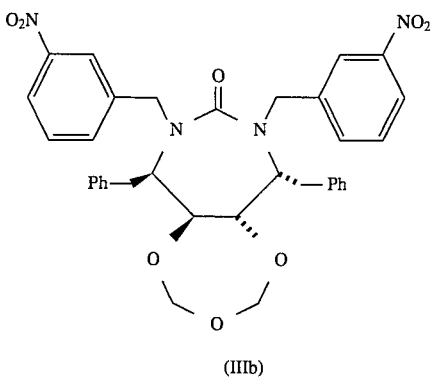

The cyclization portion of the procedure described in Example 5, but in acetonitrile at room temperature was used to convert the disubstituted benzylamine (IIB) into the cyclic urea (IIIB) in 85% yield after chromatography: mp 125°–129° C.

EXAMPLE 10

Synthesis of Compound (IIC)

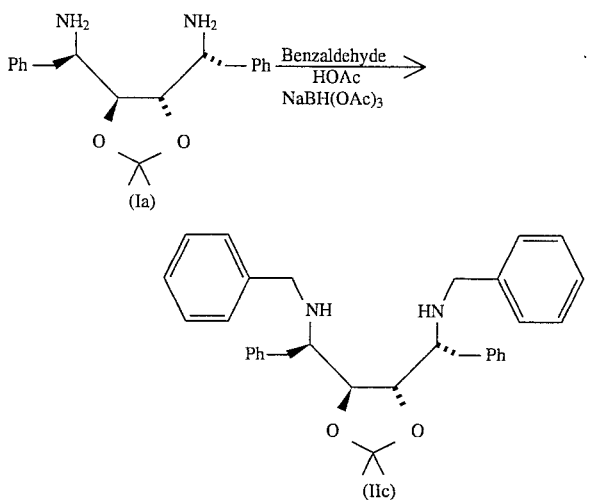

The procedure described in Example 2 was used to convert the diamino acetonide (IA) into the bis benzylamine (IIC) in 99% crude yield suitable for use in the next step without further purification, mp 95°–96° C. (analytical sample mp 102°–103° C.).

EXAMPLE 11

Synthesis of Compound (IIIC)

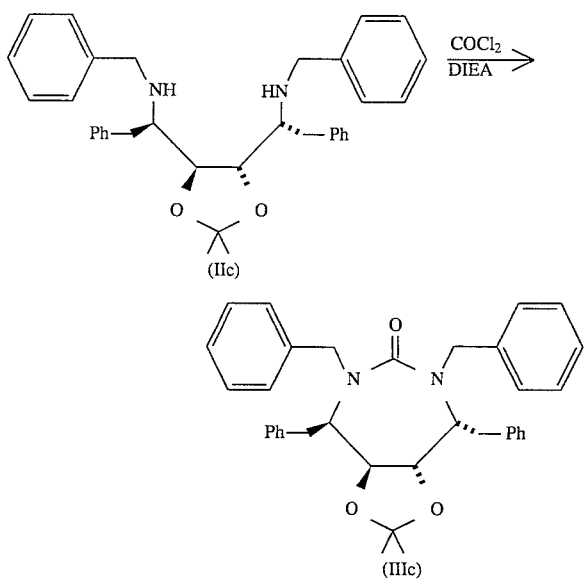

The cyclization portion of the procedure described in Example 5 was used to convert the bis benzylamine (IIC) into the cyclic urea (IIIC) in 66% yield after chromatography on silica with methylene chloride. An analytical sample was recrystallized from hexane, mp 138°–140° C.

EXAMPLE 12

100 g Scale Synthesis of Compounds (IIIA) and (IVA):

Cyclization with Triphosgene

A 4-necked round bottom flask (5 L) equipped with a mechanical stirrer, thermometer and a condenser with a nitrogen bubbler was purged with nitrogen for 10 min. This flask was charged with compound (IIA) (100 g, 93.2% purity, 0.15 mol), chlorobenzene (1 L) and diisopropyl ethylamine (65 g, 0.5 mol). The solution was heated to 125° C., and a solution of triphosgene (25 g, 0.08 mol) in chlorobenzene (1.5 L) was added dropwise over a period of 6 h. After addition was complete, the solution was heated to reflux for 30 min, and then cooled to room temperature to form compound (IIIA) in solution. Methanesulfonic acid (70 g) and methanol (200 mL) were then added successively. The solution was stirred at room temperature for 1 h, and water (1.5 L) was added. The mixture was cooled at 5° C. for 1 h, and the product was precipitated out from the solution. The desired product compound (IVA) (78.6 g, 97 wt %, 85% yield) was collecteded by filtration, washing (water, 300 mL; heptane, 300 mL) and drying (60 C, 3 h).

Although this invention has been described with respect to specific embodiments, the details of these embodiments are not to be construed as limitations. Various equivalents, changes and modifications may be made without departing from the spirit and scope of this invention, and it is understood that such equivalent embodiments are part of this invention. The present invention may be embodied in other specific forms without departing from the spirit or essential attributes thereof and, accordingly, reference should be made to the appended claims as further indicating the scope of the invention.

What is claimed is:

1. A process for the preparation of a compound of formula (IV):

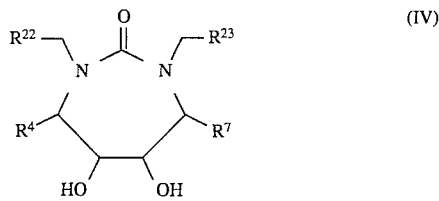

wherein:

$R^4$ and $R^7$ are independently selected from the following groups:

$C_1$–$C_8$ alkyl substituted with 0–3 $R^{11}$;

$C_2$–$C_8$ alkenyl substituted with 0–3 $R^{11}$;

$C_2$–$C_8$ alkynyl substituted with 0–3 $R^{11}$;

$R^{11}$ is selected from one or more of the following:

H, keto, halogen, cyano, —$CH_2NR^{13}R^{14}$, —$NR^{13}R^{14}$, —$CO_2R^{13}$, —$OC(=O)R^{13}$, —$OR^{13}$, —$S(O)_mR^{13}$, —$NHC(=NH)NHR^{13}$, —$C(=NH)NHR^{13}$, —$C(=O)NR^{13}R^{14}$, —$NR^{14}C(=O)R^{13}$, =$NOR^{14}$, —$NR^{14}C(=O)OR^{14}$, —$OC(=O)NR^{13}R^{14}$, —$NR^{13}C(=O)NR^{13}R^{14}$, —$NR^{14}SO_2NR^{13}R^{14}$, —$NR^{14}SO_2R^{13}$, —$SO_2NR^{13}R^{14}$, —$OP(O)(OR^{13})_2$, $C_1$–$C_4$ alkyl, $C_2$–$C_4$ alkenyl, $C_3$–$C_6$ cycloalkylmethyl, phenyl, benzyl, phenethyl, phenoxy, benzyloxy, nitro, $C_7$–$C_{10}$ arylalkyl, hydroxamic acid, hydrazide, boronic acid, sulfonamide, formyl, $C_3$–$C_6$ cycloalkoxy, $C_1$–$C_4$ alkyl substituted with —$NR^{13}R^{14}$, $C_1$–$C_4$ hydroxyalkyl, methylenedioxy, ethylenedioxy, $C_1$–$C_4$ haloalkyl, $C_1$–$C_4$ haloalkoxy, $C_1$–$C_4$ alkoxycarbonyl, pyridylcarbonyloxy, $C_1$–$C_4$ alkylcarbonyl, $C_1$–$C_4$ alkylcarbonylamino, —$OCH_2CO_2H$, 2-(1-morpholino) ethoxy, azido, —$C(R^{14})=N(OR^{14})$; or $C_3$–$C_{10}$ cycloalkyl substituted with 0–2 $R^{12}$;

$C_1$–$C_4$ alkyl substitued with 0–2 $R^{12}$;

aryl($C_1$–$C_3$ alkyl)-, substituted with 0–2 $R^{12}$;

$C_2$–$C_6$ alkoxyalkyl-, substituted with 0–2 $R^{12}$;

$C_1$-$C_4$ alkylcarbonyloxy substituted with 0-2 $R^{12}$;

$C_6$-$C_{10}$ arylcarbonyloxy substituted with 0-2 $R^{12}$;

a $C_5$-$C_{14}$ carbocyclic residue substituted with 0-3 $R^{12}$;

a 5- to 10-membered heterocyclic ring system containing 1 to 4 heteroatoms independently selected from oxygen, nitrogen or sulfur, said heterocyclic ring system being substituted with 0-3 $R^{12}$;

$R^{11A}$ is selected from one or more of the following:

H, keto, halogen, cyano, —$CH_2N(R^{13A})R(^{14A})$, —$OR^{13A}$ —$N(R^{13A})R(^{14A})$, —$CO_2H$, —$OC(=O)(C_1$-$C_3$ alkyl), —OH, $C_2$-$C_6$ alkoxyalkyl, —$C(=O)NH_2$, —$OC(=O)NH_2$, -$NHC(=O)NH_2$, —$SO_2NH_2$, $C_1$-$C_4$ alkyl, $C_2$-$C_4$ alkenyl, $C_3$-$C_{10}$ cycloalkyl, $C_3$-$C_6$ cycloalkylmethyl, benzyl, phenethyl, phenoxy, benzyloxy, nitro, $C_7$-$C_{10}$ arylalkyl, hydroxamic acid, hydrazide, boronic acid, $C_3$-$C_6$ cycloalkoxy, $C_1$-$C_4$ alkyl substituted with —$NH_2$, $C_1$-$C_4$ hydroxyalkyl, methylenedioxy, ethylenedioxy, $C_1$-$C_4$ haloalkyl, $C_1$-$C_4$ haloalkoxy, $C_1$-$C_4$ alkoxycarbonyl, $C_1$-$C_4$ alkylcarbonyloxy, $C_1$-$C_4$ alkylcarbonyl, $C_1$-$C_4$ alkylcarbonylamino, —$OCH_2CO_2H$, 2-(1-morpholino)ethoxy, azido, aryl($C_1$-$C_3$ alkyl); or $C_3$-$C_{10}$ cycloalkyl substituted with 0-2 $R^{12A}$, $C_1$-$C_4$ alkyl substituted with 0-2 $R^{12A}$, aryl($C_1$-$C_3$ alkyl)- substituted with 0-2 $R^{12A}$;

a 5- to 10-membered heterocyclic ring system containing 1 to 4 heteroatoms independently selected from oxygen, nitrogen or sulfur, said heterocyclic ring system substituted with 0-3 $R^{12A}$; or —$SO_mR^{13A}$, $C_1$-$C_4$ haloalkyl, $C_1$-$C_4$ haloalkoxy, $C_1$-$C_4$ alkoxy, $C_2$-$C_4$ alkynyl, phenyl, said phenyl being optionally substituted with Cl, F, Br, CN, $NO_2$, $CF_3$, $C_1$-$C_4$ alkyl, $C_1$-$C_4$ alkoxy or OH; or alternately, $R^{11A}$ and $R^{16}$, when substituents on adjacent carbons, can be taken together with the carbon atoms to which they are attached to form a 5-6 membered carbocyclic or heterocyclic ring system, said carbocyclic or heterocyclic ring system being optionally substituted with Cl, F, Br, CN, $NO_2$, $CF_3$, $C_1$-$C_4$ alkyl, $C_1$-$C_4$ alkoxy or OH;

$R^{12}$, when a substituent on carbon, is selected from one or more of the following:

phenyl, benzyl, phenethyl, phenoxy, benzyloxy, halogen, hydroxy, nitro, cyano, $C_1$-$C_4$ alkyl, $C_3$-$C_6$ cycloalkyl, $C_3$-$C_6$ cycloalkylmethyl, $C_7$-$C_{10}$ arylalkyl, $C_1$-$C_4$ alkoxy, —$CO_2H$, hydroxamic acid, hydrazide, boronic acid, sulfonamide, formyl, $C_3$-$C_6$ cycloalkoxy, —$OR^{13}$, —$NR^{13}R^{14}$, $C_1$-$C_4$ alkyl substituted with —$NR^{13}R^{14}$, $C_2$-$C_6$ alkoxyalkyl optionally substituted with —$Si(CH_3)_3$, $C_1$-$C_4$ hydroxyalkyl, methylenedioxy, ethylenedioxy, $C_1$-$C_4$ haloalkyl, $C_1$-$C_4$ haloalkoxy, $C_1$-$C_4$ alkoxycarbonyl, $C_1$-$C_4$ alkylcarbonyloxy, $C_1$-$C_4$ alkylcarbonyl, $C_1$-$C_4$ alkylcarbonylamino, —$S(O)_mR^{13}$, —$SO_2NR^{13}R^{14}$, —$NHSO_2R^{14}$, —$OCH_2CO_2R^{13}$, 2-(1-morpholino)ethoxy, —$C(R^{14})=N(OR^{14})$; or a 5- or 6-membered heterocyclic ring containing from 1 to 4 heteroatoms independently selected from oxygen, nitrogen or sulfur;

or $R^{12}$ may be a 3- or 4- carbon chain attached to adjacent carbons on the ring to form a fused 5- or 6-membered ring, said 5- or 6- membered ring being optionally substituted on the aliphatic carbons with halogen, $C_1$-$C_4$ alkyl, $C_1$-$C_4$ alkoxy, hydroxy, or —$NR^{13}R^{14}$; or when $R^{12}$ is attached to a saturated carbon atom, it may be =O or =S; or when $R^{12}$ is attached to sulfur it may be =O.

$R^{12}$, when a substituent on nitrogen, is selected from one or more of the following:

phenyl, benzyl, phenethyl, hydroxy, $C_1$-$C_4$ hydroxyalkyl, $C_1$-$C_4$ alkoxy, $C_1$-$C_4$ alkyl, $C_3$-$C_6$ cycloalkyl, $C_3$-$C_6$ cycloalkylmethyl, —$CH_2NR^{13}R^{14}$, —$NR^{13}R^{14}$, $C_2$-$C_6$ alkoxyalkyl, $C_1$-$C_4$ haloalkyl, $C_1$-$C_4$ alkoxycarbonyl, —$CO_2H$, $C_1$-$C_4$ alkylcarbonyloxy, $C_1$-$C_4$ alkylcarbonyl, —$C(R^{14})=N(OR^{14})$;

$R^{12A}$, when a substituent on carbon, is selected from one or more of the following:

phenyl, benzyl, phenethyl, phenoxy, benzyloxy, halogen, hydroxy, nitro, cyano, $C_1$-$C_4$ alkyl, $C_3$-$C_6$ cycloalkyl, $C_3$-$C_6$ cycloalkylmethyl, $C_7$-$C_{10}$ arylalkyl, $C_1$-$C_4$ alkoxy, —$CO_2H$, hydroxamic acid, hydrazide, boronic acid, sulfonamide, formyl, $C_3$-$C_6$ cycloalkoxy, —$OR^{13A}$, $C_2$-$C_6$ alkoxyalkyl optionally substituted with —$Si(CH_3)_3$, $C_1$-$C_4$ hydroxyalkyl, methylenedioxy, ethylenedioxy, $C_1$-$C_4$ haloalkyl, $C_1$-$C_4$ haloalkoxy, $C_1$-$C_4$ alkoxycarbonyl, $C_1$-$C_4$ alkylcarbonyloxy, $C_1$-$C_4$ alkylcarbonyl, $C_1$-$C_4$ alkylcarbonylamino, —$S(O)_mMe$, —$SO_2NH_2$, —$NHSO_2Me$, —$OCH_2CO_2R^{13A}$, 2-(1-morpholino) ethoxy; or a 5- or 6-membered heterocyclic ring containing from 1 to 4 heteroatoms independently selected from oxygen, nitrogen or sulfur; or $R^{12A}$ may be a 3- or 4- carbon chain attached to adjacent carbons on the ring to form a fused 5- or 6-membered ring, said 5- or 6- membered ring being optionally substituted on the aliphatic carbons with halogen, $C_1$-$C_4$ alkyl, $C_1$-$C_4$ alkoxy, hydroxy, or —$NH_2$; or, when $R^{12A}$ is attached to a saturated carbon atom, it may be =O or =S; or when $R^{12A}$ is attached to sulfur it may be =O.

$R^{12A}$, when a substituent on nitrogen, is selected from one or more of the following:

phenyl, benzyl, phenethyl, hydroxy, $C_1$-$C_4$ hydroxyalkyl, $C_1$-$C_4$ alkoxy, $C_1$-$C_4$ alkyl, $C_3$-$C_6$ cycloalkyl, $C_3$-$C_6$ cycloalkylmethyl, $C_2$-$C_6$ alkoxyalkyl, $C_1$-$C_4$ haloalkyl, $C_1$-$C_4$ alkoxycarbonyl, —$CO_2H$, $C_1$-$C_4$ alkylcarbonyloxy, $C_1$-$C_4$ alkylcarbonyl;

$R^{13}$ is independently selected from:

H;

heterocycle substituted with 0-3 $R^{11A}$ and 0-1 $R^{16}$;

phenyl substituted with 0-3 $R^{11A}$;

benzyl substituted with 0-3 $R^{11A}$;

$C_1$-$C_6$ alkyl substituted with 0-3 $R^{11A}$;

$C_2$-$C_4$ alkenyl substituted with 0-3 $R^{11}A$;

$C_1$-C6 alkylcarbonyl substituted with 0-3 $R^{11A}$;

$C_1$-C6 alkoxycarbonyl substituted with 0-3 $R^{11A}$;

$C_1$-C6 alkylaminocarbonyl substituted with 0-3 $R^{11}A$;

$C_3$-$C_6$ alkoxyalkyl substituted with 0-3 $R^{11A}$;

an amine protecting group when $R^{13}$ is bonded to N;

a hydroxyl or carboxyl protecting group when $R^{13}$ is bonded to O;

$R^{14}$ is independently selected from:

hydrogen, $C_1$-$C_6$ alkoxy, $C_2$-$C_6$ alkenyl, phenyl, benzyl, an amine protecting group when $R^{14}$ is bonded to N, a hydroxyl or carboxyl protecting group when $R^{14}$ is bonded to O; and $C_1$-$C_6$ alkyl substituted with 0-3 groups selected from OH, $C_1$-$C_4$ alkoxy, halogen, $R^{13}$ and $R^{14}$ can alternatively join to form —$(CH_2)_4$—, —$(CH_2)_5$, —$CH_2CH_2N(R^{15})CH_2CH_2$—, or —$CH_2CH_2OCH_2CH_2$—;

$R^{13A}$ and $R^{14A}$ are independently selected from: H, $C_1$–$C_6$ alkyl;

$R^{13A}$ and $R^{14A}$ can alternatively join to form —$(CH_2)_4$—, —$(CH_2)_5$—, —$CH_2CH_2N(R^{15})CH_2CH_2$—, or —$CH_2CH_2OCH_2CH_2$—;

$R^{15}$ is H or $CH_3$;

R16 is independently selected from:

halogen, —CN, —$NO_2$, $C_1$–$C_4$ haloalkyl, $C_1$–$C_4$ haloalkoxy, $C_1$–$C_4$ alkoxy, $C_1$–$C_6$ alkyl, $C_2$–$C_4$ alkenyl, $C_2$–$C_4$ alkynyl, phenethyl, phenoxy, $C_3$–$C_{10}$ cycloalkyl, $C_3$–$C_6$ cycloalkylmethyl, $C_7$–$C_{10}$ arylalkyl, $C_2$–$C_6$ alkoxyalkyl, $C_1$–$C_4$ alkylcarbonyloxy, $C_1$–$C_4$ alkylcarbonyl, benzyloxy, $C_3$–$C_6$ cycloalkoxy, or phenyl, said phenyl being optionally substituted with Cl, F, Br, CN, $NO_2$, $CF_3$, $C_1$–$C_4$ alkyl, $C_1$–$C_4$ alkoxy or OH, or alternately, $R^{11A}$ and $R^{16}$, when substituents on adjacent carbons, can be taken together with the carbon atoms to which they are attached to form a 5–6 membered carbocyclic or heterocyclic ring system, said carbocyclic or heterocyclic ring system being optionally substituted with Cl, F, Br, CN, $NO_2$, $CF_3$, $C_1$–$C_4$ alkyl, $C_1$–$C_4$ alkoxy or OH;

$R^{20}$ and $R^{21}$ are independently selected from:

$C_1$–$C_6$ alkyl substituted with 0–3 $R^{11}$;

$C_3$–$C_6$ alkoxyalkyl substituted with 0–3 $R^{11}$;

$C_1$–$C_6$ alkylcarbonyl substituted with 0–3 $R^{11}$;

$C_1$–$C_6$ alkoxycarbonyl substituted with 0–3 $R^{11}$;

$C_1$–$C_6$ alkylaminocarbonyl substituted with 0–3 $R^{11}$;

benzoyl substituted with 0–3 $R^{12}$;

phenoxycarbonyl substituted with 0–3 $R^{12}$;

phenylaminocarbonyl substituted with 0–3 $R^{12}$;

a hydroxyl protecting; or any group that, when administered to a mammalian subject, cleaves to form a free hydroxyl group;

$R^{20}$ and $R^{21}$ may also be taken together along with the oxygen atoms to which they are attached to form a group selected from the group consisting of:

—O—(—$CH_2CH_2CH_2CH_2CH_2$—)—O—, —O—$C(CH_2CH_3)_2$—O—, —O—$C(CH_3)(CH_2CH_3)$—O—, —O—$C(CH_2CH_2CH_2CH_3)_2$—O—, —O—$C(CH_3)(CH_2CH(CH_3)CH_3)$—O—, —O—CH(phenyl)—O—, —$OCH_2SCH_2$—, —$OCH_2OCH_2$—, —OS(=O)O—, —OC(=O)O—, —$OCH_2$O—, —OC(=S)O—, —OS$(=O)_2$O—, —OC(=O)C(=O)O—, —$OC(CH_3)_2$O—, and —OC($OCH_3$)($CH_2CH_3$)O—;

m is 0, 1 or 2;

$R^{22}$ is selected from the following:

$C_1$–$C_8$ alkyl substituted with 0–3 $R^{31}$;

$C_2$–$C_8$ alkenyl substituted with 0–3 $R^{31}$;

$C_2$–$C_8$ alkynyl substituted with 0–3 $R^{31}$;

a $C_3$–$C_{14}$ carbocyclic ring system substituted with 0–5 $R^{31}$ and 0–5 $R^{32}$;

a 5- to 10-membered heterocyclic ring system containing 1 to 4 heteroatoms independently selected from oxygen, nitrogen or sulfur, said heterocyclic ring system being substituted with 0–2 $R^{32}$;

$R^{23}=R^{22}$;

$R^{31}$ is selected from one or more of the following:

—OH, $C_1$–$C_4$ alkoxy, —$CO_2R^{15}$, —$COR^{15}$, keto, halogen, cyano, —$CH_2NR^{13}R^{14}$, —$NR^{13}R^{14}$, —$CO_2R^{13}$, —$C(=O)R^{11}$, —$OC(=O)R^{13}$, —$OR^{13}$, $C_2$–$C_6$ alkoxyalkyl, —$S(O)_mR^{13}$, —$NHC(=NH)NHR^{13}$, —$C(=NH)NHR^{13}$, —$C(=O)NR^{13}R^{14}$, —$NR^{14}C(=O)R^{13}$, =$NOR^{14}$, —$NR^{14}C(=O)OR^{14}$, —OC(=O) $NR^{13}R^{14}$, —$NR^{13}C(=O)NR^{13}R^{14}$, —$NR^{13}C(=S)NR^{13}R^{14}$, —$NR^{14}SO_2NR^{13}R^{14}$, —$NR^{14}SO_2R^{13}$, —$SO_{2NR}{}^{13}R^{14}$, $C_1$–$C_4$ alkyl, $C_2$–$C_4$ alkenyl, $C_3$–$C_{10}$ cycloalkyl, $C_3$–$C_6$ cycloalkylmethyl, benzyl, phenethyl, phenoxy, benzyloxy, nitro, $C_7$–$C_{10}$ arylalkyl, hydroxamic acid, hydrazide, oxime, boronic acid, sulfonamide, formyl, $C_3$–$C_6$ cycloalkoxy, $C_1$–$C_4$ alkyl substituted with —$NR^{13}R^{14}$, $C_1$–$C_4$ hydroxyalkyl, methylenedioxy, ethylenedioxy, $C_1$–$C_4$ haloalkyl, $C_1$–$C_4$ haloalkoxy, $C_1$–$C_4$ alkoxycarbonyl, $C_1$–$C_4$ alkylcarbonyloxy, $C_1$–$C_4$ alkylcarbonyl, $C_1$–$C_4$ alkylcarbonylamino, —$OCH_2CO_2R^{13}$, 2-(1-morpholino) ethoxy, azido, —$C(R^{14})$=$N(OR^{14})$; or a $C_5$–$C_{14}$ carbocyclic residue substituted with 0–5 $R^{32}$; or a 5- to 10-membered heterocyclic ring system containing 1 to 4 heteroatoms independently selected from oxygen, nitrogen or sulfur, said heterocyclic ring system being substituted with 0–2 $R^{32}$;

$R^{32}$, when a substituent on carbon, is selected from one or more of the following:

phenethyl, phenoxy, $C_3$–$C_{10}$ cycloalkyl, $C_3$–$C_6$ cycloalkylmethyl, $C_7$–$C_{10}$ arylalkyl, hydrazide, oxime, boronic acid, $C_2$–$C_6$ alkoxyalkyl, methylenedioxy, ethylenedioxy, $C_1$–$C_4$ alkylcarbonyloxy, —$NHSO_2R^{14}$, benzyloxy, halogen, 2-(1-morpholino)ethoxy, —$CO_2R^{13}$, hydroxamic acid, —$CONR^{13}NR^{13}R^{14}$, cyano, sulfonamide, —CHO, $C_3$–$C_6$ cycloalkoxy, —$NR^{13}R^{14}$, —$C(R^{14})$=$N(OR^{14})$, —$NO_2$, —$OR^{13}$, —$NR^{40}R^{41}$, $SO_mR^{13}$, —$SO_mNR^{13}R^{14}$, —$C(=O)NR^{13}R^{14}$, —$OC(=O)NR^{13}R^{14}$, —$C(=O)R^{11}$, —$OC(=O)R^{11}$, —$B(OH)_2$, $OCO_2R^{13}$, phenyl, —$C(=O)NR^{13}$—($C_1$–$C_4$ alkyl)—$NR^{13}R^{14}$, —$C(=O)NR^{40}R^{41}$, $C_1$–$C_4$ haloalkyl, $C_1$–$C_4$ haloalkoxy, $C_2$–$C_4$ haloalkenyl, $C_1$–$C_4$ haloalkynyl; or —$C(=O)NR^{13}C(R^{11})_2NR^{13}R^{14}$, —$C(=O)NR^{13}C(R^{11})_2NR^{13}CO_2R^{13}$, —$C(=O)NR^{13}$—($C_1$–$C_4$ alkyl)—$NR^{13}CO_2R^{13}$, —$C(=O)N(R^{13})$—($C_1$–$C_4$ alkyl)—$R^{11}$, —$C(=O)C(R^{11})_2NR^{13}R^{14}$, —$C(=O)C(R^{11})_2NR^{13}CO_2R^{13}$, —C(=O)—($C_1$–$C_4$ alkyl) —$NR^{13}R^{14}$, —C(=O)—($C_1$–$C_4$ alkyl) —$NR^{13}CO_2R^{13}$; or —$(CH_2)_pOR^{13}$, —$(CH_2)_pNHR^{13}$, —$(CH_2)_pCONHR^{13}$, —$(CH_2)_pSO_2NHR^{13}$, —$(CH_2)_nNHCOR^{13}$, —$(CH_2)_pNHCO_2R^{13}$, —$(CH_2)_nOCONHR^{13}$, —$(CH_2)_pNHCONHR^{13}$, —$(CH_2)_pC(=NH)NHR^{13}$; or $C_1$–$C_4$ alkoxy substituted with 0–4 groups selected from: $R^{11}$, $C_3$–$C_6$ cycloalkyl, —$CO_2R^{13}$, —$C(=O)NR^{13}R^{14}$, —$NR^{13}R^{14}$ or OH; or $C_1$–$C_4$ alkyl substituted with 0–4 groups selected from: $R^{11}$, =$NR^{14}$, =$NNR^{13}C(=O)NR^{13}R^{14}$, =$NNR^{13}C(=O)OR^{13}$, or —$NR^{13}R^{14}$; or $C_2$–$C_4$ alkenyl substituted with 0–4 $R^{11}$, $C_2$–$C_4$ alkynyl substituted with 0–4 $R^{11}$; or a 5- or 6-membered heterocyclic ring containing from 1 to 4 heteroatoms independently selected from oxygen, nitrogen or sulfur, substituted with 0–2 $R^{12}$; or or $R^{32}$ may be a 3- or 4- carbon chain attached to adjacent carbons on the ring to form a fused 5- or 6-membered ring, said 5- or 6- membered ring being optionally substituted on the aliphatic carbons with halogen, $C_1$–$C_4$ alkyl, $C_1$–$C_4$ alkoxy, hydroxy, or —$NR^{13}R^{14}$;

or, when $R^{32}$ is attached to a saturated carbon, it may be =O, =S, =NOH;

or when $R^{32}$ attached to sulfur it may be =O;

p is 0, 1, or 2 n is 1 or 2;

$R^{32}$, when a substituent on nitrogen, is selected from one or more of the following:

phenyl, benzyl, phenethyl, hydroxy, $C_1$–$C_4$ hydroxyalkyl, $C_1$–$C_4$ alkoxy, $C_1$–$C_4$ alkyl, $C_3$–$C_6$ cycloalkyl, $C_3$–$C_6$ cycloalkylmethyl, —$CH_2NR^{13}R^{14}$, —$NR^{13}R^{14}$, $C_2$–$C_6$ alkoxyalkyl, $C_1$–$C_4$ haloalkyl, $C_1$–$C_4$ alkoxycarbonyl, —$CO_2H$, $C_1$–$C_4$ alkylcarbonyloxy, $C_1$–$C_4$ alkylcarbonyl, —$C(R^{14})$=$N(OR^{14})$;

$R^{40}$ is selected from: H, $C_1$–$C3$ alkyl; and $R^{41}$ is selected from:

—$C(=O)NR^{13}R^{14}$;

—$C(=O) NR^{13}NR^{13}R^{14}$;

—$C(=O)C(R^{11})_2NR^{13}R^{14}$;

—$C(=O)C(R^{11})_2NR^{13}NR^{13}R^{14}$;

—$C(=O)C(R^{11})_2NR^{13}CO_2R^{13}$;

—$C(=O)H$;

—$C(=O)R^{11}$;

—$C(=O)$—$(C_1$–$C_4$ alkyl)—$NR^{13}R^{14}$;

—$C(=O)$—$(C_1$–$C_4$ alkyl)—$NR^{13}CO_2R^{13}$;

1–3 amino acids linked together via amide bonds, and linked to the N atom via the carboxylate terminus;

provided that functional groups in $R^4$, $R^7$, $R^{22}$ and $R^{23}$ that are reactive in steps (1) and (2) below are protected with protecting groups which are removed or converted to the desired functional group in accordance with step (3) below;

said process comprising one or more of the steps of:

step (1): contacting an amine of formula (I):

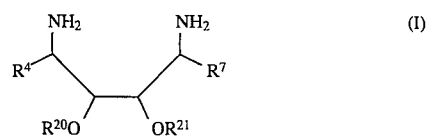

in a suitable solvent with at least two molar equivalents of an aldehyde $R^{22}$—CHO or $R^{23}$—CHO, in the presence of at least one molar equivalent of an acid and at least two molar equivalents of a suitable imine reducing agent for a period of time sufficient to form a compound of formula (II):

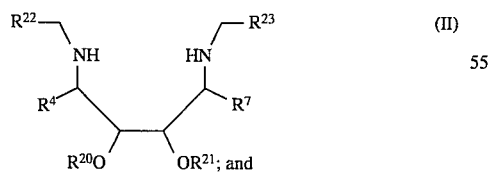

step (2): contacting the secondary amine of formula (II) in a suitable aprotic solvent at a suitable temperature in the presence of at least one molar equivalent of a hindered amine base with at least 0.3 molar equivalents of a suitable cyclizing agent at a suitable rate and for a suitable period of time to form a compound of formula (III):

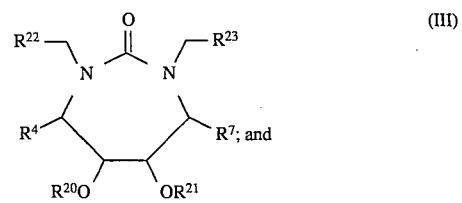

step (3): contacting the cyclic urea of formula (III) in a suitable solvent with one or more reagents or conditions or a combination or reagents or conditions for a period of time sufficient to effect the conversion of $R^{20}$ and $R^{21}$ to H and the deprotection or conversion of functional groups in $R^4$, $R^7$, $R^{22}$ and $R^{23}$ to the desired functional group in $R^4$, $R^7$, $R^{22}$ and $R^{23}$ to form the desired compound of formula (IV).

2. A process of claim 1 wherein:

$R^4$ and $R^7$ are independently selected from the following groups:

$C_1$–$C_8$ alkyl substituted with 0–3 $R^{11}$;

$C_2$–$C_8$ alkenyl substituted with 0–3 $R^{11}$;

$R^{11}$ is selected from one or more of the following:

H, keto, halogen, cyano, —$CH_2NR^{13}R^{14}$, —$NR^{13}R^{14}$, —$CO_2R^{13}$, —$OC(=O)R^{13}$, —$OR^{13}$, —$S(O)_mR^{13}$, $C_2$–$C_4$ alkenyl, $C_3$–$C_6$ cycloalkylmethyl, $C_3$–$C_{10}$ cycloalkyl substituted with 0–2 $R^{12}$, $C_1$–$C_4$ alkyl substituted with 0–2 $R^{12}$, aryl($C_1$–$C_3$ alkyl)-, substituted with 0–2 $R^{12}$, a $C_5$–$C_{14}$ carbocyclic residue substituted with 0–3 $R^{12}$;

a 5- to 10-membered heterocyclic ring system containing 1 to 4 heteroatoms independently selected from oxygen, nitrogen or sulfur, said heterocyclic ring system being substituted with 0–3 $R^{12}$;

$R^{11A}$ is selected from one or more of the following:

H, keto, halogen, cyano, —$CH_2N(R^{13A})R(14A)$, —$OR^{13A}$, —$N(R^{13A}) R(^{14A})$, $C_2$–$C_4$ alkenyl, $C_3$–$C_6$ cycloalkylmethyl, $C_3$–$C_{10}$ cycloalkyl substituted with 0–2 $R^{12A}$, $C_1$–$C_4$ alkyl substituted with 0–2 $R^{12A}$, aryl($C_1$–$C_3$ alkyl)- substituted with 0–2 $R^{12A}$;

$NO_2$, $C_1$–$C_6$ alkyl, or phenyl, said phenyl being optionally substituted with Cl, F, Br, CN, $NO_2$, $CF_3$, $OCH_3$ or OH;

a 5- to 10-membered heterocyclic ring system containing 1 to 4 heteroatoms independently selected from oxygen, nitrogen or sulfur, said heterocyclic ring system substituted with 0–3 $R^{12A}$.

$R^{12}$, when a substituent on carbon, is selected from one or more of the following:

phenyl, benzyl, phenethyl, benzyloxy, halogen, nitro, cyano, $C_1$–$C_4$ alkyl, $C_3$–$C_6$ cycloalkyl, $C_3$–$C_6$ cycloalkylmethyl, $C_7$–$C_{10}$ arylalkyl, $C_1$–$C_4$ alkoxy, formyl, $C_3$–$C_6$ cycloalkoxy, —$OR^{13}$, $C_2$–$C_6$ alkoxyalkyl optionally substituted with —$Si(CH_3)_3$, $C_1$–$C_4$ hydroxyalkyl, methylenedioxy, ethylenedioxy, —$S(O)_mR^{13}$, $CF_3$, 2-(1-morpholino)ethoxy, —$CO_2H$, hydroxamic acid, hydrazide, —$C(R^{14})$=$N(OR^{14})$, sulfonamide; or a 5- or 6-membered heterocyclic ring containing from 1 to 4 heteroatoms independently selected from oxygen, nitrogen or sulfur.

$R^{12}$, when a substituent on nitrogen, is selected from one or more of the following:

benzyl or methyl;

$R^{12A}$, when a substituent on carbon, is selected from one or more of the following:

phenyl, benzyl, phenethyl, benzyloxy, halogen, nitro, cyano, $C_1$–$C_4$ alkyl, $C_3$–$C_6$ cycloalkyl, $C_3$–$C_6$ cycloalkylmethyl, $C_7$–$C_{10}$ arylalkyl, $C_1$–$C_4$ alkoxy, formyl, $C_3$–$C_6$ cycloalkoxy, —$OR^{13A}$, $C_2$–$C_6$ alkoxyalkyl optionally substituted with —$Si(CH_3)_3$, —$S(O)_m Me$; or a 5- or 6-membered heterocyclic ring containing from 1 to 4 heteroatoms independently selected from oxygen, nitrogen or sulfur, $R^{12A}$, when a substituent on nitrogen, is selected from one or more of the following:

phenyl, benzyl, phenethyl, $C_1$–$C_4$ alkoxy, $C_1$–$C_4$ alkyl, $C_3$–$C_6$ cycloalkyl, $C_3$–$C_6$ cycloalkylmethyl, $C_2$–$C_6$ alkoxyalkyl, $C_1$–$C_4$ alkoxycarbonyl, $C_1$–$C_4$ alkylcarbonyloxy, $C_1$–$C_4$ alkylcarbonyl, $CF_3$, 2-(1-morpholino)ethoxy, —$CO_2H$, hydroxamic acid, hydrazide, —$C(R^{14A})$=$N(OR^{14A})$, sulfonamide;

$R^{13}$ is independently selected from:

a heterocycle selected from the group consisting of:

[heterocycle structures]

said heterocycle substituted with 0–3 $R^{11A}$ and 0–1 $R^{16}$;
H;
$C_1$–$C_6$ alkyl substituted with 0–3 $R^{11A}$;
$C_3$–$C_6$ alkoxyalkyl substituted with 0–3 $R^{11A}$;
$C_2$–$C_4$ alkenyl substituted with 0–3 $R^{11A}$;
benzyl substituted with 0–3 $R^{11A}$;
an amine protecting group when $R^{13}$ is bonded to N;
a hydroxyl or carboxyl protecting group when $R^{13}$ is bonded to O;

$R^{14}$ is independently selected from:

hydrogen, $CF_3$, $C_1$–$C_6$ alkyl, $C_1$–$C_6$ alkoxy, $C_2$–$C_6$ alkenyl, benzyl, an amine protecting group when $R^{14}$ is bonded to N, a hydroxyl or carboxyl protecting group when $R^{14}$ is bonded to O;

$R^{13}$ and $R^{14}$ can alternatively join to form —$(CH_2)_4$—, —$(CH_2)_5$—, —$CH_2CH_2N(R^{15})CH_2CH_2$—, or —$CH_2CH_2OCH_2CH_2$—;

$R^{13A}$ and $R^{14A}$ are independently selected from: H, $C_1$–$C_6$ alkyl;

$R^{13A}$ and $R^{14A}$ can alternatively join to form —$(CH_2)_4$—, —$(CH_2)_5$—, —$CH_2CH_2N(R^{15})CH_2CH_2$—, or —$CH_2CH_2OCH_2CH_2$—;

$R^{15}$ is H or $CH_3$;

$R^{16}$ is independently selected from:

halogen, $NO_2$, CN, $C_1$–$C_6$ alkyl, or phenyl, said phenyl being optionally substituted with Cl, F, Br, CN, $NO_2$, $CF_3$, $OCH_3$ or OH;

$R^{20}$ and $R^{21}$ are independently selected from:

$C_3$–$C_6$ alkoxyalkyl substituted with 0–3 $R^{11}$;
$C_1$–$C_6$ alkoxycarbonyl substituted with 0–3 $R^{11}$;
phenoxycarbonyl substituted with 0–3 $R^{12}$;
a hydroxyl protecting; or
any group that, when administered to a mammalian subject, cleaves to form a free hydroxyl group;

$R^{20}$ and $R^{21}$ may also be taken together along with the oxygen atoms to which they are attached to form a group selected from the group consisting of:

—O—(—$CH_2CH_2CH_2CH_2CH_2$—)—O—,
—O—$C(CH_2CH_3)_2$—O—, —O— $C(CH_3)(CH_2CH_3)$—O—, —O—$C(CH_2CH_2CH_2CH_3)_2$—O—,
—O— $C(CH_3)$ ( $CH_2CH(CH_3)CH_3$)—O—,
—O—CH(phenyl)—O—, —$OCH_2SCH_2O$—,
—$OCH_2OCH_2O$—, —$OCH_2O$—, —$OC(CH_3)_2O$—,
—$OC(OCH_3)$ ($CH_2CH_2CH_3$)O—, $R^{22}$ is selected from the following:

$C_1$–$C_8$ alkyl substituted with 0–3 $R^{31}$;
$C_2$–$C_8$ alkenyl substituted with 0–3 $R^{31}$;
$C_2$–$C_4$ alkynyl substituted with 0–3 $R^{31}$;
a $C_6$–$C_{10}$ aryl substituted with 0–3 $R^{31}$ and 0–3 $R^{32}$;
or a heterocycle selected from the group consisting of thiazole, indazole, thieno[2,3-c]pyrazole and thieno[3,2-c]pyrazole, said heterocycle substituted with 0–2 $R^{31}$;

$R^{23}=R^{22}$;

$R^{31}$ is selected from one or more of the following:

—OH, $C_1$–$C_4$ alkoxy, cyano, nitro, $C_1$–$C_4$ haloalkyl, $C_1$–$C_4$ haloalkoxy, —$CO_2R^{15}$, —$COR^{15}$, keto, halogen, —$CH_2NR^{13}R^{14}$, —$NR^{13}R^{14}$, —$OR^{13}$, $C_2$–$C_6$ alkoxyalkyl, $C_1$–$C_4$ alkyl, $C_2$–$C_4$ alkenyl, $C_3$–$C_{10}$ cycloalkyl, —$CO_2R^{13}$, —$S(O)_mR^{13}$;

a $C_5$–$C_{14}$ carbocyclic residue substituted with 0–5 $R^{32}$; or a 5- to 10-membered heterocyclic ring system containing 1 to 4 heteroatoms independently selected from oxygen, nitrogen or sulfur, said heterocyclic ring system being substituted with 0–2 $R^{32}$;

$R^{32}$, when a substituent on carbon, is selected from one or more of the following:

phenethyl, phenoxy, $C_3$–C10 cycloalkyl, $C_3$–$C_6$ cycloalkylmethyl, $C_7$–$C_{10}$ arylalkyl, $C_2$–$C_6$ alkoxyalkyl, methylenedioxy, ethylenedioxy, $C_1$–$C_4$ alkylcarbonyloxy, —$NHSO_2R^{14}$, benzyloxy, halogen, 2-(1-morpholino)ethoxy, —$CO_2R^{13}$, —$CONR^{13}NR^{13}R^{14}$, cyano, sulfonamide, —CHO, $C_3$–$C_6$ cycloalkoxy, —$NR^{13}R^{14}$, —$NO_2$, —$OR^{13}$, —$NR^{40}R^{41}$, —$SO_mR^{13}$, —$SO_mNR^{13}R^{14}$, —$C(=O)NR^{13}R^{14}$, —$OC(=O)NR^{13}R^{14}$, —$C(=O)R^{11}$, —$OC(=O)R^{11}$, —$OCO_2R^{13}$, phenyl, —$C(=O)NR^{13}$—($C_1$–$C_4$alkyl)—$NR^{13}R^{14}$, —$C(=O)NR^{40}R^{41}$, $C_1$–$C_4$ haloalkyl, $C_1$–$C_4$ haloalkoxy, $C_2$–$C_4$ haloalkenyl, $C_1$–$C_4$ haloalkynyl; or —$(CH_2)_pOR^{13}$, —$(CH_2)_pNHR^{13}$, —$(CH_2)_pCONHR^{13}$, —$(CH_2)_pSO_2NHR^{13}$, —$(CH_2)_nOCONHR^{13}$, —$(CH_2)_pNHCONHR^{13}$, —$(CH_2)_pC(=NH)NHR^{13}$; or —$C(=O)C(R^{11})_2NR^{13}R^{14}$;
—$C(=O)C(R^{11})_2NR^{13}CO_2R^{13}$;
—$C(=O)C(R^{11})_2NR^{13}CO_2R^{13}$; —$C(=O)$—($C_1$–$C_4$ alkyl)—$NR^{13}R^{14}$; —$C(=O)$—($C_1$–$C_4$ alkyl)—$NR^{13}CO_2R^{13}$; or $C_1$–$C_4$ alkoxy substituted with 0–4 groups selected from: $R^{11}$, $C_3$–$C_6$ cycloalkyl, —$CO_2R^{13}$, —$C(=O)NR^{13}R^{14}$, or —$NR^{13}R^{14}$; or $C_1$–$C_4$ alkyl substituted with 0–4 groups selected from: $R^{11}$, =$NR^{14}$, =$NNR^{13}C(=O)NR^{13}R^{14}$, or —$NR^{13}R^{14}$; or $C_2$–$C_4$ alkenyl substituted with 0–4 $R^{11}$, $C_2$–$C_4$ alkynyl substituted with 0–3 $R^{11}$; or a 5- or 6-membered heterocyclic ring containing from 1 to 4 heteroatoms independently selected from oxygen, nitrogen or sulfur, substituted with 0–2 $R^{12}$;

$R^{32}$, when a substituent on nitrogen, is selected from one or more of the following:

phenyl, benzyl, phenethyl, hydroxy, $C_1$–$C_4$ alkyl, $C_3$–$C_6$ cycloalkyl, $C_3$–$C_6$ cycloalkylmethyl, —$CH_2NR^{13}R^{14}$, —$NR^{13}R^{14}$, $C_2$–$C_6$ alkoxyalkyl, $C_1$–$C_4$ alkoxycarbonyl, $C_1$–$C_4$ alkylcarbonyloxy, $C_1$–$C_4$ alkylcarbonyl;

$R^{40}$ is selected from: H, $C_1$–$C_3$ alkyl; and $R^{41}$ is selected from:
—$C(=O)NR^{13}R^{14}$;
—$C(=O)NR^{13}NR^{13}R^{14}$;
—$C(=O)C(R^{11})_2NR^{13}R^{14}$;
—$C(=O)C(R^{11})_2NR^{13}NR^{13}R^{14}$;
—$C(=O)C(R^{11})_2NR^{13}CO_2R^{13}$;
—$C(=O)H$;
—$C(=O)R^{11}$;
—$C(=O)$—($C_1$–$C_4$ alkyl)—$NR^{13}R^{14}$;
—$C(=O)$—($C_1$–$C_4$ alkyl)—$NR^{13}CO_2R^{13}$;

1–3 amino acids linked together via amide bonds, and linked to the N atom via the carboxylate terminus.

3. A process of claim 1 wherein:

$R^4$ and $R^7$ are independently selected from the following groups:

$C_1$–$C_8$ alkyl substituted with 0–2 $R^{11}$;

$R^{11}$ is selected from one or more of the following:

H, halogen, —$OR^{13}$, $C_3$–$C_{10}$ cycloalkyl substituted with 0–2 $R^{12}$, $C_1$–$C_4$ alkyl substituted with 0–2 $R^{12}$, aryl($C_1$–$C_3$ alkyl)- substituted with 0–2 $R^{12}$; aryl substituted with 0–2 $R^{12}$;

a heterocyclic ring system selected from pyridyl, pyrimidinyl, triazinyl, furanyl, thienyl, pyrrolyl, pyrazolyl, imidazolyl, tetrazolyl, benzofuranyl, indolyl, quinolinyl, isoquinolinyl, oxazolidinyl, said heterocyclic ring system being substituted with 0–2 $R^{12}$;

$R^{11A}$ is selected from one or more of the following:

H, halogen, —$OR^{13A}$, $C_3$–$C_{10}$ cycloalkyl substituted with 0–2 $R^{12A}$, $C_1$–$C_4$ alkyl substituted with 0–2 $R^{12A}$, aryl($C_1$–$C_3$ alkyl)- substituted with 0–2 $R^{12A}$, aryl substituted with 0–2 $R^{12A}$; or $NO_2$, cyano, $C_1$–$C_6$ alkyl, or phenyl, said phenyl being optionally substituted with Cl, F, Br, CN, $NO_2$, $CF_3$, $OCH_3$ or OH; or a heterocyclic ring system selected from pyridyl, pyrimidinyl, triazinyl, furanyl, thienyl, pyrrolyl, pyrazolyl, imidazolyl, tetrazolyl, benzofuranyl, indolyl, quinolinyl, isoquinolinyl, oxazolidinyl, said heterocyclic ring system being substituted with 0–2 $R^{12A}$;

$R^{12}$, when a substituent on carbon, is selected from one or more of the following:

benzyloxy, halogen, methyl, nitro, cyano, $C_3$–$C_6$ cycloalkyl, $C_3$–$C_6$ cycloalkylmethyl, $C_7$–$C_{10}$ arylalkyl, $C_1$–$C_4$ alkoxy, formyl, $C_3$–$C_6$ cycloalkoxy, —$OR^{13}$, $C_2$–$C_6$ alkoxyalkyl optionally substituted with —$Si(CH_3)_3$, —$S(O)_mMe$, $CF_3$, 2-(1-morpholino)ethoxy, hydroxamic acid, hydrazide, —$C(R^{14})=N(OR^{14})$, sulfonamide;

$R^{12}$, when a substituent on nitrogen, is methyl;

$R^{12A}$, when a substituent on carbon, is selected from one or more of the following:

benzyloxy, halogen, methyl, nitro, cyano, $C_3$–$C_6$ cycloalkyl, $C_3$–$C_6$ cycloalkylmethyl, $C_7$–$C_{10}$ arylalkyl, $C_1$–$C_4$ alkoxy, formyl, $C_3$–$C_6$ cycloalkoxy, —$OR^{13A}$, $C_2$–$C_6$ alkoxyalkyl optionally substituted with —$Si(CH_3)_3$, —$S(O)_mMe$, $CF_3$, 2-(1-morpholino)ethoxy, —$CO_2H$, hydroxamic acid, hydrazide, —$C(R^{14A})=N(OR^{14}A)$, sulfonamide; or $R^{12A}$, when a substituent on nitrogen, is selected from one or more of the following:

benzyl or methyl;

$R^{13}$ is independently selected from the group consisting of:

a heterocycle selected from the group consisting of:

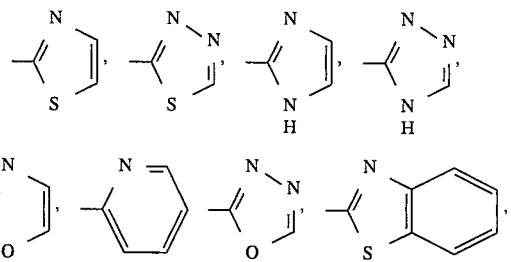

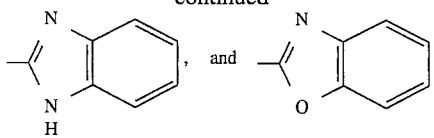

said heterocycle substituted with 0–1 $R^{114}$ and 0–1 $R^{16}$;

H, $C_1$–$C_4$ alkyl, $C_2$–$C_4$ alkenyl, benzyl, an amine protecting group when $R^{13}$ is bonded to N, and a hydroxyl or carboxyl protecting group when $R^{13}$ is bonded to O;

$R^{14}$ is independently selected from the group consisting of:

hydrogen, $CF_3$, $C_1$–$C_4$ alkyl, $C_1$–$C_4$ alkoxy, $C_2$–$C_4$ alkenyl, benzyl, an amine protecting group when $R^{14}$ is bonded to N, a hydroxyl or carboxyl protecting group when $R^{14}$ is bonded to O;

$R^{13}$ and $R^{14}$ can alternatively join to form —$(CH_2)_4$—, —$(CH_2)_5$—, —$CH_2CH_2N(R^{15})CH_2CH_2$—, or —$CH_2CH_2OCH_2CH_2$—;

$R^{13A}$ and $R^{14A}$ are independently selected from: H, $C_1$–$C_6$ alkyl;

$R^{13A}$ and $R^{14A}$ can alternatively join to form —$(CH_2)_4$—, —$(CH_2)_5$—, —$CH_2CH_2N(R^{15})CH_2CH_2$—, or —$CH_2CH_2OCH_2CH_2$—;

$R^{15}$ is H or $CH_3$;

$R^{16}$ is independently selected from:

halogen, $NO_2$, CN, $C_1$–$C_6$ alkyl, or phenyl, said phenyl being optionally substituted with Cl, F, Br, CN, $NO_2$, $CF_3$, $OCH_3$ or OH;

$R^{20}$ and $R^{21}$ are taken together along with the oxygen atoms to which they are attached to form a group selected from the group consisting of:

—O—(—$CH_2CH_2CH_2CH_2CH_2$—)—O—,
—O—$C(CH_2CH_3)_2$—O—, —$OCH_2OCH_2O$—,
—$OCH_2O$—, and —$OC(CH_3)_2O$—;

$R^{22}$ is selected from the following:

$C_1$–$C_8$ alkyl substituted with 0–2 $R^{31}$;

$C_2$–$C_6$ alkenyl substituted with 0–2 $R^{31}$;

phenyl substituted with 0–2 $R^{31}$ and 0–2 $R^{32}$;

or a heterocycle selected from the group consisting of thiazole, indazole, thieno[2,3-c]pyrazole and thieno[3,2-c] pyrazole, said heterocycle substituted with 0–2 $R^{31}$;

$R^{23}=R^{22}$;

$R^{31}$ is selected from one or more of the following:

—OH, —$OCH_3$, cyano, nitro, $CF_3$, $C_1$–$C_4$ haloalkoxy, —$CO_2R^{15}$, —$COR^{15}$, halogen, —$OR^{13}$, $C_1$–$C_4$ alkyl, $C_3$–$C_{10}$ cycloalkyl, —$CO_2R^{13}$, —$S(O)_mR^{13}$;

aryl substituted with 0–3 $R^{32}$; or a heterocyclic ring system chosen from pyridyl, pyrimidinyl, triazinyl, furanyl, thienyl, pyrrolyl, pyrazolyl, imidazolyl, tetrazolyl, benzofuranyl, indolyl, quinolinyl, isoquinolinyl, oxazolidinyl, benzimidazolyl, benzotriazolyl, indazolyl, benzoxazolinyl, benzoxazolyl, said heterocyclic ring being substituted with 0–2 $R^{32}$;

$R^{32}$, when a substituent on carbon, is selected from one or more of the following:

—$(CH_2)_pOR^{13}$, —$(CH_2)_pCONHR^{13}$, —$(CH_2)_nOCONHR^{13}$, —$(CH_2)_pNHCONHR^{13}$; or

—$CONH_2$, —$CO_2H$, —CHO, —$CH_2NHOH$, —$CH_2NR^{13}R^{14}$, —$NR^{13}R^{14}$, hydroxy, hydroxymethyl, —$C(R^{14})$=$N(OR^{14})$, halogen, methoxy, methyl, nitro, cyano, allyloxy, —$CO_2CH_3$, —NHCHO, —NHCOCH_3, —$OCO_2CH_3$, —CH=$NCH_2CH_2OH$, —$OCONHCH_2C_6H_5$, —$OCONHCH_3$, oxazolidinyl, —C≡C—$CH_2OH$, —$COCH_3$, hydroxyethyl, $C_1$–$C_3$ alkyl (said alkyl substituted with 0–4 halogen, or OH), tetrazolyl, —$OCH_2CONH_2$, —$CONHNH_2$, —CH=$NNHCONH_2$, —$CONHOCH_3$, —$CH_2CH(OH)CH_2OH$, adamantamido, hydroxyethoxy, dihydroxyethyl, —$C(NH_2)$=NH, —CONHCH_3, —$B(OH)_2$, benzyloxy, —$CONHCH_2CH_3$, —$CON(CH_2CH_3)_2$, methylthio, —$SO_2CH_3$, —NHCONH_2, -NHCONHCH_3, —$NHCOCH_2N$ $(CH_3)_2$, $NHCOCH_2NHCH_3$, —$NHCOCH_2NHCO_2CH_2C_6H_5$, —$NHCOCH_2NH_2$,
—$NHCOCH(CH_3)NHCO_2CH_2C_6H_5$,
—$NHCOCH(CH_2C_6H_5)NHCO_2CH_2C_6H_5$,
—$NHCOCH(CH_3)NH_2$, —$NHCOCH(CH_2C_6H_5)NH_2$,
—$CO_2CH_2CH_3$, —$CONHCH_2CH_3$, —$CONHCH(CH_3)_2$, —$CH_2$-imidazole, —$COC(CH_3)_3$, —$CH(OH)CF_3$, —CO—imidazole, —CO-pyrazolyl, oxadiazolidinonyl, —$COCF_3$, —$COCH_2CH_3$, —$COCH_2CH_2CH_3$, pyrazolyl, —$SO_2NH_2$, —$C(CH_2CH_3)$=N(OH), —$C(CF_3)$=N(OH), phenyl, acetoxy, hydroxyamino, —$N(CH_3)$ (CHO), cyclopropylmethoxy, —$CONR^{13}R^{14}$, —CONHOH, (diethylaminoethyl)aminocarbonyl, (N-ethyl,N-methylaminoethyl)aminocarbonyl,
(4-methylpiperazinylethyl)aminocarbonyl, (pyrrolidinylethyl)aminocarbonyl, (piperidinylethyl)aminocarbonyl, —$NHCOCH_2NHCH_3$, N-(2-(4-morpholino)ethyl)aminocarbonyl, N-(2-(N,N-dimethylamino)ethyl)aminocarbonyl;

p is 0; and $R^{32}$, when a substituent on nitrogen, is selected from one or more of the following:

benzyl or methyl.

4. A process of claim 1 wherein:

$R^4$ and $R^7$ are independently $C_1$–$C_3$ alkyl substituted with 0–1 $R^{11}$;

$R^{11}$ is selected from one or more of the following:

H, halogen, —$OR^{13}$, $C_3$–$C_{10}$ cycloalkyl substituted with 0–2 $R^{12}$, $C_1$–$C_4$ alkyl substituted with 0–2 $R^{12}$, aryl($C_1$–$C_3$ alkyl)- substituted with 0–2 $R^{12}$; aryl substituted with 0–2 $R^{12}$;

a heterocyclic ring system selected from pyridyl, pyrimidinyl, triazinyl, furanyl, thienyl, pyrrolyl, pyrazolyl, imidazolyl, tetrazolyl, benzofuranyl, indolyl, quinolinyl, isoquinolinyl, oxazolidinyl, said heterocyclic ring system being substituted with 0–2 $R^{12}$;

$R^{11A}$ is selected from one or more of the following:

H, halogen, —$OR^{13A}$, $C_3$–$C_{10}$ cycloalkyl substituted with 0–2 $R^{12A}$, $C_1$–$C_4$ alkyl substitued with 0–2 $R^{12A}$, aryl($C_1$–$C_3$ alkyl)- substituted with 0–2 $R^{12A}$; aryl substituted with 0–2 $R^{12A}$; or $NO_2$, cyano, $C_1$–$C_6$ alkyl, or phenyl, said phenyl being optionally substituted with Cl, F, Br, CN, $NO_2$, $CF_3$, $OCH_3$ or OH; or a heterocyclic ring system selected from pyridyl, pyrimidinyl, triazinyl, furanyl, thienyl, pyrrolyl, pyrazolyl, imidazolyl, tetrazolyl, benzofuranyl, indolyl, quinolinyl, isoquinolinyl, oxazolidinyl, said heterocyclic ring system being substituted with 0–2 $R^{12A}$;

$R^{12}$, when a substituent on carbon, is selected from one or more of the following:

benzyloxy, halogen, methyl, nitro, cyano, $C_3$–$C_6$ cycloalkyl, $C_3$–$C_6$ cycloalkylmethyl, $C_7$–$C_{10}$ arylalkyl, $C_1$–$C_4$ alkoxy, formyl, $C_3$–$C_6$ cycloalkoxy, —$OR^{13}$, $C_2$–$C_6$ alkoxyalkyl optionally substituted with —$Si(CH_3)_3$, —$S(O)_mMe$, $CF_3$, 2-(1-morpholino)

ethoxy, hydroxamic acid, hydrazide, —C(R$^{14}$)=N(OR$^{14}$), sulfonamide;

R$^{12}$, when a substituent on nitrogen, is methyl;

R$^{12A}$, when a substituent on carbon, is selected from one or more of the following:

benzyloxy, halogen, methyl, nitro, cyano, C$_3$–C$_6$ cycloalkyl, C$_3$–C$_6$ cycloalkylmethyl, C$_7$–C$_{10}$ arylalkyl, C$_1$–C$_4$ alkoxy, formyl, C$_3$–C$_6$ cycloalkoxy, —OR$^{13A}$, C$_2$–C$_6$ alkoxyalkyl optionally substituted with —Si(CH$_3$)$_3$, —S(O)$_m$Me, CF$_3$, 2-(1-morpholino) ethoxy, —CO$_2$H, hydroxamic acid, hydrazide, —C(R$^{14A}$)=N(OR$^{14A}$), sulfonamide; or R$^{12A}$, when a substituent on nitrogen, is methyl;

R$^{13}$ is independently selected from the group consisting of:

a heterocycle selected from the group consisting of:

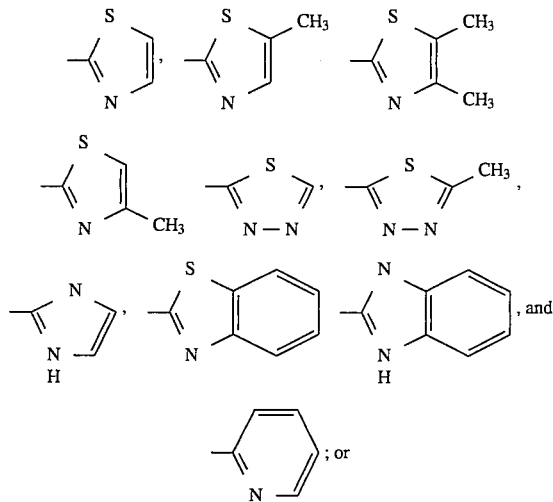

H, C$_1$–C$_4$ alkyl, C$_2$–C$_4$ alkenyl, benzyl, an amine protecting group when R$^{13}$ is bonded to N, and a hydroxyl or carboxyl protecting group when R$^{13}$ is bonded to O;

R$^{13}$ and R$^{14}$ can alternatively join to form —(CH$_2$)$_4$—, —(CH$_2$)$_5$—, —CH$_2$CH$_2$N(R$^{15}$)CH$_2$CH$_2$—, or —CH$_2$CH$_2$OCH$_2$CH$_2$—;

R$^{13A}$ and R$^{14A}$ are independently selected from: H, C$_1$–C$_6$ alkyl;

R$^{13A}$ and R$^{14A}$ can alternatively join to form —(CH$_2$)$_4$—, —(CH$_2$)$_5$—, —CH$_2$CH$_2$N(R$^{15}$)CH$_2$CH$_2$—, or —CH$_2$CH$_2$OCH$_2$CH$_2$—;

R$^{15}$ is H or CH$_3$;

R$^{20}$ and R$^{21}$ are taken together along with the oxygen atoms to which they are attached to form a group selected from the group consisting of:

—O—(CH$_2$CH$_3$)$_2$—O—, —OCH$_2$OCH$_2$O—, —OCH$_2$O—, and —OC(CH$_3$)$_2$O—;

R$^{22}$ is selected from the following:

C$_1$–C$_8$ alkyl substituted with 0–2 R$^{31}$;

phenyl substituted with 0–2 R$^{31}$ and 0–2 R$^{32}$;

or a heterocycle selected from the group consisting of thiazole, indazole, thieno [2,3-c]pyrazole and thieno [3,2-c]pyrazole, said heterocycle substituted with 0–2 R$^{31}$;

R$^{23}$=R$^{22}$;

R$^{31}$ is selected from one or more of the following:

—OH, —OCH$_3$, cyano, nitro, CF$_3$, C$_1$–C$_4$ haloalkoxy, —CO$_2$R$^{15}$, —COR$^{15}$, halogen, —OR$^{13}$, C$_1$–C$_4$ alkyl, C$_3$–C$_{10}$ cycloalkyl, —CO$_2$R$^{13}$, —S(O)$_m$R$^{13}$;

aryl substituted with 0–3 R$^{32}$; or a heterocyclic ring system chosen from pyridyl, pyrimidinyl, triazinyl, furanyl, thienyl, pyrrolyl, pyrazolyl, imidazolyl, tetrazolyl, benzofuranyl, indolyl, quinolinyl, isoquinolinyl, oxazolidinyl, benzimidazolyl, benzotriazolyl, indazolyl, benzoxazolinyl, benzoxazolyl, said heterocyclic ring being substituted with 0–2 R$^{32}$;

R$^{32}$, when a substituent on carbon, is selected from one or more of the following:

—(CH$_2$)$_p$OR$^{13}$, —(CH$_2$)$_p$CONHR$^{13}$, —CONH$_2$, —CO$_2$H, —CHO, —CH$_2$NHOH, —CH$_2$NR$^{13}$R$^{14}$, —NR$^{13}$R$^{14}$, hydroxy, hydroxymethyl, —C(R$^{14}$)=N(OR$^{14}$), halogen, methoxy, methyl, nitro, cyano, allyloxy, —CO$_2$CH$_3$, —NHCHO, —NHCOCH$_3$, —OCO$_2$CH$_3$, —CH=NCH$_2$CH$_2$OH, —OCONHCH$_2$C$_6$H$_5$, —OCONHCH$_3$, oxazolidinyl, —C=C—CH$_2$OH, —COCH$_3$, hydroxyethyl, C$_1$–C$_3$ alkyl (said alkyl substituted with 0–4 halogen, or OH), tetrazolyl, —OCH$_2$ CONH$_2$, —CONHNH$_2$, —CH=NNHCONH$_2$, —CONHOCH$_3$, —CH$_2$CH(OH)CH$_2$OH, adamantamido, hydroxyethoxy, dihydroxyethyl, —C(NH$_2$)=NH, —CONHCH$_3$, —B(OH)$_2$, benzyloxy, —CONHCH$_2$CH$_3$, —CON(CH$_2$CH$_3$)$_2$, methylthio, —SO$_2$CH$_3$, —NHCONH$_2$, —NHCONHCH$_3$, NHCOCH$_2$N(CH$_3$)$_2$, —NHCOCH$_2$NHCH$_3$, —NHCOCH$_2$NHCO$_2$CH$_2$C$_6$H$_5$, —NHCOCH$_2$NH$_2$, —NHCOCH(CH$_3$)NHCO$_2$CH$_2$C$_6$H$_5$, —NHCOCH(CH$_2$C$_6$H$_5$)NHCO$_2$CH$_2$C$_6$H$_5$, —NHCOC(CH$_3$)NH$_2$, —NHCOCH(CH$_2$C$_6$H$_5$)NH$_2$, —CO$_2$CH$_2$CH$_3$, —CONHCH$_2$CH$_2$CH$_3$, —CONHCH(CH$_3$)$_2$, CH$_2$-imidazole, —COC(CH3)$_3$, —CH(OH)CF$_3$, —CO-imidazole, —CO-pyrazolyl, oxadiazolidinonyl, —COCF$_3$, —COCH$_2$CH$_3$, —COCH$_2$CH$_2$CH$_3$, pyrazolyl, —SO$_2$NH$_2$, —C(CH$_2$CH$_3$)=N(OH), —C(CF$_3$)=N(OH), phenyl, acetoxy, hydroxyamino, —N(CH$_3$) (CHO), cyclopropylmethoxy, —CONR$^{13}$R$^{14}$, —CONHOH, (diethylaminoethyl)aminocarbonyl, (N-ethyl,N-methylaminoethyl)aminocarbonyl,
(4-methylpiperazinylethyl)aminocarbonyl, (pyrrolidinylethyl)aminocarbonyl, (piperidinylethyl)aminocarbonyl, —NHCOCH$_2$NHCH$_3$, N-(2-(4-morpholino)ethyl)aminocarbonyl, N-(2-(N,N-dimethylamino)ethyl)aminocarbonyl;

p is 0; and

R$^{32}$ when a substituent on nitrogen, is methyl.

5. A process of claim 1 wherein:

R$^4$ and R$^7$ are independently selected from:

benzyl, fluorobenzyl, pyrrolylmethyl, methoxybenzyl, isobutyl, nitrobenzyl, aminobenzyl, thienylmethyl, hydroxybenzyl, pyridylmethyl, naphthylmethyl, thiomethylbenzyl, thiazolylmethyl, 3,4-methylenedioxybenzyl, and N,N-dimethylaminobenzyl;

R$^{20}$ and R$^{21}$ are taken together along with the oxygen atoms to which they are attached to form a group selected from the group consisting of:

—OCH$_2$OCH$_2$O— and —OC(CH$_3$)$_2$O—;

R$^{22}$ is selected from the group consisting of:

allyl, methyl, ethyl, propyl, cyclopropyl, cyclopropylmethyl, n-butyl, i-butyl, CH$_2$CH=C(CH$_3$)$_2$, pyridinylmethyl, pyridinyl, methallyl, n-pentyl, i-pentyl, hexyl, phenyl, isoprenyl, propargyl, picolinyl, methoxymethyl, cyclohexyl, dimethylbutyl, ethoxymethyl, methyloxazolinylmethyl, naphthyl, methyloxazolinyl, vinyloxymethyl, pentafluorophenyl, quinolinyl, carboxyphenyl, chloro-thienyl, benzyloxyphenyl, biphenyl, adamantyl, cyclopropylmethoxyphenyl, methoxyphenyl, methylphenyl, ethoxyphenyl, hydroxyphenyl, hydroxymethylphenyl, aminophenyl, formylphenyl, cyanophenyl, cinnamyl, allyloxyphenyl, fluorophenyl, difluorophenyl, chlorophenyl, chloromethylphenyl, fluoromethylphenyl, iodophenyl, bromophenyl, cyclobutyl, formaldoximephenyl, cyclopentyl, nitrophenyl, ($H_2NC(=O)$)-phenyl, carbomethoxyphenyl, carboethoxyphenyl, tetrazolylphenyl, dimethylallyl, aminomethylphenyl, (O-benzyl-formaldoxime)phenyl, (O-methylformaldoxime)phenyl, ($CH_3O_2CO$)-phenyl, ($HOCH_2CH_2N=CH$)-phenyl, N-benzylaminocarbonylphenyl, N-methylaminophenyl, N-ethylaminophenyl, N-ethylaminomethylphenyl, acetylphenyl, acetoxyphenyl, N-hydroxylaminophenyl, phenylmethylboronic acid, N-hydroxylaminomethylphenyl, (hydroxyl) ethylphenyl, ($CH_3C(=NOH)$)-phenyl, ($H_2NNHC(=O)$)-phenyl, ($H_2NC(=O)NHN=CH$)-phenyl, ($CH_3ONHC(=O)$)-phenyl, ($HONHC(=O)$)-phenyl, ($CH_3NHC(=O)$)-phenyl, N,N- dimethylaminocarbonylphenyl, ($HOCH_2CH(OH)CH_2O$)-phenyl, hydroxyethoxyphenyl (oxazolidinyl)-phenyl, (hydroxyl)pentyl, pentenyl, (hydroxy)heptyl, (hydroxyl)butyl, (carboxy)butyl, (carbomethoxy)butyl, (methylthio)phenyl, (methylsulfonyl)phenyl, N,N-dimethylaminomethylphenyl, N-methylaminomethylphenyl, glycylaminophenyl, N,N-dimethylglycylaminophenyl, alanylaminophenyl, (N-phenylmethoxycarbonyl)alanylaminophenyl, phenylalanylaminophenyl, (N-phenylmethoxycarbonyl) phenylalanylaminophenyl, ($CH_3CH_2NHC(=O)$)-phenyl, N,N-diethylaminocarbonylphenyl, N-ethylaminocarbonylphenyl, N-propylaminocarbonylphenyl, N,N-diisopropylaminocarbonylphenyl, N,N-di-n-propylaminocarbonylphenyl, (hydroxypropynyl) phenyl, (imidazolyl-C (=O))-phenyl, (pyrazolyl-C(=O))-phenyl, (pyridylmethylaminocarbonyl)phenyl, (oxadiazolidinonyl)phenyl, trifluoroacetylphenyl, (pyrazolyl)phenyl, ($H_2NSO_2$)-phenyl, dihydroxyethylphenyl, (MeHNC(=O)NH)-phenyl, ($H_2NC(=O)NH$)-phenyl, (HC(=O)NH)-phenyl, methanesulfonylpentyl, methoxypentyl, N-formyl-N-methylaminophenyl, acetylaminophenyl, propionylphenyl, butyrylphenyl, ($CH_3CH_2C(=NOH)$)-phenyl, (trifluorohydroxyethyl)phenyl, ($CF_3C(=NOH)$)-phenyl, (N-methylglycyl) aminophenyl, ((4-morpholino)ethyl)aminocarbonylphenyl, (N,N-dimethylaminoethyl)aminocarbonylphenyl, (N,N-diethylaminoethyl)aminocarbonylphenyl, (4-methylpiperazin-1-ylethyl)aminocarbonylphenyl, (benzyl-NHC(=O)O)phenyl, ($CH_3NHC$ (=O)O) phenyl, ($NH_2C$ (=O)$CH_2O$) phenyl, ($NH_2C(=NH)$) phenyl, ((N-phenylmethoxycarbonyl)glycylamino)phenyl, (imidazolylmethyl)phenyl, (($CH_3$)$_3$C—C(=O))phenyl, (N-methyl-N-ethylaminoethyl)aminocarbonylphenyl, (pyrrolidinylethyl)aminocarbonylphenyl, (piperidinylethyl)aminocarbonylphenyl, ($H_2NC(=NOH)$)phenyl, ($H_2NC(=NOH)$) fluorophenyl, benzimidazolyl, benzotriazolyl, indazolyl, benzoxazolinyl, benzisoxazolyl, thienyl, furyl, benzyl, N-butylaminophenyl, N,N-dimethylaminophenyl, N-propylaminophenyl, N-methylaminomethylphenyl, carbomethoxyphenyl, N-methylaminocarbonylphenyl, glycylaminophenyl, N,N-dimethylaminocarbonylphenyl, N,N-diethylaminophenyl, alanylaminophenyl, phenylalanylaminophenyl, (N-methylglycyl)aminophenyl, ($H_2NC(=NOH)$)phenyl, ($CH_3C(=NOH)$)phenyl, 2-amino-5-benzoxazolyl, 3-amino-5-benzisoxazolyl, 3-amino-5-indazolyl, 3-methylamino-5-indazolyl, 3-ethylamino-5-indazolyl, 3-methyl-5-indazolyl, 3-methoxy-5-indazolyl, 3-chloro-5-indazolyl, 3,4-methylenedioxyphenyl, pyridyl, 3-(2-thiazolylaminocarbonyl)phenyl, 3-(4-methyl-2-thiazolylaminocarbonyl)phenyl, 3-(1,3,4-thiadiazol-2-ylaminocarbonyl)phenyl, 3-(5-methyl-1,3,4-thiadiazol-2-ylaminocarbonyl)phenyl, 3-(5-t-butyl-1,3,4-thiadiazol-2-ylaminocarbonyl)phenyl, 3(5-methyl-2-thiazolylaminocarbonyl)phenyl, 3-(4,5-dimethyl-2-thiazolylaminocarbonyl)phenyl, 3-(2-imidazolylaminocarbonyl)phenyl, 3-(2-pyridylaminocarbonyl)phenyl, 3-(2benzothiazolylaminocarbonyl)phenyl, 3-(2-benzimidazolylaminocarbonyl)phenyl, 3-(2-thiazolyloxy)phenyl, and 3-(2-pyridinyloxy)phenyl; $R^{23}=R^{22}$.

6. A method of claim 2, wherein:

in step (1), the compound of formula (I), in the presence of 2.0–3.0 molar equivalents of a hindered amine base in a suitable solvent, is contacted with two to three molar equivalents of aldehyde $R^{22}$—CHO or $R^{23}$—CHO, 1–4 molar equivalents of an acid, and 2–7 molar equivalents of a suitable imine reducing agent for a period of 1–24 hr to form a compound of formula (II) which is isolated; and in step (2), the compound of formula (II) in an aprotic solvent at a temperature of ambient to solvent reflux in the presence of 1.0–5.0 molar equivalents of a hindered amine base is contacted with 0.3–4.0 molar equivalents of a suitable cyclizing agent, added at an even rate over the entire reaction period for a period of 1–12 hr to form a compound of formula (III) which is optionally isolated.

7. A method of claim 6, wherein:

in step (1), the acid is an organic carboxylic acid and the imine reducing agent is a borohydride or pyridine,borane complex; and in step (2), the cyclizing agent is phosgene or triphosgene and the hindered amine base is diisopropylethylamine.

8. A method of claim 7 wherein in step (1) the acid is acetic acid and the imine reducing agent is sodium triacetoxyborohydride.

\* \* \* \* \*